US 11,781,099 B2

(12) United States Patent
Washio et al.

(10) Patent No.: US 11,781,099 B2
(45) Date of Patent: Oct. 10, 2023

(54) NUMBER ANALYZING METHOD, NUMBER ANALYZING DEVICE, AND STORAGE MEDIUM FOR NUMBER ANALYSIS

(71) Applicant: AIPORE INC., Shibuya-ku (JP)

(72) Inventors: Takashi Washio, Suita (JP); Tomoji Kawai, Suita (JP); Masateru Taniguchi, Suita (JP); Makusu Tsutsui, Suita (JP); Kazumichi Yokota, Suita (JP); Akira Ishi, Suita (JP); Takeshi Yoshida, Suita (JP)

(73) Assignee: AIPORE INC., Tokyo (JP)

( * ) Notice: Subject to any disclaimer, the term of this patent is extended or adjusted under 35 U.S.C. 154(b) by 0 days.

(21) Appl. No.: 18/099,191

(22) Filed: Jan. 19, 2023

(65) Prior Publication Data

US 2023/0159870 A1 May 25, 2023

Related U.S. Application Data

(62) Division of application No. 16/065,633, filed as application No. PCT/JP2016/087821 on Dec. 19, 2016, now Pat. No. 11,597,898.

(30) Foreign Application Priority Data

Dec. 25, 2015 (JP) .................. 2015-254398

(51) Int. Cl.
  *G01N 27/447* (2006.01)
  *C12M 1/34* (2006.01)
  (Continued)

(52) U.S. Cl.
  CPC ............ *C12M 1/34* (2013.01); *C12Q 1/04* (2013.01); *G01N 15/12* (2013.01);
  (Continued)

(58) Field of Classification Search
  CPC ............ G16B 40/10; G01N 27/3278; G01N 33/48721; G01N 15/1456; G01N 15/12;
  (Continued)

(56) References Cited

U.S. PATENT DOCUMENTS

| 3,961,249 A | 6/1976 | Coulter |
| 5,059,395 A | 10/1991 | Brittenham et al. |

(Continued)

FOREIGN PATENT DOCUMENTS

| JP | 58-041336 A | 3/1983 |
| JP | 58-083234 A | 5/1983 |

(Continued)

OTHER PUBLICATIONS

International Search Report dated Mar. 14, 2017 issued in corresponding PCT Application PCT/JP2016/087821.
(Continued)

*Primary Examiner* — Hoa Q Pham
(74) *Attorney, Agent, or Firm* — Norton Rose Fulbright US LLP

(57) ABSTRACT

A number analyzing method, a number analyzing device, and a storage medium for number analysis are disclosed, which enable, with high accuracy, analysis of the number or number distribution of particulate or molecular analytes according to the kinds of the analytes. A computer control program is executed on the basis of a data group of particle-passage detection signals which are detected by a nanopore device in accordance with passage of subject particles through a through-hole. Also, a particle type distribution estimating program is executed, to estimate probability density on the basis of a data group based on feature values indicating feature of the waveforms of pulse signals which correspond to the passage of particles and which are (Continued)

obtained as the particle-passage detection signals. Thus, the number of particles can be derived for each particle type.

13 Claims, 53 Drawing Sheets

(51) Int. Cl.
*G01N 33/487* (2006.01)
*C12Q 1/04* (2006.01)
*G01N 15/12* (2006.01)
*G01N 15/10* (2006.01)

(52) U.S. Cl.
CPC .......... *G01N 33/48721* (2013.01); *G01N 2015/1006* (2013.01); *G01N 2015/1018* (2013.01); *G01N 2015/1087* (2013.01); *G01N 2015/1093* (2013.01)

(58) Field of Classification Search
CPC ... G01N 2015/1037; G01N 2015/1062; G01N 2015/1081; G01N 27/44791; G06F 17/18; G06F 11/079; G06K 9/6232; G06K 9/6268; G06N 20/10; G06N 20/00; G16C 20/70
USPC .................................. 356/335–343, 432–440
See application file for complete search history.

(56) References Cited

U.S. PATENT DOCUMENTS

| | | | |
|---|---|---|---|
| 5,719,666 A | 2/1998 | Fukuda et al. | |
| 8,273,532 B2* | 9/2012 | Gershow .............. | C12Q 1/6825 977/932 |
| 8,702,940 B2 | 4/2014 | Peng et al. | |
| 9,726,636 B2 | 8/2017 | Hongo et al. | |
| 9,804,116 B2 | 10/2017 | Hongo et al. | |
| 11,313,850 B2 | 4/2022 | Sato | |
| 11,597,898 B2* | 3/2023 | Washio ................... | G06N 20/10 |
| 2001/0005130 A1 | 6/2001 | Manzini et al. | |
| 2001/0032495 A1 | 10/2001 | Ueno et al. | |
| 2009/0136958 A1 | 5/2009 | Gershaw et al. | |
| 2012/0040312 A1* | 2/2012 | Hinders ................ | G06T 7/0012 433/215 |
| 2016/0018384 A1* | 1/2016 | Lindsay ........... | G01N 27/44747 435/24 |
| 2018/0209953 A1 | 7/2018 | Lindsay et al. | |
| 2019/0353635 A1 | 11/2019 | Lindsay et al. | |
| 2020/0251184 A1* | 8/2020 | Washio ................... | G06F 17/18 |
| 2021/0140938 A1* | 5/2021 | Washio ............ | G01N 33/48721 |

FOREIGN PATENT DOCUMENTS

| | | |
|---|---|---|
| JP | 58-189543 A | 11/1983 |
| JP | 01-250037 A | 10/1989 |
| JP | 08-136438 A | 5/1996 |
| JP | 2001-305041 A | 10/2001 |
| WO | 2009/045472 A1 | 4/2009 |
| WO | 2013/136430 A1 | 9/2013 |
| WO | 2013/137209 A1 | 9/2013 |
| WO | 2014/138253 A1 | 9/2014 |
| WO | 2015/099116 A1 | 7/2015 |

OTHER PUBLICATIONS

Gaurav Goyal et al., "Use of solid-state nanopores for sensing co-translocational deformation of nano-liposomes" Analyst, 2015, 140, 4865, Royal Society of Chemistry; accepted Mar. 17, 2015.
Aki Hide Arima et al., "Discrimination of equi-sized nanoparticles by surface charge state usng lo-aspect-ratio pore sensors" Applied Physics Letters, AIP Publishing LLC, 104, 163112 (2014), accepted Apr. 16, 2014; published online Apr. 25, 2014.
Gaurav Goyal et al., "Low aspect ratio micropores for single-particle and single-cell analysis" Electrophoresis 2015, 36, 1164-1171, revised Feb. 13, 2015; accepted Feb. 14, 2015.
Chihiro Kawaguchi et al., "Electrical detection of single pollen allergen particles using electrode-embedded microchannels", IOP Publishing Ltd received Jun. 28, 2011; published Mar. 30, 2012.
European Search Report dated Jul. 25, 2019 issued in corresponding EP patent application 16878642.4.
Chinese Office Action dated Nov. 4, 2020 issued in corresponding CN patent application 201680075604.X.

* cited by examiner

Fig. 6

(6A)
$$x_t = Fx_{t-1} + Gu_{t-1}$$
$$u_t \sim N(0, \sigma_{u,t}^2)$$

$x_t$ : State vector at time t (Estimation target)
$u_t$ : System control input at time t
$\sim N(0, \sigma_{u,t}^2)$ : Follows the normal distribution with average 0 and dispersion $\sigma_{u,t}^2$
$F$ : State transition matrix
$G$ : System control input matrix (6B)
$$y_t = Hx_t + v_t$$
$$v_t \sim N(0, \sigma_{v,t}^2)$$

$y_t$ : Observation vector at time t
$v_t$ : Observation noise at time t
$\sim N(0, \sigma_{v,t}^2)$ : follows the normal distribution with average 0 and dispersion $\sigma_{v,t}^2$
$H$ : Observation matrix (6C)
$$x_t = x_{t-1} + u_{t-1}$$
$$y_t = x_t + v_t$$

$x_t$ : Base line level of the real electric current at time t
$y_t$ : Electric current measured at time t
$u_t \sim N(0, \sigma_u^2)$ : System control input
$v_t \sim N(0, \sigma_{v,t}^2)$ : Observation noise at time t

| k \ α | 2 | 3 | 4 | 6 |
|---|---|---|---|---|
| 10 | 1,578 | 79 | 18 | 13 |
| 30 | 186 | 19 | 12 | 12 |
| 50 | 41 | 14 | 12 | 12 |
| 70 | 21 | 12 | 12 | 12 |
| 90 | 15 | 12 | 12 | 12 |

(12B)

m=50000

| k \ α | 2 | 3 | 4 | 6 |
|---|---|---|---|---|
| 10 | 1,519 | 89 | 32 | 13 |
| 30 | 237 | 24 | 15 | 12 |
| 50 | 74 | 14 | 12 | 12 |
| 70 | 35 | 12 | 12 | 12 |
| 90 | 24 | 12 | 12 | 12 |

(12C)

m=100000

| k \ α | 2 | 3 | 4 | 6 |
|---|---|---|---|---|
| 10 | 1,402 | 104 | 37 | 14 |
| 30 | 239 | 31 | 12 | 11 |
| 50 | 92 | 17 | 11 | 11 |
| 70 | 52 | 11 | 11 | 11 |
| 90 | 26 | 11 | 11 | 11 |

FIG. 15
(15A)
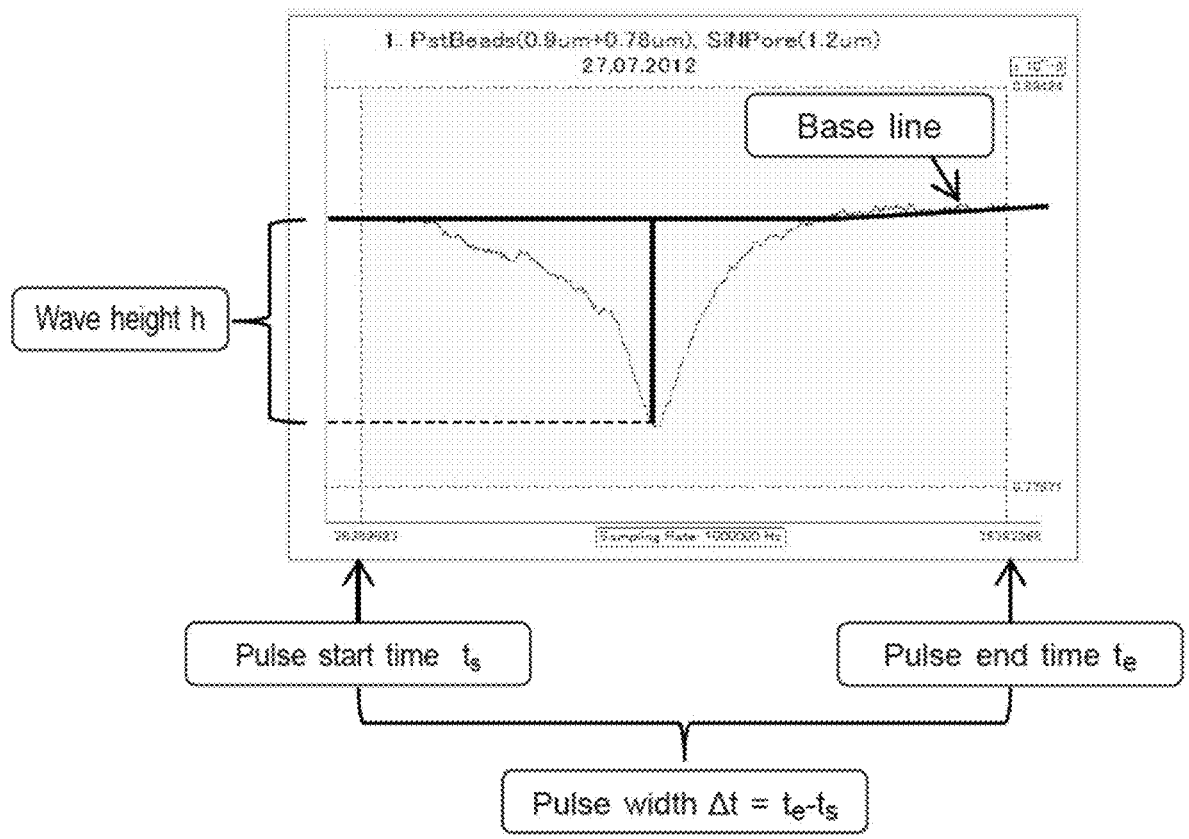
(15B)
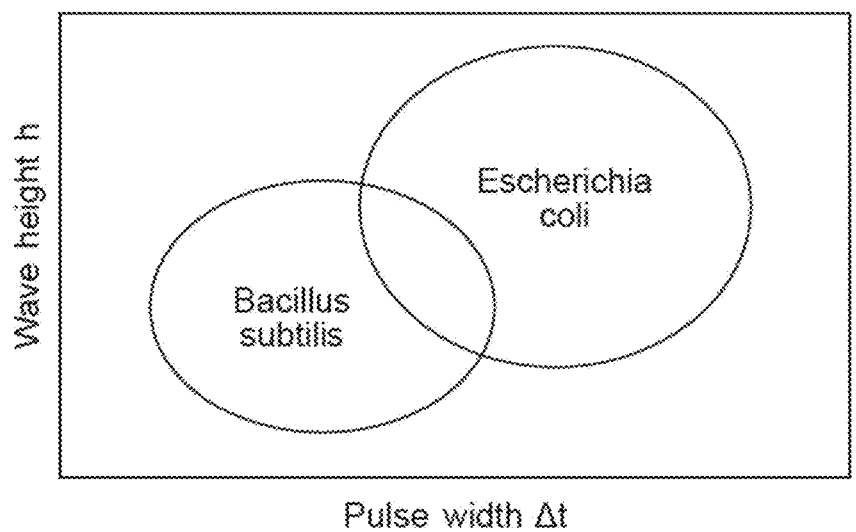

FIG. 18

<Derivation process of equation 17>

Constrained logarithmic likelihood maximization formula is differentiated and put zero.

$$\frac{\partial}{\partial n_i}\left[\sum_{x_j \in D} \log \sum_{l=1}^{k} n_l p_l(x_j) - \lambda\left(\sum_{l=1}^{k} n_l - N\right)\right] = 0$$

Then the following is obtained.

$$\sum_{x_j \in D} \frac{p_i(x_j)}{\sum_{l=1}^{k} n_l p_l(x_j)} = \lambda$$

Here undetermined multiplier λ becomes a problem, but it is found that λ = 1.

$$\lambda = \frac{1}{N}\sum_{i=1}^{k} n_i \lambda = \frac{1}{N}\sum_{x_j \in D}\sum_{i=1}^{k} \frac{n_i p_i(x_j)}{\sum_{l=1}^{k} n_l p_l(x_j)} = 1$$

Fig. 23
(23A) Setting of initial values
$$n_i^{(0)} = \frac{N}{k}$$
(23B) Iterative operation
$$n_i^{(1)} = n_i^{(0)} \sum_{x_j \in D} \frac{p_i(x_j)}{\sum_{l=1}^{k} n_l^{(0)} p_l(x_j)}$$
$$n_i^{(2)} = n_i^{(1)} \sum_{x_j \in D} \frac{p_i(x_j)}{\sum_{l=1}^{k} n_l^{(1)} p_l(x_j)}$$
⋮
(23C) Convergence conditions
$$\max_i \left( \left| n_i^{(t)} - n_i^{(t-1)} \right| \right) \leq \alpha$$

FIG. 24
(24A)
(24B)
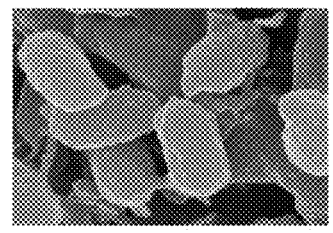
(24C)
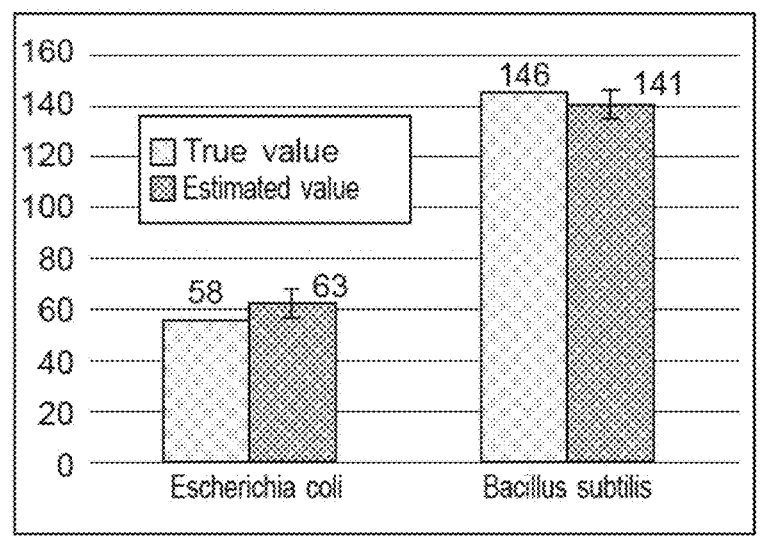
(24D)
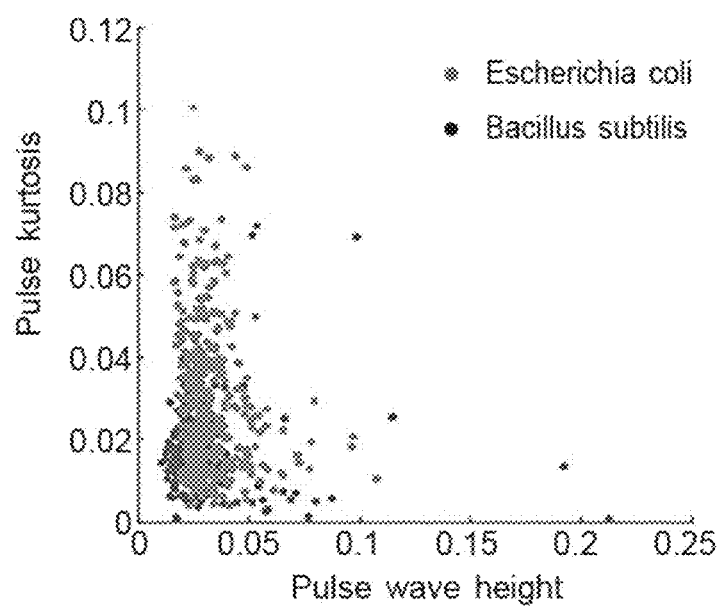

| Data of particle type distribution estimation target | Total number of particle | Number of Escherichia coli | | | Number of Bacillus subtilis | | | Weighted average | Averaged convergence | Averaged necessary |
|---|---|---|---|---|---|---|---|---|---|---|
| | | Truth | Estimation (average) | Standard deviation | Relative error | Truth | Estimation (average) | Standard deviation | Relative error | Relative error | step number | time(s) |
| Data mixing 10% E coli data to wave height data of 146 pieces of Bacillus subtilis | 161 | 15 | 50.45 | 11.92 | 2.36 | 146 | 110.55 | 11.92 | 0.24 | 0.44 | 12.3 | 2.16 |
| Data mixing 20% E coli data to wave height data of 146 pieces of Bacillus subtilis | 175 | 29 | 58.48 | 12.13 | 1.02 | 146 | 116.52 | 12.13 | 0.20 | 0.34 | 12.3 | 2.37 |
| Data mixing 30% E coli data to wave height data of 146 pieces of Bacillus subtilis | 190 | 44 | 73.20 | 13.45 | 0.66 | 146 | 116.80 | 13.45 | 0.20 | 0.31 | 13.6 | 2.21 |
| Data mixing 35% E coli data to wave height data of 146 pieces of Bacillus subtilis | 197 | 51 | 76.93 | 13.89 | 0.51 | 146 | 120.07 | 13.89 | 0.18 | 0.26 | 10.7 | 2.35 |
| Data mixing 40% E coli data to wave height data of 146 pieces of Bacillus subtilis | 204 | 58 | 79.23 | 14.52 | 0.37 | 146 | 124.77 | 14.52 | 0.15 | 0.21 | 11.1 | 2.47 |
| Data mixing 45% E coli data to wave height data of 146 pieces of Bacillus subtilis | 212 | 66 | 82.60 | 15.06 | 0.25 | 146 | 129.40 | 15.06 | 0.11 | 0.16 | 11.5 | 2.69 |
| Data mixing 50% E coli data to wave height data of 146 pieces of Bacillus subtilis | 219 | 73 | 85.37 | 15.63 | 0.17 | 146 | 133.63 | 15.63 | 0.08 | 0.11 | 11.6 | 2.80 |

(25B)

| Data of particle type distribution estimation target | Total number of particle | Number of Escherichia coli | | | Number of Bacillus subtilis | | | Weighted average | Averaged convergence | Averaged necessary |
|---|---|---|---|---|---|---|---|---|---|---|
| | | Truth | Estimation (average) | Standard deviation | Relative error | Truth | Estimation (average) | Standard deviation | Relative error | Relative error | step number | time(s) |
| Data mixing 10% E coli data to wave height data of 146 pieces of Bacillus subtilis | 161 | 15 | 39.51 | 9.14 | 1.63 | 146 | 121.49 | 9.14 | 0.14 | 0.30 | 11.7 | 2.07 |
| Data mixing 20% E coli data to wave height data of 146 pieces of Bacillus subtilis | 175 | 29 | 46.00 | 9.59 | 0.59 | 146 | 129.00 | 9.59 | 0.09 | 0.19 | 11.7 | 2.25 |
| Data mixing 30% E coli data to wave height data of 146 pieces of Bacillus subtilis | 190 | 44 | 55.40 | 10.29 | 0.26 | 146 | 134.60 | 10.29 | 0.12 | 0.12 | 11.7 | 2.43 |
| Data mixing 35% E coli data to wave height data of 146 pieces of Bacillus subtilis | 197 | 51 | 58.38 | 10.53 | 0.14 | 146 | 138.62 | 10.53 | 0.07 | 0.07 | 11.7 | 2.53 |
| Data mixing 40% E coli data to wave height data of 146 pieces of Bacillus subtilis | 204 | 58 | 61.09 | 11.07 | 0.05 | 146 | 142.91 | 11.07 | 0.03 | 0.03 | 11.9 | 2.67 |
| Data mixing 45% E coli data to wave height data of 146 pieces of Bacillus subtilis | 212 | 66 | 63.18 | 11.35 | 0.04 | 146 | 148.82 | 11.35 | 0.03 | 0.03 | 12.1 | 2.83 |
| Data mixing 50% E coli data to wave height data of 146 pieces of Bacillus subtilis | 219 | 73 | 65.69 | 12.15 | 0.10 | 146 | 153.31 | 12.15 | 0.07 | 0.07 | 12.3 | 2.96 |

| Data of particle type distribution estimation target | Total number of particles | Number of Escherichia coli | | | Number of Bacillus subtilis | | | Weighted average Relative error | Averaged convergence step number | Averaged necessary time(s) |
|---|---|---|---|---|---|---|---|---|---|---|
| | | Truth | Estimation (average) | Standard deviation | Relative error | Truth | Estimation (average) | Standard deviation | Relative error | | | |

| Data of particle type distribution estimation target | Total number of particles | Truth | Estimation (average) | Standard deviation | Relative error | Truth | Estimation (average) | Standard deviation | Relative error | Relative error | convergence step number | necessary time(s) |
|---|---|---|---|---|---|---|---|---|---|---|---|---|
| Data mixing 10% E coli data to wave height data of 146 pieces of Bacillus subtilis | 161 | 15 | 24.60 | 9.27 | 0.64 | 146 | 136.40 | 9.27 | 0.07 | 0.12 | 13.3 | 2.38 |
| Data mixing 20% E coli data to wave height data of 146 pieces of Bacillus subtilis | 175 | 29 | 31.99 | 10.26 | 0.10 | 146 | 143.01 | 10.26 | 0.02 | 0.03 | 12.8 | 2.49 |
| Data mixing 30% E coli data to wave height data of 146 pieces of Bacillus subtilis | 190 | 44 | 40.34 | 11.18 | 0.08 | 146 | 149.66 | 11.18 | 0.03 | 0.04 | 12.6 | 2.65 |
| Data mixing 35% E coli data to wave height data of 146 pieces of Bacillus subtilis | 197 | 51 | 44.45 | 11.72 | 0.13 | 146 | 152.55 | 11.72 | 0.04 | 0.07 | 12.6 | 2.77 |
| Data mixing 40% E coli data to wave height data of 146 pieces of Bacillus subtilis | 204 | 58 | 47.87 | 12.44 | 0.17 | 146 | 156.13 | 12.44 | 0.07 | 0.10 | 12.8 | 2.88 |
| Data mixing 45% E coli data to wave height data of 146 pieces of Bacillus subtilis | 212 | 66 | 51.01 | 13.36 | 0.23 | 146 | 160.99 | 13.36 | 0.10 | 0.14 | 13.1 | 3.05 |
| Data mixing 50% E coli data to wave height data of 146 pieces of Bacillus subtilis | 219 | 73 | 54.81 | 13.85 | 0.25 | 146 | 164.19 | 13.85 | 0.12 | 0.17 | 13 | 3.15 |

(26B)

| Data of particle type distribution estimation target | Total number of particles | Truth | Estimation (average) | Standard deviation | Relative error | Truth | Estimation (average) | Standard deviation | Relative error | Relative error | convergence step number | necessary time(s) |
|---|---|---|---|---|---|---|---|---|---|---|---|---|
| Data mixing 10% E coli data to wave height data of 146 pieces of Bacillus subtilis | 161 | 15 | 24.45 | 7.53 | 0.63 | 146 | 136.55 | 7.53 | 0.06 | 0.12 | 11.6 | 2.07 |
| Data mixing 20% E coli data to wave height data of 146 pieces of Bacillus subtilis | 175 | 29 | 34.62 | 8.25 | 0.19 | 146 | 140.38 | 8.25 | 0.04 | 0.06 | 11 | 0.13 |
| Data mixing 30% E coli data to wave height data of 146 pieces of Bacillus subtilis | 190 | 44 | 53.22 | 8.83 | 0.21 | 146 | 136.78 | 8.83 | 0.06 | 0.10 | 9.6 | 2.03 |
| Data mixing 35% E coli data to wave height data of 146 pieces of Bacillus subtilis | 197 | 51 | 58.13 | 9.50 | 0.14 | 146 | 138.87 | 9.50 | 0.05 | 0.07 | 9.6 | 2.13 |
| Data mixing 40% E coli data to wave height data of 146 pieces of Bacillus subtilis | 204 | 58 | 62.63 | 9.95 | 0.08 | 146 | 141.37 | 9.95 | 0.03 | 0.05 | 9.7 | 2.18 |
| Data mixing 45% E coli data to wave height data of 146 pieces of Bacillus subtilis | 212 | 66 | 65.61 | 10.64 | 0.01 | 146 | 146.39 | 10.64 | 0.00 | 0.00 | 9.9 | 2.32 |
| Data mixing 50% E coli data to wave height data of 146 pieces of Bacillus subtilis | 219 | 73 | 68.26 | 10.95 | 0.06 | 146 | 150.74 | 10.95 | 0.03 | 0.04 | 9.9 | 2.40 |

| Data of particle type distribution estimation target | Total number of particle | Number of Escherichia coli | | | | Number of Bacillus subtilis | | | | Weighted average | Averaged convergence step number | Averaged necessary time(s) |
|---|---|---|---|---|---|---|---|---|---|---|---|---|
| | | Truth | Estimation (average) | Standard deviation | Relative error | Truth | Estimation (average) | Standard deviation | Relative error | Relative error | | |
| Data mixing 10% E coli data to wave height data of 146 pieces of Bacillus subtilis | 161 | 15 | 24.45 | 7.53 | 0.63 | 146 | 136.55 | 7.53 | 0.06 | 0.12 | 11.6 | 2.07 |
| Data mixing 20% E coli data to wave height data of 146 pieces of Bacillus subtilis | 175 | 29 | 34.52 | 8.25 | 0.19 | 146 | 140.38 | 8.25 | 0.04 | 0.06 | 11.9 | 2.13 |
| Data mixing 30% E coli data to wave height data of 146 pieces of Bacillus subtilis | 190 | 44 | 53.22 | 8.83 | 0.21 | 146 | 136.78 | 8.83 | 0.06 | 0.10 | 9.6 | 2.03 |
| Data mixing 35% E coli data to wave height data of 146 pieces of Bacillus subtilis | 197 | 51 | 58.13 | 9.50 | 0.14 | 146 | 138.87 | 9.50 | 0.05 | 0.07 | 9.6 | 2.13 |
| Data mixing 40% E coli data to wave height data of 146 pieces of Bacillus subtilis | 204 | 58 | 62.63 | 9.95 | 0.08 | 146 | 141.37 | 9.95 | 0.03 | 0.05 | 9.7 | 2.18 |
| Data mixing 45% E coli data to wave height data of 146 pieces of Bacillus subtilis | 212 | 66 | 65.61 | 10.64 | 0.01 | 146 | 146.39 | 10.64 | 0.00 | 0.00 | 9.9 | 2.32 |
| Data mixing 50% E coli data to wave height data of 146 pieces of Bacillus subtilis | 219 | 73 | 68.26 | 10.95 | 0.06 | 146 | 150.74 | 10.95 | 0.03 | 0.04 | 9.9 | 2.40 |

(27B)

$$\text{Weighted average relative error} = \sum_{i=1}^{k}\left(\frac{n_i}{N}\cdot\frac{|n_i - \hat{n}_i|}{n_i}\right) = \sum_{i=1}^{k}\frac{|n_i - \hat{n}_i|}{N}$$

Error 4~12%

| Data of particle type distribution estimation target | Total number of particle | Number of Escherichia coli | | | Number of Bacillus subtilis | | | Weighted average Relative error | Averaged convergence step number | Averaged necessary time(s) |
|---|---|---|---|---|---|---|---|---|---|---|
| | | Truth | Estimation (average) | Standard deviation | Relative error | Truth | Estimation (average) | Standard deviation | Relative error | | | |

| Data of particle type distribution estimation target | Total number of particle | Truth | Estimation (average) | Standard deviation | Relative error | Truth | Estimation (average) | Standard deviation | Relative error | Weighted average Relative error | Averaged convergence step number | Averaged necessary time(s) |
|---|---|---|---|---|---|---|---|---|---|---|---|---|
| Data mixing 10% E coli data to wave height data of 146 pieces of Bacillus subtilis | 161 | 15 | 50.45 | 11.92 | 2.36 | 146 | 110.55 | 11.92 | 0.24 | 0.44 | 12.3 | 2.18 |
| Data mixing 20% E coli data to wave height data of 146 pieces of Bacillus subtilis | 175 | 29 | 58.48 | 12.13 | 1.02 | 146 | 116.52 | 12.13 | 0.20 | 0.34 | 12.3 | 2.37 |
| Data mixing 30% E coli data to wave height data of 146 pieces of Bacillus subtilis | 190 | 44 | 73.20 | 13.45 | 0.66 | 146 | 116.80 | 13.45 | 0.20 | 0.31 | 10.6 | 2.21 |
| Data mixing 35% E coli data to wave height data of 146 pieces of Bacillus subtilis | 197 | 51 | 76.93 | 13.89 | 0.51 | 146 | 120.07 | 13.89 | 0.18 | 0.26 | 10.7 | 2.35 |
| Data mixing 40% E coli data to wave height data of 146 pieces of Bacillus subtilis | 204 | 58 | 79.23 | 14.52 | 0.37 | 146 | 124.77 | 14.52 | 0.15 | 0.21 | 11.1 | 2.47 |
| Data mixing 45% E coli data to wave height data of 146 pieces of Bacillus subtilis | 212 | 66 | 82.50 | 15.06 | 0.25 | 146 | 129.40 | 15.06 | 0.11 | 0.16 | 11.5 | 2.69 |
| Data mixing 50% E coli data to wave height data of 146 pieces of Bacillus subtilis | 219 | 73 | 85.37 | 15.63 | 0.17 | 146 | 133.63 | 15.63 | 0.08 | 0.11 | 11.6 | 2.80 |

(28B)

| Data of particle type distribution estimation target | Total number of particle | Truth | Estimation (average) | Standard deviation | Relative error | Truth | Estimation (average) | Standard deviation | Relative error | Weighted average Relative error | Averaged convergence step number | Averaged necessary time(s) |
|---|---|---|---|---|---|---|---|---|---|---|---|---|
| Data mixing 10% E coli data to wave height data of 146 pieces of Bacillus subtilis | 161 | 15 | 39.51 | 9.14 | 1.63 | 146 | 121.49 | 9.14 | 0.17 | 0.30 | 11.7 | 2.07 |
| Data mixing 20% E coli data to wave height data of 146 pieces of Bacillus subtilis | 175 | 29 | 46.09 | 9.59 | 0.59 | 146 | 129.00 | 9.59 | 0.12 | 0.19 | 11.7 | 2.25 |
| Data mixing 30% E coli data to wave height data of 146 pieces of Bacillus subtilis | 190 | 44 | 55.40 | 10.29 | 0.26 | 146 | 134.60 | 10.29 | 0.08 | 0.12 | 11.7 | 2.43 |
| Data mixing 35% E coli data to wave height data of 146 pieces of Bacillus subtilis | 197 | 51 | 58.38 | 10.53 | 0.14 | 146 | 138.62 | 10.53 | 0.05 | 0.07 | 11.7 | 2.53 |
| Data mixing 40% E coli data to wave height data of 146 pieces of Bacillus subtilis | 204 | 58 | 61.09 | 11.07 | 0.05 | 146 | 142.91 | 11.07 | 0.02 | 0.03 | 11.9 | 2.67 |
| Data mixing 45% E coli data to wave height data of 146 pieces of Bacillus subtilis | 212 | 66 | 63.19 | 11.35 | 0.04 | 146 | 148.82 | 11.35 | 0.02 | 0.03 | 12.1 | 2.83 |
| Data mixing 50% E coli data to wave height data of 146 pieces of Bacillus subtilis | 219 | 73 | 65.69 | 12.15 | 0.10 | 146 | 153.31 | 12.15 | 0.05 | 0.07 | 12.3 | 2.95 |

FIG. 29
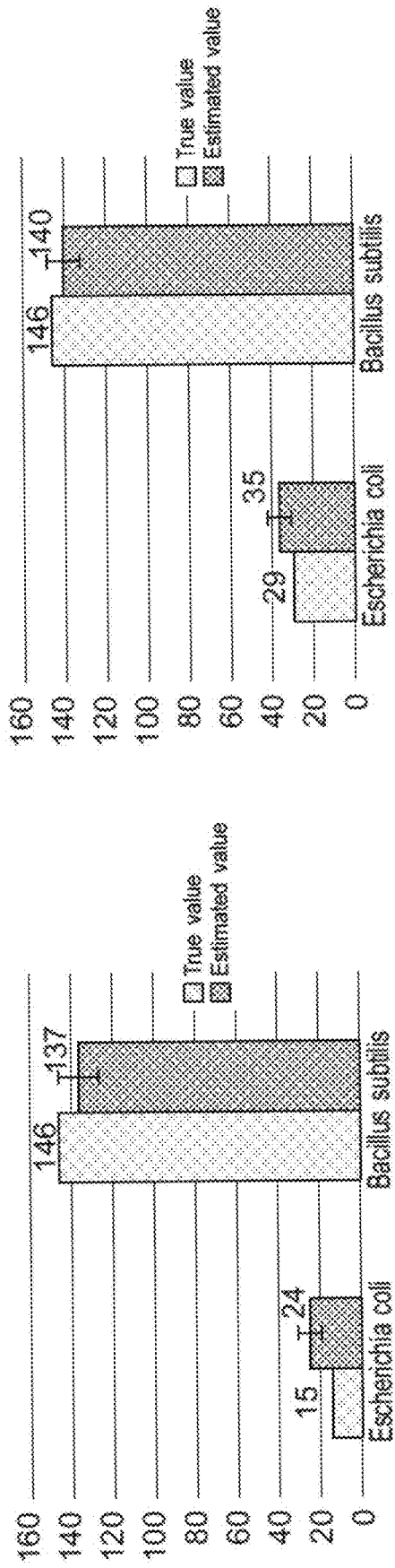
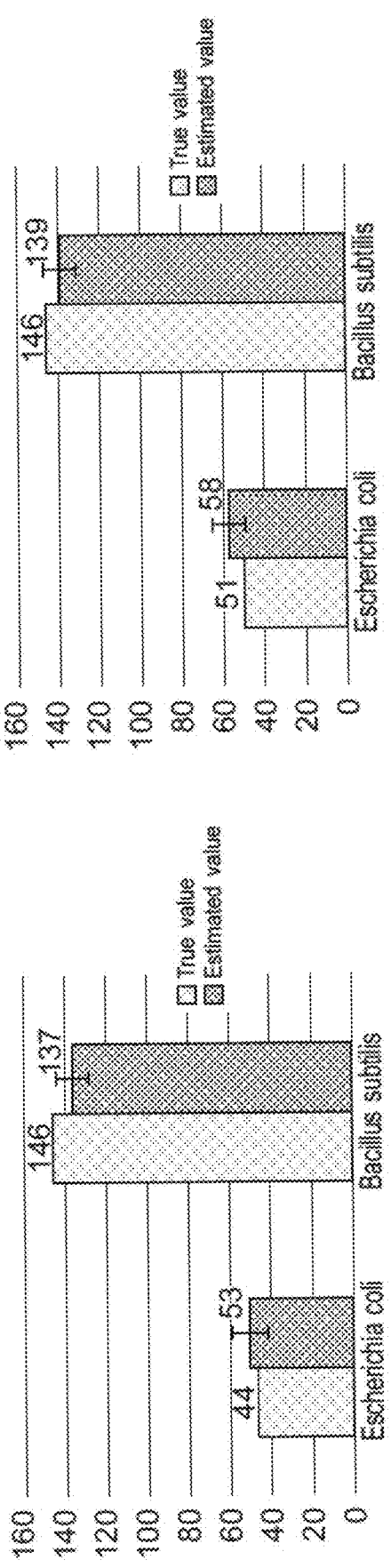

FIG. 30
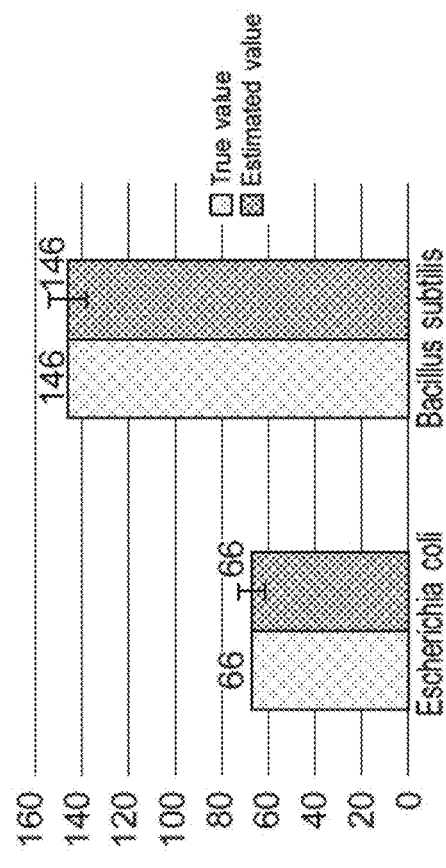
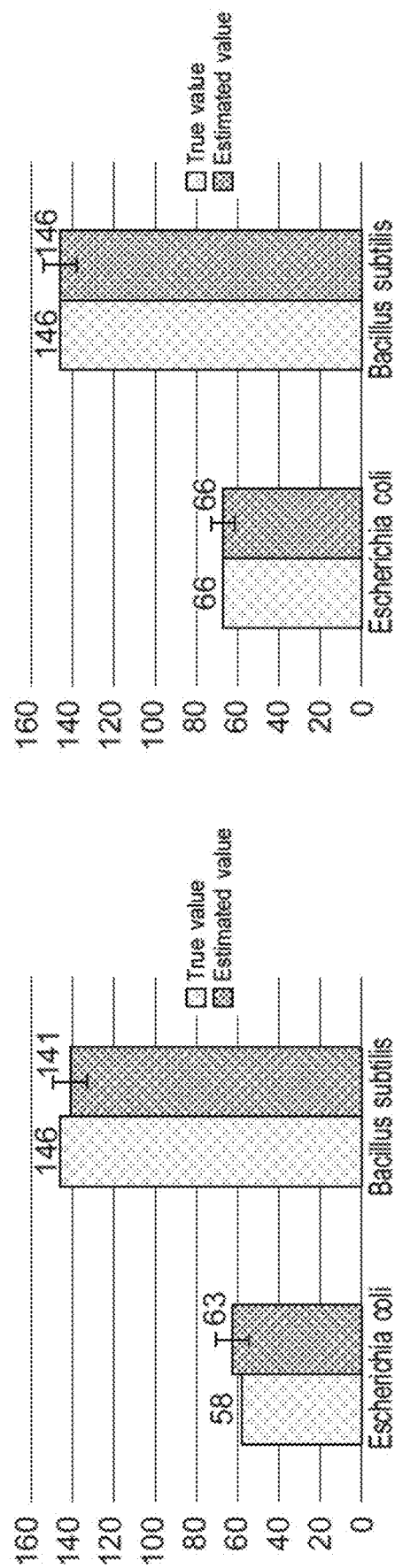
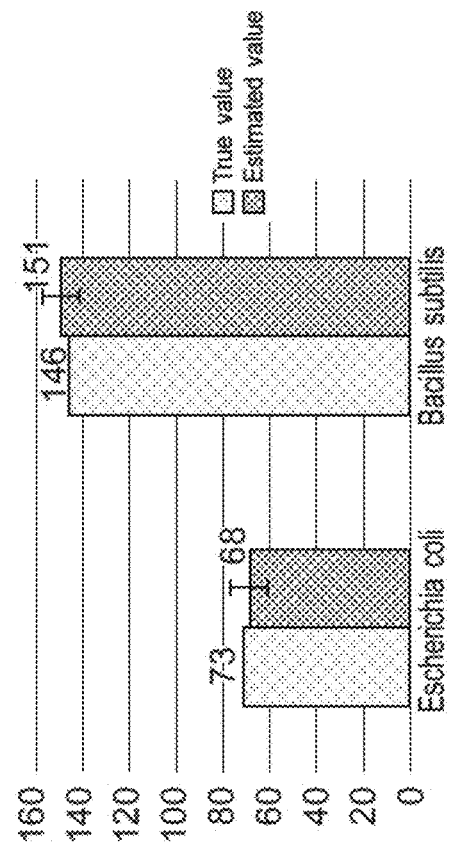

Fig. 31
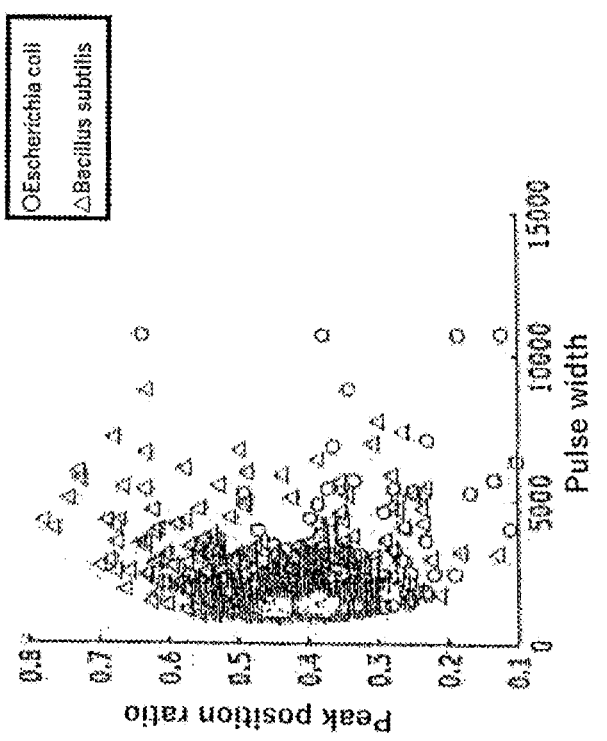
② Pulse length Δt, Peak position ratio r
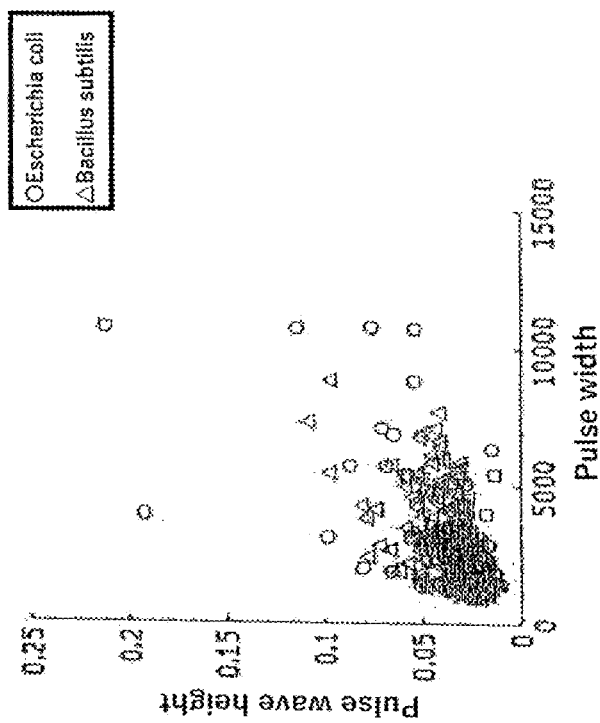
① Pulse length Δt, Wave height |h|

Fig. 34
(34A)
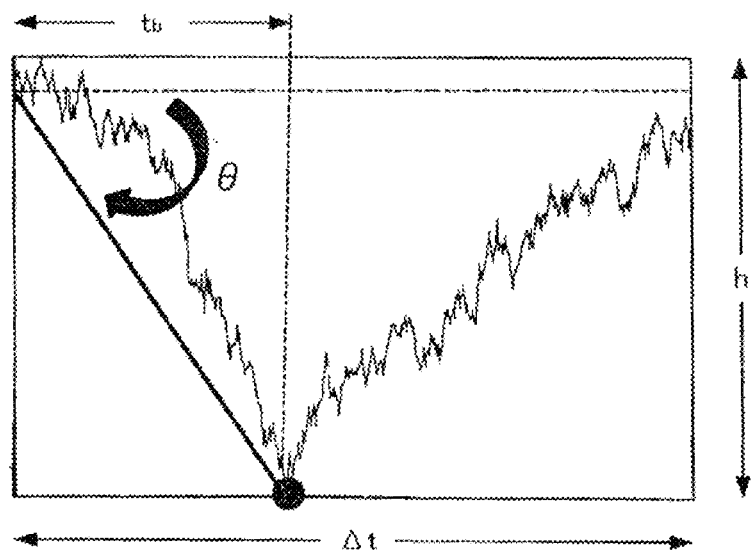
(34B)
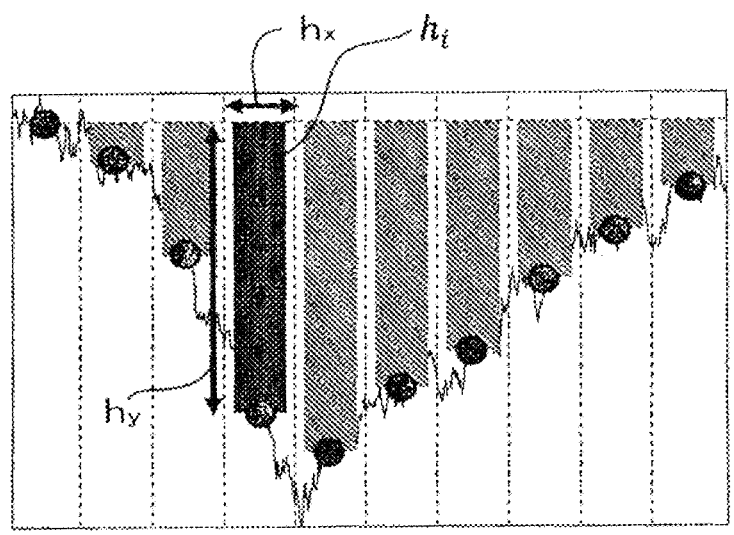

Fig. 37
(37A)
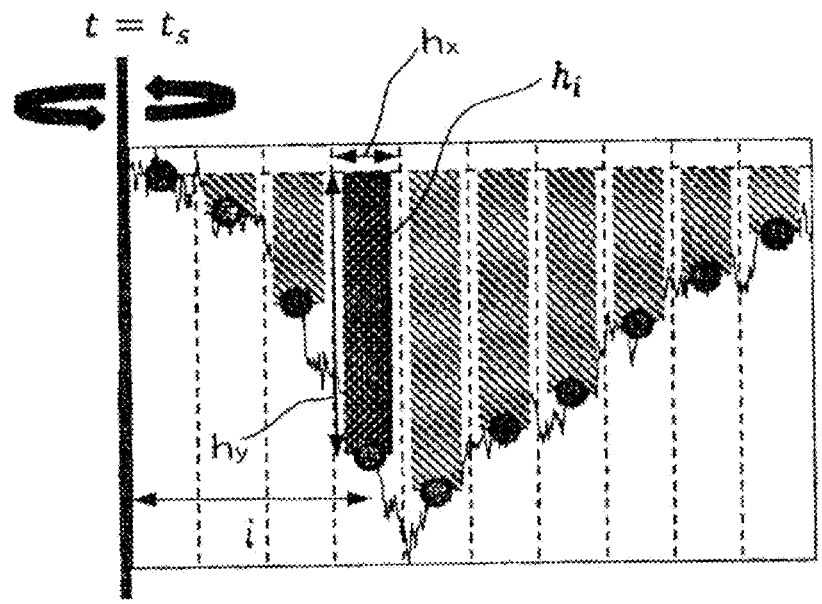
(37B)
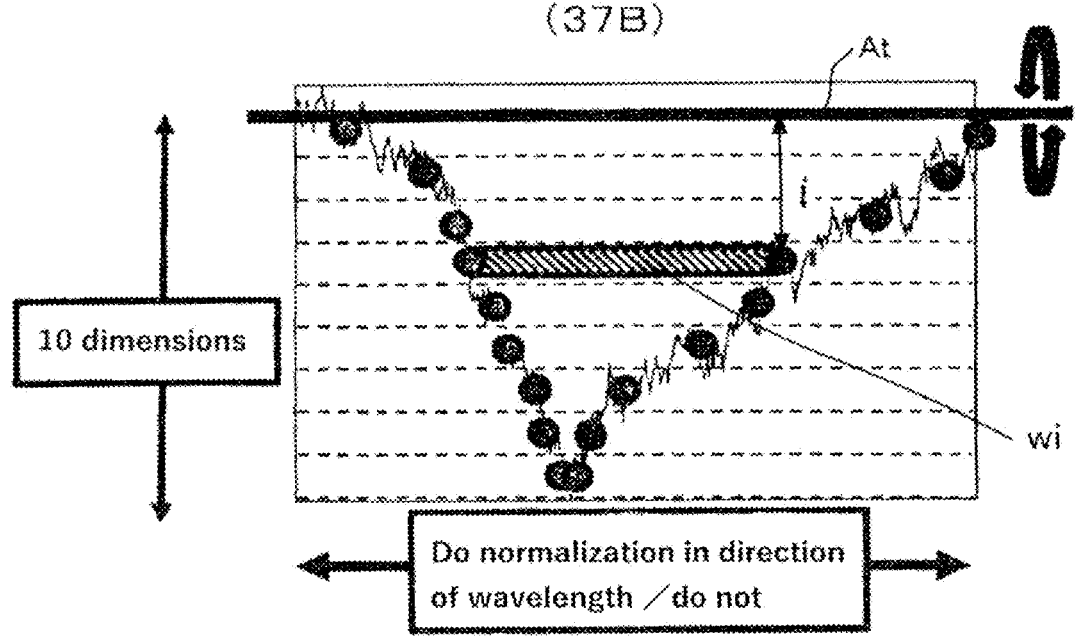

Fig. 38
(38A)
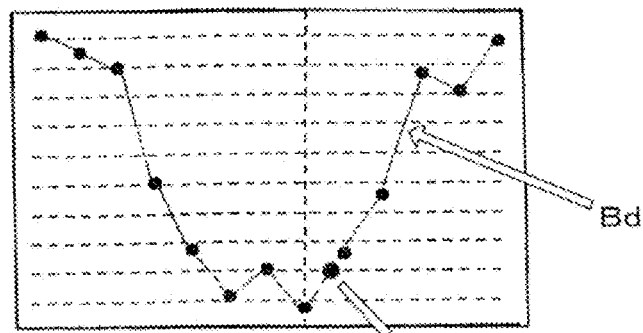
(38B)
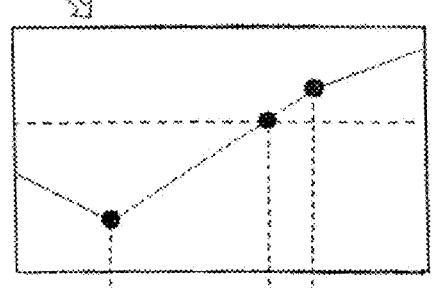
(38C)
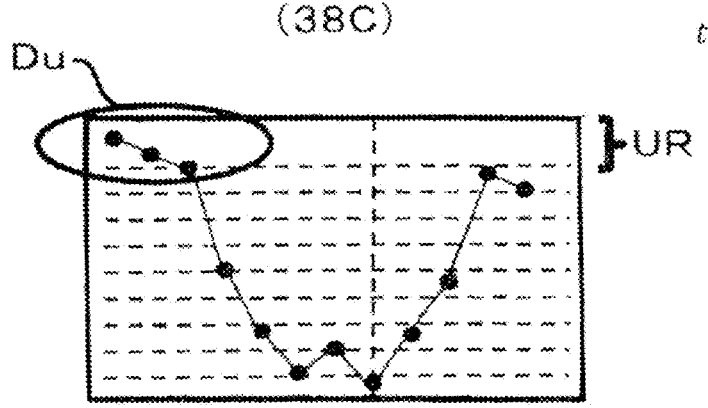

Fig. 39
(39A)
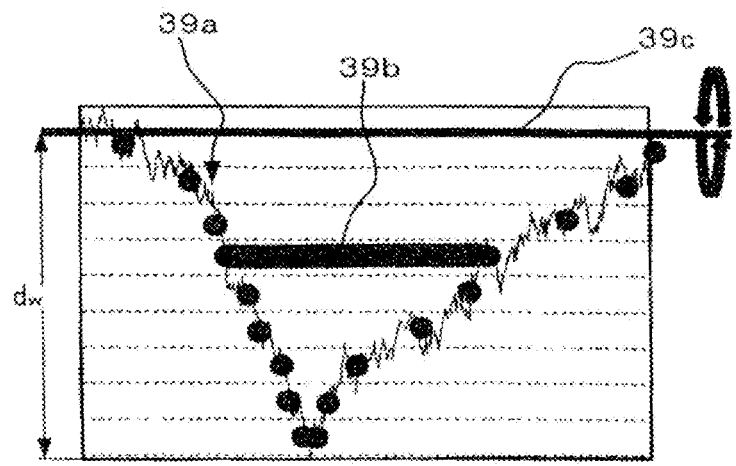
(39B)
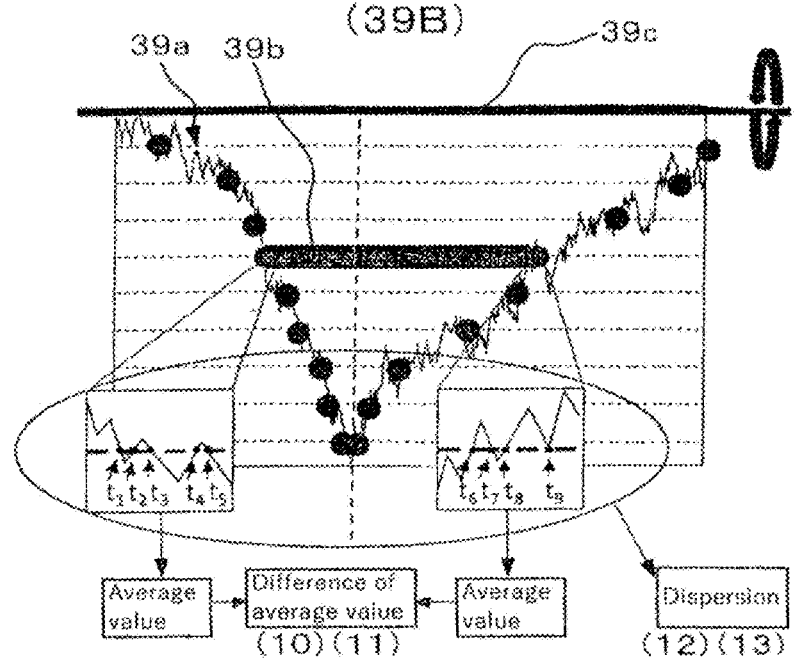

| | Wave length Δt | Wave height {h} | Peak position ratio r | Kurtosis k | Area ratio r_m | Depression θ | Area m | Inertia i | Inertia I (normalization) | Inertia I_w | Inertia I_wv | Inertia I_w (normalization) | Inertia I_wv (normalization) |
|---|---|---|---|---|---|---|---|---|---|---|---|---|---|
| Wave length Δt | | 0.238 | 0.131 | 0.120 | 0.141 | 0.151 | 0.106 | 0.102 | 0.151 | 0.108 | 0.251 | 0.106 | 0.130 |
| | | (0.132) | (0.086) | (0.080) | (0.097) | (0.097) | (0.082) | (0.086) | (0.069) | (0.082) | (0.132) | (0.082) | (0.092) |
| Wave height {h} | | | 0.157 | 0.106 | 0.173 | 0.186 | 0.166 | 0.138 | 0.126 | 0.231 | 0.147 | 0.122 | 0.097 |
| | | | (0.100) | (0.085) | (0.108) | (0.109) | (0.110) | (0.118) | (0.085) | (0.154) | (0.098) | (0.087) | (0.072) |
| Peak position ratio r | | | | 0.110 | 0.134 | 0.272 | 0.121 | 0.100 | 0.113 | 0.129 | 0.154 | 0.116 | 0.156 |
| | | | | (0.077) | (0.104) | (0.210) | (0.081) | (0.066) | (0.071) | (0.086) | (0.095) | (0.075) | (0.089) |
| Kurtosis k | | | | | 0.164 | 0.118 | 0.095 | 0.106 | 0.131 | 0.164 | 0.194 | 0.141 | 0.156 |
| | | | | | (0.083) | (0.074) | (0.070) | (0.078) | (0.086) | (0.100) | (0.121) | (0.090) | (0.089) |
| Area ratio r_m | | | | | | 0.144 | 0.112 | 0.100 | 0.124 | 0.129 | 0.180 | 0.148 | 0.162 |
| | | | | | | (0.098) | (0.089) | (0.070) | (0.076) | (0.094) | (0.115) | (0.093) | (0.088) |
| Depression θ | | | | | | | 0.134 | 0.104 | 0.118 | 0.119 | 0.146 | 0.116 | 0.135 |
| | | | | | | | (0.092) | (0.077) | (0.079) | (0.085) | (0.101) | (0.085) | (0.080) |
| Area m | | | | | | | | 0.098 | 0.136 | 0.138 | 0.130 | 0.107 | 0.107 |
| | | | | | | | | (0.071) | (0.095) | (0.108) | (0.096) | (0.076) | (0.083) |
| Inertia i | | | | | | | | | 0.120 | 0.102 | 0.107 | 0.112 | 0.106 |
| | | | | | | | | | (0.089) | (0.079) | (0.070) | (0.088) | (0.074) |
| Inertia I (normalization) | | | | | | | | | | 0.115 | 0.164 | 0.121 | 0.124 |
| | | | | | | | | | | (0.079) | (0.116) | (0.074) | (0.075) |
| Inertia I_w | | | | | | | | | | | 0.468 | 0.101 | 0.136 |
| | | | | | | | | | | | (0.156) | (0.068) | (0.096) |
| Inertia I_wv | | | | | | | | | | | | 0.213 | 0.221 |
| | | | | | | | | | | | | (0.107) | (0.111) |
| Inertia I_w (normalization) | | | | | | | | | | | | | 0.143 |
| | | | | | | | | | | | | | (0.091) |
| Inertia I_wv (normalization) | | | | | | | | | | | | | |

(42B)

| | Wave length Δt | Wave height {h} | Peak position ratio r | Kurtosis k | Area ratio r_m | Depression θ | Area m | Inertia i | Inertia I (normalization) | Inertia I_w | Inertia I_wv | Inertia I_w (normalization) | Inertia I_wv (normalization) |
|---|---|---|---|---|---|---|---|---|---|---|---|---|---|
| Wave length Δt | | 0.183 | 0.147 | 0.137 | 0.152 | 0.142 | 0.098 | 0.091 | 0.137 | 0.114 | 0.372 | 0.122 | 0.133 |
| | | (0.115) | (0.096) | (0.083) | (0.093) | (0.096) | (0.061) | (0.062) | (0.079) | (0.085) | (0.109) | (0.081) | (0.076) |
| Wave height {h} | | | 0.140 | 0.107 | 0.130 | 0.143 | 0.164 | 0.125 | 0.137 | 0.123 | 0.221 | 0.108 | 0.109 |
| | | | (0.091) | (0.070) | (0.087) | (0.089) | (0.114) | (0.094) | (0.088) | (0.077) | (0.104) | (0.074) | (0.078) |
| Peak position ratio r | | | | 0.138 | 0.151 | 0.346 | 0.114 | 0.093 | 0.105 | 0.152 | 0.146 | 0.139 | 0.154 |
| | | | | (0.070) | (0.089) | (0.183) | (0.085) | (0.059) | (0.063) | (0.093) | (0.094) | (0.078) | (0.076) |
| Kurtosis k | | | | | 0.170 | 0.137 | 0.110 | 0.106 | 0.152 | 0.224 | 0.164 | 0.175 | 0.167 |
| | | | | | (0.085) | (0.077) | (0.066) | (0.066) | (0.088) | (0.101) | (0.096) | (0.093) | (0.087) |
| Area ratio r_m | | | | | | 0.170 | 0.098 | 0.097 | 0.131 | 0.145 | 0.145 | 0.179 | 0.162 |
| | | | | | | (0.106) | (0.062) | (0.063) | (0.077) | (0.085) | (0.081) | (0.071) | (0.068) |
| Depression θ | | | | | | | 0.116 | 0.104 | 0.113 | 0.160 | 0.161 | 0.141 | 0.142 |
| | | | | | | | (0.084) | (0.073) | (0.070) | (0.095) | (0.098) | (0.079) | (0.067) |
| Area m | | | | | | | | 0.106 | 0.119 | 0.108 | 0.175 | 0.118 | 0.128 |
| | | | | | | | | (0.064) | (0.085) | (0.073) | (0.104) | (0.068) | (0.075) |
| Inertia i | | | | | | | | | 0.099 | 0.105 | 0.144 | 0.113 | 0.111 |
| | | | | | | | | | (0.064) | (0.080) | (0.095) | (0.070) | (0.066) |
| Inertia I (normalization) | | | | | | | | | | 0.136 | 0.139 | 0.127 | 0.140 |
| | | | | | | | | | | (0.091) | (0.082) | (0.078) | (0.073) |
| Inertia I_w | | | | | | | | | | | 0.659 | 0.137 | 0.169 |
| | | | | | | | | | | | (0.151) | (0.074) | (0.088) |
| Inertia I_wv | | | | | | | | | | | | 0.154 | 0.161 |
| | | | | | | | | | | | | (0.090) | (0.083) |
| Inertia I_w (normalization) | | | | | | | | | | | | | 0.159 |
| | | | | | | | | | | | | | (0.103) |
| Inertia I_wv (normalization) | | | | | | | | | | | | | |

| | Wave length Δt | Wave height |h| | Peak position ratio r | Kurtosis k | Area ratio r_m | Depression θ | Area m | Inertia i | Inertia I (normalization) | Inertia I_w | Inertia I_wv | Inertia I_w (normalization) | Inertia I_wv (normalization) |
|---|---|---|---|---|---|---|---|---|---|---|---|---|---|
| Wave length Δt | | 0.181 | 0.141 | 0.137 | 0.149 | 0.135 | 0.100 | 0.093 | 0.122 | 0.120 | 0.393 | 0.124 | 0.144 |
| | | (0.131) | (0.091) | (0.089) | (0.092) | (0.080) | (0.066) | (0.072) | (0.074) | (0.084) | (0.134) | (0.075) | (0.095) |
| Wave height |h| | | | 0.130 | 0.118 | 0.126 | 0.129 | 0.138 | 0.116 | 0.138 | 0.114 | 0.225 | 0.100 | 0.101 |
| | | | (0.095) | (0.086) | (0.086) | (0.094) | (0.101) | (0.081) | (0.098) | (0.082) | (0.114) | (0.067) | (0.075) |
| Peak position ratio r | | | | 0.144 | 0.159 | 0.388 | 0.113 | 0.100 | 0.119 | 0.164 | 0.144 | 0.164 | 0.144 |
| | | | | (0.077) | (0.102) | (0.192) | (0.085) | (0.075) | (0.076) | (0.093) | (0.093) | (0.080) | (0.080) |
| Kurtosis k | | | | | 0.174 | 0.153 | 0.111 | 0.116 | 0.147 | 0.188 | 0.174 | 0.172 | 0.173 |
| | | | | | (0.086) | (0.091) | (0.077) | (0.070) | (0.084) | (0.108) | (0.108) | (0.097) | (0.090) |
| Area ratio r_m | | | | | | 0.177 | 0.099 | 0.111 | 0.144 | 0.157 | 0.160 | 0.193 | 0.168 |
| | | | | | | (0.109) | (0.063) | (0.079) | (0.073) | (0.103) | (0.106) | (0.079) | (0.081) |
| Depression θ | | | | | | | 0.107 | 0.095 | 0.114 | 0.157 | 0.176 | 0.139 | 0.144 |
| | | | | | | | (0.072) | (0.066) | (0.061) | (0.091) | (0.094) | (0.080) | (0.079) |
| Area m | | | | | | | | 0.095 | 0.105 | 0.102 | 0.147 | 0.116 | 0.124 |
| | | | | | | | | (0.062) | (0.073) | (0.072) | (0.117) | (0.076) | (0.074) |
| Inertia i | | | | | | | | | 0.101 | 0.106 | 0.144 | 0.110 | 0.116 |
| | | | | | | | | | (0.076) | (0.076) | (0.110) | (0.073) | (0.075) |
| Inertia I (normalization) | | | | | | | | | | 0.129 | 0.138 | 0.149 | 0.149 |
| | | | | | | | | | | (0.079) | (0.084) | (0.094) | (0.079) |
| Inertia I_w | | | | | | | | | | | 0.669 | 0.145 | 0.218 |
| | | | | | | | | | | | (0.135) | (0.084) | (0.091) |
| Inertia I_wv | | | | | | | | | | | | 0.171 | 0.172 |
| | | | | | | | | | | | | (0.091) | (0.099) |
| Inertia I_w (normalization) | | | | | | | | | | | | | 0.198 |
| | | | | | | | | | | | | | (0.092) |
| Inertia I_wv (normalization) | | | | | | | | | | | | | |

(43B)

| | Wave length Δt | Wave height |h| | Peak position ratio r | Kurtosis k | Area ratio r_m | Depression θ | Area m | Inertia i | Inertia I (normalization) | Inertia I_w | Inertia I_wv | Inertia I_w (normalization) | Inertia I_wv (normalization) |
|---|---|---|---|---|---|---|---|---|---|---|---|---|---|
| Wave length Δt | | 0.206 | 0.143 | 0.143 | 0.164 | 0.143 | 0.092 | 0.106 | 0.120 | 0.143 | 0.339 | 0.141 | 0.145 |
| | | (0.125) | (0.086) | (0.080) | (0.102) | (0.086) | (0.048) | (0.068) | (0.071) | (0.097) | (0.139) | (0.074) | (0.083) |
| Wave height |h| | | | 0.146 | 0.116 | 0.126 | 0.157 | 0.153 | 0.130 | 0.133 | 0.138 | 0.222 | 0.126 | 0.116 |
| | | | (0.089) | (0.070) | (0.074) | (0.090) | (0.093) | (0.075) | (0.093) | (0.086) | (0.129) | (0.073) | (0.068) |
| Peak position ratio r | | | | 0.196 | 0.220 | 0.393 | 0.121 | 0.122 | 0.136 | 0.161 | 0.162 | 0.172 | 0.159 |
| | | | | (0.086) | (0.104) | (0.188) | (0.073) | (0.073) | (0.073) | (0.089) | (0.082) | (0.091) | (0.070) |
| Kurtosis k | | | | | 0.212 | 0.169 | 0.138 | 0.117 | 0.178 | 0.227 | 0.140 | 0.198 | 0.177 |
| | | | | | (0.086) | (0.084) | (0.081) | (0.077) | (0.106) | (0.104) | (0.079) | (0.104) | (0.093) |
| Area ratio r_m | | | | | | 0.192 | 0.116 | 0.119 | 0.153 | 0.168 | 0.161 | 0.205 | 0.192 |
| | | | | | | (0.120) | (0.069) | (0.072) | (0.086) | (0.086) | (0.087) | (0.083) | (0.085) |
| Depression θ | | | | | | | 0.110 | 0.118 | 0.123 | 0.162 | 0.193 | 0.173 | 0.145 |
| | | | | | | | (0.059) | (0.065) | (0.071) | (0.092) | (0.102) | (0.085) | (0.080) |
| Area m | | | | | | | | 0.130 | 0.124 | 0.119 | 0.156 | 0.118 | 0.127 |
| | | | | | | | | (0.071) | (0.078) | (0.070) | (0.086) | (0.071) | (0.071) |
| Inertia i | | | | | | | | | 0.116 | 0.101 | 0.171 | 0.109 | 0.101 |
| | | | | | | | | | (0.065) | (0.058) | (0.104) | (0.063) | (0.056) |
| Inertia I (normalization) | | | | | | | | | | 0.133 | 0.169 | 0.146 | 0.139 |
| | | | | | | | | | | (0.077) | (0.096) | (0.080) | (0.074) |
| Inertia I_w | | | | | | | | | | | 0.672 | 0.160 | 0.191 |
| | | | | | | | | | | | (0.162) | (0.084) | (0.091) |
| Inertia I_wv | | | | | | | | | | | | 0.172 | 0.144 |
| | | | | | | | | | | | | (0.098) | (0.084) |
| Inertia I_w (normalization) | | | | | | | | | | | | | 0.155 |
| | | | | | | | | | | | | | (0.093) |
| Inertia I_wv (normalization) | | | | | | | | | | | | | |

| | Wave length Δt | Wave height \|h\| | Peak position ratio r | Kurtosis k | Area ratio r_m | Depression θ | Area m | Inertia i | Inertia I (normalization) | Inertia I_w | Inertia I_wv | Inertia I_w (normalization) | Inertia I_wv (normalization) |
|---|---|---|---|---|---|---|---|---|---|---|---|---|---|
| Wave length Δt | | 0.194 | 0.170 | 0.169 | 0.174 | 0.173 | 0.133 | 0.134 | 0.142 | 0.141 | 0.337 | 0.168 | 0.160 |
| | | (0.110) | (0.080) | (0.086) | (0.082) | (0.084) | (0.057) | (0.071) | (0.066) | (0.063) | (0.137) | (0.082) | (0.071) |
| Wave height \|h\| | | | 0.163 | 0.136 | 0.164 | 0.152 | 0.186 | 0.158 | 0.147 | 0.170 | 0.165 | 0.154 | 0.133 |
| | | | (0.082) | (0.056) | (0.078) | (0.070) | (0.116) | (0.087) | (0.093) | (0.090) | (0.085) | (0.068) | (0.057) |
| Peak position ratio r | | | | 0.170 | 0.220 | 0.469 | 0.133 | 0.145 | 0.158 | 0.189 | 0.214 | 0.206 | 0.179 |
| | | | | (0.082) | (0.106) | (0.216) | (0.058) | (0.072) | (0.072) | (0.095) | (0.118) | (0.080) | (0.073) |
| Kurtosis k | | | | | 0.240 | 0.185 | 0.153 | 0.139 | 0.197 | 0.215 | 0.247 | 0.215 | 0.183 |
| | | | | | (0.097) | (0.083) | (0.065) | (0.057) | (0.079) | (0.097) | (0.142) | (0.094) | (0.074) |
| Area ratio r_m | | | | | | 0.207 | 0.141 | 0.143 | 0.191 | 0.201 | 0.253 | 0.217 | 0.180 |
| | | | | | | (0.106) | (0.066) | (0.066) | (0.084) | (0.105) | (0.137) | (0.084) | (0.074) |
| Depression θ | | | | | | | 0.141 | 0.143 | 0.145 | 0.175 | 0.193 | 0.167 | 0.161 |
| | | | | | | | (0.058) | (0.062) | (0.059) | (0.084) | (0.113) | (0.062) | (0.072) |
| Area m | | | | | | | | 0.151 | 0.146 | 0.134 | 0.188 | 0.148 | 0.130 |
| | | | | | | | | (0.066) | (0.069) | (0.057) | (0.102) | (0.069) | (0.058) |
| Inertia i | | | | | | | | | 0.137 | 0.143 | 0.179 | 0.145 | 0.153 |
| | | | | | | | | | (0.058) | (0.066) | (0.090) | (0.061) | (0.071) |
| Inertia I (normalization) | | | | | | | | | | 0.146 | 0.200 | 0.189 | 0.170 |
| | | | | | | | | | | (0.070) | (0.109) | (0.093) | (0.079) |
| Inertia I_w | | | | | | | | | | | 0.565 | 0.157 | 0.165 |
| | | | | | | | | | | | (0.144) | (0.072) | (0.077) |
| Inertia I_wv | | | | | | | | | | | | 0.233 | 0.223 |
| | | | | | | | | | | | | (0.127) | (0.111) |
| Inertia I_w (normalization) | | | | | | | | | | | | | 0.161 |
| | | | | | | | | | | | | | (0.078) |
| Inertia I_wv (normalization) | | | | | | | | | | | | | |

(44B)

| | Wave length Δt | Wave height \|h\| | Peak position ratio r | Kurtosis k | Area ratio r_m | Depression θ | Area m | Inertia i | Inertia I (normalization) | Inertia I_w | Inertia I_wv | Inertia I_w (normalization) | Inertia I_wv (normalization) |
|---|---|---|---|---|---|---|---|---|---|---|---|---|---|
| Wave length Δt | | 0.221 | 0.193 | 0.176 | 0.201 | 0.187 | 0.151 | 0.159 | 0.165 | 0.206 | 0.328 | 0.186 | 0.225 |
| | | (0.093) | (0.077) | (0.059) | (0.084) | (0.075) | (0.028) | (0.043) | (0.050) | (0.081) | (0.122) | (0.066) | (0.087) |
| Wave height \|h\| | | | 0.178 | 0.187 | 0.182 | 0.204 | 0.207 | 0.169 | 0.170 | 0.186 | 0.221 | 0.175 | 0.173 |
| | | | (0.071) | (0.076) | (0.063) | (0.102) | (0.088) | (0.059) | (0.055) | (0.071) | (0.111) | (0.072) | (0.056) |
| Peak position ratio r | | | | 0.219 | 0.278 | 0.423 | 0.165 | 0.164 | 0.174 | 0.198 | 0.218 | 0.203 | 0.211 |
| | | | | (0.084) | (0.105) | (0.221) | (0.057) | (0.049) | (0.052) | (0.084) | (0.102) | (0.071) | (0.088) |
| Kurtosis k | | | | | 0.249 | 0.219 | 0.159 | 0.166 | 0.196 | 0.186 | 0.247 | 0.206 | 0.223 |
| | | | | | (0.092) | (0.078) | (0.039) | (0.050) | (0.082) | (0.073) | (0.109) | (0.069) | (0.082) |
| Area ratio r_m | | | | | | 0.255 | 0.170 | 0.156 | 0.207 | 0.212 | 0.266 | 0.232 | 0.205 |
| | | | | | | (0.111) | (0.056) | (0.039) | (0.084) | (0.083) | (0.111) | (0.091) | (0.075) |
| Depression θ | | | | | | | 0.164 | 0.161 | 0.189 | 0.163 | 0.222 | 0.195 | 0.185 |
| | | | | | | | (0.045) | (0.046) | (0.068) | (0.070) | (0.095) | (0.068) | (0.062) |
| Area m | | | | | | | | 0.179 | 0.174 | 0.189 | 0.216 | 0.169 | 0.174 |
| | | | | | | | | (0.067) | (0.064) | (0.083) | (0.096) | (0.057) | (0.057) |
| Inertia i | | | | | | | | | 0.177 | 0.170 | 0.201 | 0.162 | 0.160 |
| | | | | | | | | | (0.064) | (0.057) | (0.084) | (0.043) | (0.043) |
| Inertia I (normalization) | | | | | | | | | | 0.194 | 0.236 | 0.227 | 0.208 |
| | | | | | | | | | | (0.081) | (0.107) | (0.096) | (0.074) |
| Inertia I_w | | | | | | | | | | | 0.613 | 0.221 | 0.206 |
| | | | | | | | | | | | (0.137) | (0.086) | (0.084) |
| Inertia I_wv | | | | | | | | | | | | 0.313 | 0.281 |
| | | | | | | | | | | | | (0.131) | (0.116) |
| Inertia I_w (normalization) | | | | | | | | | | | | | 0.244 |
| | | | | | | | | | | | | | (0.095) |
| Inertia I_wv (normalization) | | | | | | | | | | | | | |

| | Wave length Δt | Wave height [h] | Peak position ratio r | Kurtosis k | Area ratio r_m | Depression θ | Area m | Inertia I | Inertia I (normalization) | Inertia I_w | Inertia I_wv | Inertia I_w (normalization) | Inertia I_wv (normalization) |
|---|---|---|---|---|---|---|---|---|---|---|---|---|---|
| Wave length Δt | | 0.224 | 0.165 | 0.164 | 0.157 | 0.164 | 0.138 | 0.146 | 0.159 | 0.176 | 0.315 | 0.176 | 0.162 |
| | | (0.153) | (0.081) | (0.078) | (0.066) | (0.076) | (0.049) | (0.062) | (0.060) | (0.083) | (0.137) | (0.074) | (0.083) |
| Wave height [h] | | | 0.166 | 0.151 | 0.177 | 0.188 | 0.187 | 0.155 | 0.157 | 0.178 | 0.187 | 0.172 | 0.154 |
| | | | (0.066) | (0.060) | (0.082) | (0.085) | (0.101) | (0.082) | (0.075) | (0.086) | (0.097) | (0.081) | (0.070) |
| Peak position ratio r | | | | 0.162 | 0.226 | 0.301 | 0.144 | 0.137 | 0.177 | 0.159 | 0.170 | 0.182 | 0.188 |
| | | | | (0.065) | (0.113) | (0.211) | (0.053) | (0.054) | (0.081) | (0.065) | (0.086) | (0.075) | (0.074) |
| Kurtosis k | | | | | 0.192 | 0.156 | 0.146 | 0.163 | 0.191 | 0.193 | 0.200 | 0.189 | 0.221 |
| | | | | | (0.084) | (0.063) | (0.060) | (0.077) | (0.095) | (0.090) | (0.106) | (0.075) | (0.087) |
| Area ratio r_m | | | | | | 0.214 | 0.148 | 0.165 | 0.179 | 0.186 | 0.212 | 0.178 | 0.207 |
| | | | | | | (0.105) | (0.057) | (0.079) | (0.084) | (0.085) | (0.124) | (0.073) | (0.081) |
| Depression θ | | | | | | | 0.134 | 0.150 | 0.170 | 0.161 | 0.171 | 0.167 | 0.174 |
| | | | | | | | (0.044) | (0.064) | (0.070) | (0.077) | (0.093) | (0.065) | (0.082) |
| Area m | | | | | | | | 0.184 | 0.141 | 0.151 | 0.168 | 0.164 | 0.143 |
| | | | | | | | | (0.076) | (0.050) | (0.061) | (0.075) | (0.082) | (0.053) |
| Inertia I | | | | | | | | | 0.149 | 0.155 | 0.168 | 0.143 | 0.154 |
| | | | | | | | | | (0.068) | (0.069) | (0.077) | (0.056) | (0.064) |
| Inertia I (normalization) | | | | | | | | | | 0.177 | 0.208 | 0.181 | 0.205 |
| | | | | | | | | | | (0.080) | (0.101) | (0.081) | (0.097) |
| Inertia I_w | | | | | | | | | | | 0.547 | 0.197 | 0.170 |
| | | | | | | | | | | | (0.170) | (0.090) | (0.073) |
| Inertia I_wv | | | | | | | | | | | | 0.236 | 0.220 |
| | | | | | | | | | | | | (0.117) | (0.116) |
| Inertia I_w (normalization) | | | | | | | | | | | | | 0.228 |
| | | | | | | | | | | | | | (0.108) |
| Inertia I_wv (normalization) | | | | | | | | | | | | | |

(45B)

| | Wave length Δt | Wave height [h] | Peak position ratio r | Kurtosis k | Area ratio r_m | Depression θ | Area m | Inertia I | Inertia I (normalization) | Inertia I_w | Inertia I_wv | Inertia I_w (normalization) | Inertia I_wv (normalization) |
|---|---|---|---|---|---|---|---|---|---|---|---|---|---|
| Wave length Δt | | 0.195 | 0.159 | 0.162 | 0.184 | 0.157 | 0.148 | 0.135 | 0.163 | 0.178 | 0.310 | 0.161 | 0.158 |
| | | (0.110) | (0.076) | (0.082) | (0.103) | (0.076) | (0.085) | (0.053) | (0.077) | (0.093) | (0.141) | (0.079) | (0.069) |
| Wave height [h] | | | 0.186 | 0.156 | 0.187 | 0.187 | 0.156 | 0.169 | 0.204 | 0.168 | 0.162 | 0.162 | 0.148 |
| | | | (0.103) | (0.076) | (0.119) | (0.101) | (0.073) | (0.103) | (0.120) | (0.093) | (0.099) | (0.081) | (0.067) |
| Peak position ratio r | | | | 0.177 | 0.214 | 0.334 | 0.139 | 0.152 | 0.153 | 0.183 | 0.182 | 0.172 | 0.160 |
| | | | | (0.082) | (0.126) | (0.219) | (0.056) | (0.074) | (0.067) | (0.096) | (0.097) | (0.085) | (0.072) |
| Kurtosis k | | | | | 0.168 | 0.168 | 0.161 | 0.155 | 0.174 | 0.161 | 0.185 | 0.155 | 0.161 |
| | | | | | (0.086) | (0.084) | (0.076) | (0.075) | (0.090) | (0.078) | (0.103) | (0.066) | (0.075) |
| Area ratio r_m | | | | | | 0.212 | 0.153 | 0.150 | 0.225 | 0.190 | 0.194 | 0.204 | 0.220 |
| | | | | | | (0.126) | (0.073) | (0.074) | (0.118) | (0.099) | (0.120) | (0.079) | (0.099) |
| Depression θ | | | | | | | 0.146 | 0.157 | 0.171 | 0.164 | 0.182 | 0.171 | 0.184 |
| | | | | | | | (0.060) | (0.073) | (0.087) | (0.072) | (0.093) | (0.085) | (0.087) |
| Area m | | | | | | | | 0.160 | 0.182 | 0.158 | 0.153 | 0.144 | 0.133 |
| | | | | | | | | (0.073) | (0.101) | (0.081) | (0.073) | (0.063) | (0.054) |
| Inertia I | | | | | | | | | 0.176 | 0.152 | 0.174 | 0.140 | 0.132 |
| | | | | | | | | | (0.098) | (0.071) | (0.105) | (0.060) | (0.058) |
| Inertia I (normalization) | | | | | | | | | | 0.166 | 0.165 | 0.174 | 0.181 |
| | | | | | | | | | | (0.088) | (0.092) | (0.085) | (0.091) |
| Inertia I_w | | | | | | | | | | | 0.585 | 0.162 | 0.161 |
| | | | | | | | | | | | (0.200) | (0.087) | (0.077) |
| Inertia I_wv | | | | | | | | | | | | 0.234 | 0.230 |
| | | | | | | | | | | | | (0.117) | (0.129) |
| Inertia I_w (normalization) | | | | | | | | | | | | | 0.178 |
| | | | | | | | | | | | | | (0.105) |
| Inertia I_wv (normalization) | | | | | | | | | | | | | |

Fig. 46

| | Wave length Δt | Wave height h | Peak position ratio r | Kurtosis k | Area ratio r_m | Depression θ | Area m | Inertia i | Inertia i (normalization) | Inertia I_w | Inertia I_wv | Inertia I_w (normalization) | Inertia I_wv (normalization) |
|---|---|---|---|---|---|---|---|---|---|---|---|---|---|
| Wave length Δt | | 0.252 (0.081) | 0.319 (0.302) | 0.278 (0.082) | 0.240 (0.044) | 0.338 (0.098) | 0.285 (0.047) | 0.234 (0.035) | 0.338 (0.048) | 0.277 (0.082) | 0.464 (0.147) | 0.264 (0.071) | 0.256 (0.074) |
| Wave height h | | | 0.273 (0.095) | 0.233 (0.041) | 0.309 (0.126) | 0.257 (0.098) | 0.273 (0.062) | 0.240 (0.046) | 0.273 (0.103) | 0.241 (0.053) | 0.285 (0.101) | 0.245 (0.061) | 0.239 (0.043) |
| Peak position ratio r | | | | 0.246 (0.059) | 0.253 (0.073) | 0.539 (0.108) | 0.239 (0.052) | 0.236 (0.046) | 0.251 (0.055) | 0.273 (0.076) | 0.358 (0.131) | 0.243 (0.052) | 0.258 (0.061) |
| Kurtosis k | | | | | 0.249 (0.094) | 0.247 (0.056) | 0.229 (0.050) | 0.228 (0.029) | 0.275 (0.081) | 0.275 (0.084) | 0.361 (0.139) | 0.251 (0.054) | 0.257 (0.065) |
| Area ratio r_m | | | | | | 0.261 (0.082) | 0.261 (0.085) | 0.234 (0.039) | 0.258 (0.054) | 0.247 (0.055) | 0.325 (0.134) | 0.243 (0.045) | 0.285 (0.065) |
| Depression θ | | | | | | | 0.228 (0.025) | 0.231 (0.030) | 0.249 (0.057) | 0.286 (0.080) | 0.342 (0.130) | 0.249 (0.053) | 0.249 (0.053) |
| Area m | | | | | | | | 0.242 (0.033) | 0.242 (0.057) | 0.232 (0.036) | 0.296 (0.098) | 0.252 (0.035) | 0.234 (0.038) |
| Inertia i | | | | | | | | | 0.245 (0.053) | 0.240 (0.056) | 0.297 (0.084) | 0.230 (0.031) | 0.336 (0.099) |
| Inertia i (normalization) | | | | | | | | | | 0.256 (0.087) | 0.277 (0.086) | 0.234 (0.036) | 0.238 (0.036) |
| Inertia I_w | | | | | | | | | | | 0.660 (0.299) | 0.257 (0.077) | 0.263 (0.066) |
| Inertia I_wv | | | | | | | | | | | | 0.402 (0.153) | 0.441 (0.145) |
| Inertia I_w (normalization) | | | | | | | | | | | | | 0.253 (0.053) |
| Inertia I_wv (normalization) | | | | | | | | | | | | | |

FIG. 47

| | Wave length Δt | Wave height \|h\| | Peak position ratio r | Kurtosis k | Area ratio r_m | Depression θ | Area m | Inertia I | Inertia I (normalization) | Inertia I_w | Inertia I_wv | Inertia I_w (normalization) | Inertia I_wv (normalization) |
|---|---|---|---|---|---|---|---|---|---|---|---|---|---|
| Wave length Δt | | 0.211 | 0.174 | 0.165 | 0.174 | 0.177 | 0.134 | 0.133 | 0.155 | 0.163 | 0.346 | 0.161 | 0.169 |
| | | (0.115) | (0.086) | (0.080) | (0.085) | (0.085) | (0.058) | (0.061) | (0.071) | (0.083) | (0.133) | (0.076) | (0.081) |
| Wave height \|h\| | | | 0.171 | 0.145 | 0.175 | 0.178 | 0.181 | 0.155 | 0.165 | 0.172 | 0.204 | 0.151 | 0.141 |
| | | | (0.088) | (0.069) | (0.091) | (0.090) | (0.095) | (0.083) | (0.090) | (0.089) | (0.104) | (0.074) | (0.065) |
| Peak position ratio r | | | | 0.174 | 0.206 | 0.384 | 0.143 | 0.139 | 0.154 | 0.179 | 0.195 | 0.177 | 0.180 |
| | | | | (0.076) | (0.103) | (0.198) | (0.066) | (0.063) | (0.068) | (0.086) | (0.100) | (0.076) | (0.076) |
| Kurtosis k | | | | | 0.202 | 0.172 | 0.144 | 0.144 | 0.182 | 0.204 | 0.215 | 0.189 | 0.192 |
| | | | | | (0.084) | (0.077) | (0.062) | (0.064) | (0.088) | (0.093) | (0.112) | (0.082) | (0.082) |
| Area ratio r_m | | | | | | 0.204 | 0.144 | 0.142 | 0.179 | 0.182 | 0.211 | 0.200 | 0.196 |
| | | | | | | (0.107) | (0.067) | (0.065) | (0.082) | (0.088) | (0.113) | (0.077) | (0.080) |
| Depression θ | | | | | | | 0.142 | 0.140 | 0.155 | 0.174 | 0.199 | 0.169 | 0.169 |
| | | | | | | | (0.060) | (0.062) | (0.069) | (0.083) | (0.102) | (0.073) | (0.074) |
| Area m | | | | | | | | 0.149 | 0.152 | 0.148 | 0.180 | 0.146 | 0.144 |
| | | | | | | | | (0.067) | (0.075) | (0.071) | (0.094) | (0.066) | (0.062) |
| Inertia I | | | | | | | | | 0.147 | 0.142 | 0.175 | 0.141 | 0.141 |
| | | | | | | | | | (0.070) | (0.068) | (0.092) | (0.061) | (0.061) |
| Inertia I (normalization) | | | | | | | | | | 0.161 | 0.188 | 0.172 | 0.173 |
| | | | | | | | | | | (0.079) | (0.098) | (0.080) | (0.076) |
| Inertia I_w | | | | | | | | | | | 0.606 | 0.171 | 0.187 |
| | | | | | | | | | | | (0.163) | (0.080) | (0.082) |
| Inertia I_wv | | | | | | | | | | | | 0.236 | 0.233 |
| | | | | | | | | | | | | (0.115) | (0.110) |
| Inertia I_w (normalization) | | | | | | | | | | | | | 0.191 |
| | | | | | | | | | | | | | (0.092) |
| Inertia I_wv (normalization) | | | | | | | | | | | | | |

Combination of high precision
1: Wave length Δt - Inertia I
2: Wave length Δt - Area m
3: Peak position ratio r - Inertia I
4: Depression θ - Inertia I
5: Inertia I - Inertia I_w (normalization)

FIG. 48

| | Wave length Δt | Wave height \|h\| | Peak position ratio r | Kurtosis k | Area ratio r_m | Depression θ | Area m | Inertia I | Inertia I (normalization) | Inertia I_w | Inertia I_wv | Inertia I_w (normalization) | Inertia I_wv (normalization) |
|---|---|---|---|---|---|---|---|---|---|---|---|---|---|
| Wave length Δt | | 0.202 (0.126) | 0.140 (0.090) | 0.134 (0.083) | 0.152 (0.096) | 0.143 (0.090) | 0.099 (0.064) | 0.098 (0.072) | 0.132 (0.078) | 0.121 (0.087) | 0.339 (0.128) | 0.123 (0.078) | 0.138 (0.087) |
| Wave height \|h\| | | | 0.143 (0.094) | 0.112 (0.078) | 0.139 (0.089) | 0.154 (0.096) | 0.155 (0.105) | 0.127 (0.092) | 0.133 (0.091) | 0.151 (0.100) | 0.204 (0.111) | 0.114 (0.075) | 0.106 (0.073) |
| Peak position ratio r | | | | 0.148 (0.078) | 0.166 (0.100) | 0.349 (0.193) | 0.117 (0.081) | 0.104 (0.069) | 0.118 (0.071) | 0.151 (0.090) | 0.151 (0.091) | 0.148 (0.081) | 0.153 (0.079) |
| Kurtosis k | | | | | 0.180 (0.085) | 0.144 (0.082) | 0.113 (0.074) | 0.112 (0.073) | 0.152 (0.091) | 0.201 (0.103) | 0.168 (0.101) | 0.171 (0.096) | 0.168 (0.090) |
| Area ratio r_m | | | | | | 0.171 (0.108) | 0.107 (0.071) | 0.105 (0.070) | 0.138 (0.078) | 0.150 (0.092) | 0.161 (0.097) | 0.181 (0.081) | 0.171 (0.081) |
| Depression θ | | | | | | | 0.117 (0.077) | 0.107 (0.070) | 0.117 (0.070) | 0.149 (0.091) | 0.169 (0.099) | 0.142 (0.082) | 0.141 (0.077) |
| Area m | | | | | | | | (0.067) | 0.121 (0.083) | 0.117 (0.081) | 0.152 (0.101) | 0.115 (0.073) | 0.122 (0.076) |
| Inertia I | | | | | | | | | 0.109 (0.073) | 0.104 (0.073) | 0.142 (0.095) | 0.111 (0.074) | 0.108 (0.068) |
| Inertia I (normalization) | | | | | | | | | | 0.128 (0.081) | 0.152 (0.095) | 0.136 (0.082) | 0.138 (0.075) |
| Inertia I_w | | | | | | | | | | | 0.617 (0.151) | 0.136 (0.078) | 0.178 (0.091) |
| Inertia I_wv | | | | | | | | | | | | 0.177 (0.096) | 0.174 (0.094) |
| Inertia I_w (normalization) | | | | | | | | | | | | | 0.163 (0.095) |
| Inertia I_wv (normalization) | | | | | | | | | | | | | |

Combination of high precision
1: Wave length Δt - Inertia I
2: Wave length Δt - Area m
3: Peak position ratio r - Inertia I
4: Inertia I - Inertia I_w
5: Depression θ - Inertia I

FIG. 49

| | Wave length Δt | Wave height \|h\| | Peak position ratio r | Kurtosis k | Area ratio r_m | Depression θ | Area m | Inertia I | Inertia I (normalization) | Inertia I_w | Inertia I_wv | Inertia I_w (normalization) | Inertia I_wv (normalization) |
|---|---|---|---|---|---|---|---|---|---|---|---|---|---|
| Wave length Δt | | 0.217 (0.106) | 0.201 (0.083) | 0.190 (0.077) | 0.191 (0.076) | 0.204 (0.082) | 0.162 (0.053) | 0.173 (0.064) | 0.196 (0.080) | 0.351 (0.137) | 0.191 (0.075) | 0.194 (0.077) | |
| Wave height \|h\| | | | 0.193 (0.083) | 0.172 (0.062) | 0.204 (0.093) | 0.198 (0.086) | 0.202 (0.088) | 0.190 (0.089) | 0.189 (0.079) | 0.204 (0.098) | 0.181 (0.072) | 0.169 (0.059) | |
| Peak position ratio r | | | | 0.195 (0.074) | 0.238 (0.105) | 0.411 (0.201) | 0.164 (0.054) | 0.182 (0.065) | 0.200 (0.083) | 0.229 (0.107) | 0.201 (0.073) | 0.201 (0.074) | |
| Kurtosis k | | | | | 0.219 (0.083) | 0.195 (0.073) | 0.169 (0.052) | 0.170 (0.056) | 0.206 (0.084) | 0.252 (0.120) | 0.203 (0.072) | 0.211 (0.077) | |
| Area ratio r_m | | | | | | 0.230 (0.106) | 0.174 (0.063) | 0.170 (0.061) | 0.207 (0.085) | 0.250 (0.125) | 0.215 (0.074) | 0.216 (0.079) | |
| Depression θ | | | | | | | 0.162 (0.046) | 0.168 (0.055) | 0.185 (0.068) | 0.222 (0.105) | 0.194 (0.077) | 0.191 (0.071) | |
| Area m | | | | | | | | 0.183 (0.067) | 0.177 (0.068) | 0.173 (0.064) | 0.171 (0.061) | 0.163 (0.052) | |
| Inertia I | | | | | | | | | 0.177 (0.068) | 0.172 (0.064) | 0.164 (0.050) | 0.167 (0.055) | |
| Inertia I (normalization) | | | | | | | | | | 0.188 (0.077) | 0.217 (0.100) | 0.201 (0.078) | 0.200 (0.076) |
| Inertia I_w | | | | | | | | | | | 0.598 (0.172) | 0.199 (0.082) | 0.193 (0.075) |
| Inertia I_wv | | | | | | | | | | | | 0.283 (0.129) | 0.279 (0.123) |
| Inertia I_w (normalization) | | | | | | | | | | | | | 0.213 (0.090) |
| Inertia I_wv (normalization) | | | | | | | | | | | | | |

Combination of high precision
1: Wave length Δt - Area m
2: Wave length Δt - Inertia I
3: Depression θ - Area m
4: Area m - Inertia I_wv (normalization)
5: Peak position ratio r - Area m

FIG. 50
(50A)
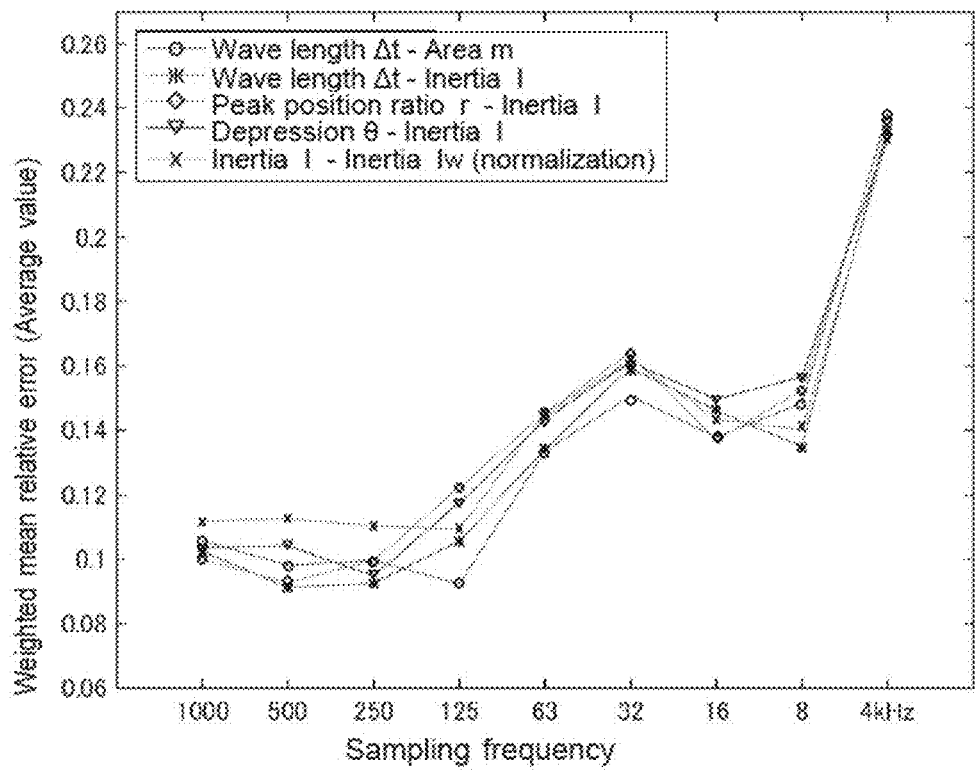
(50B)
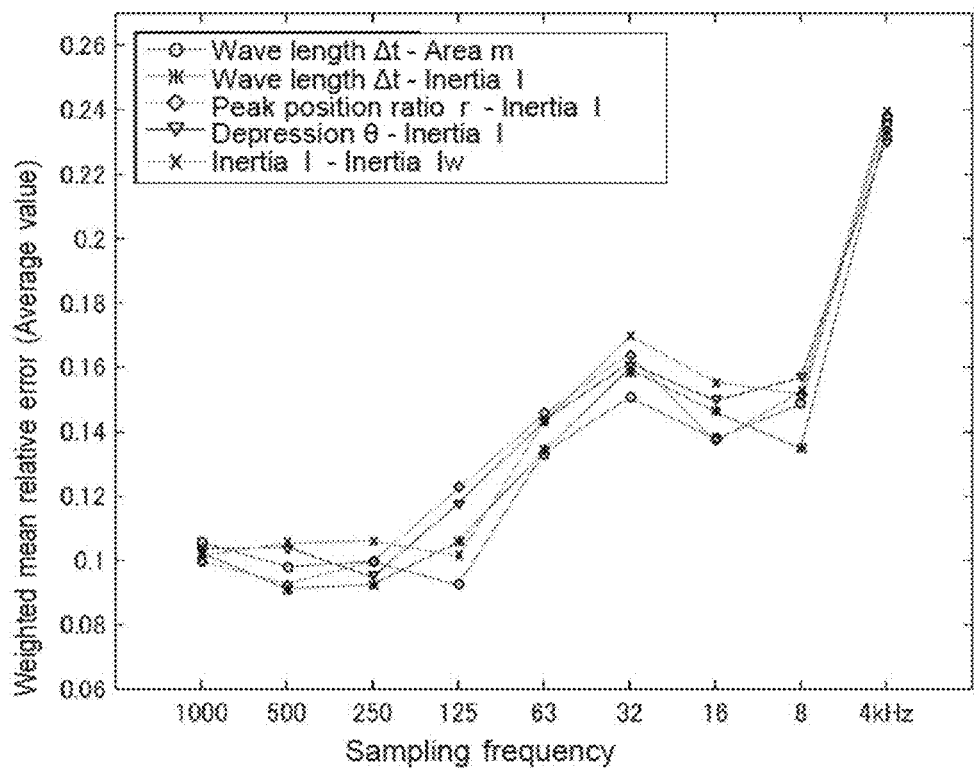

FIG. 51
(51A)
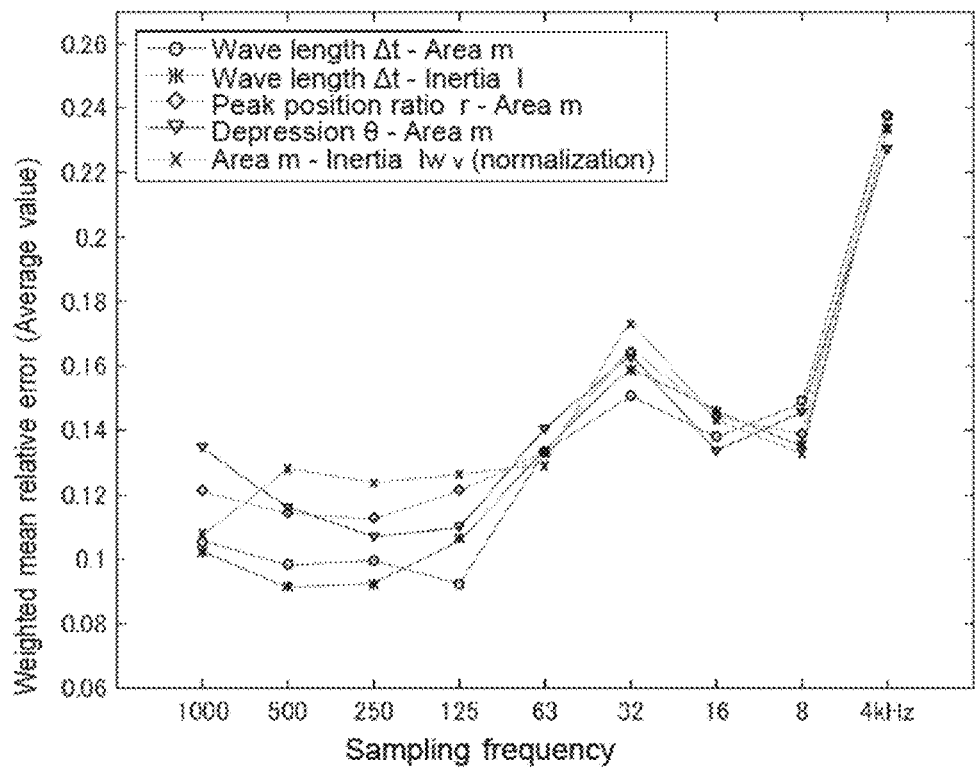
(51B)
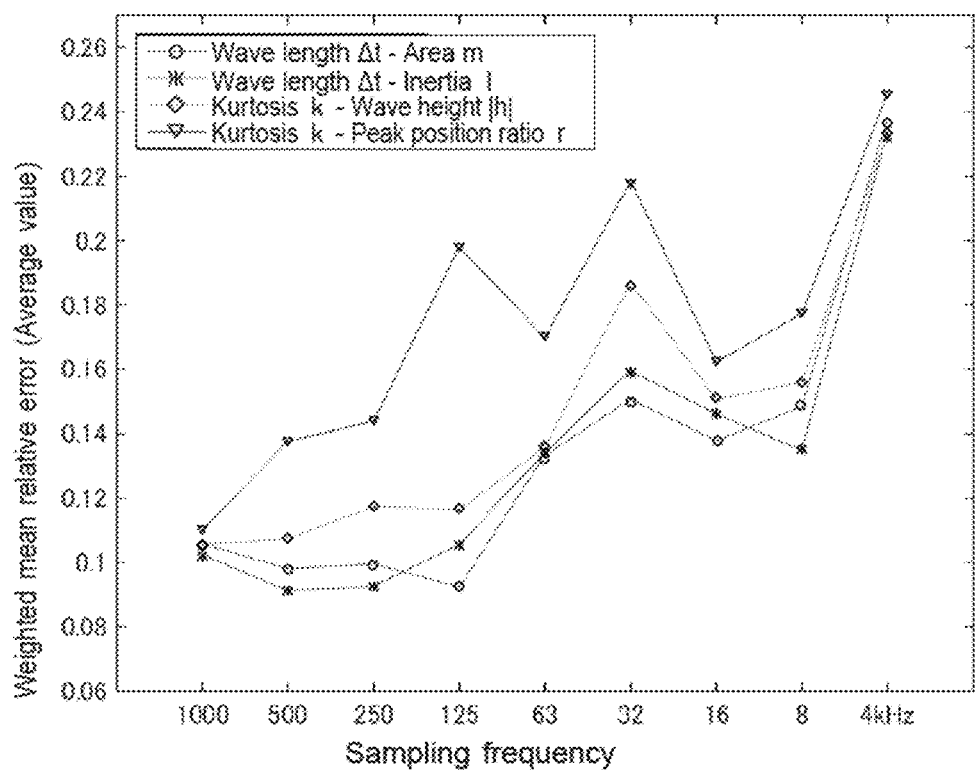

FIG. 52
(52A)
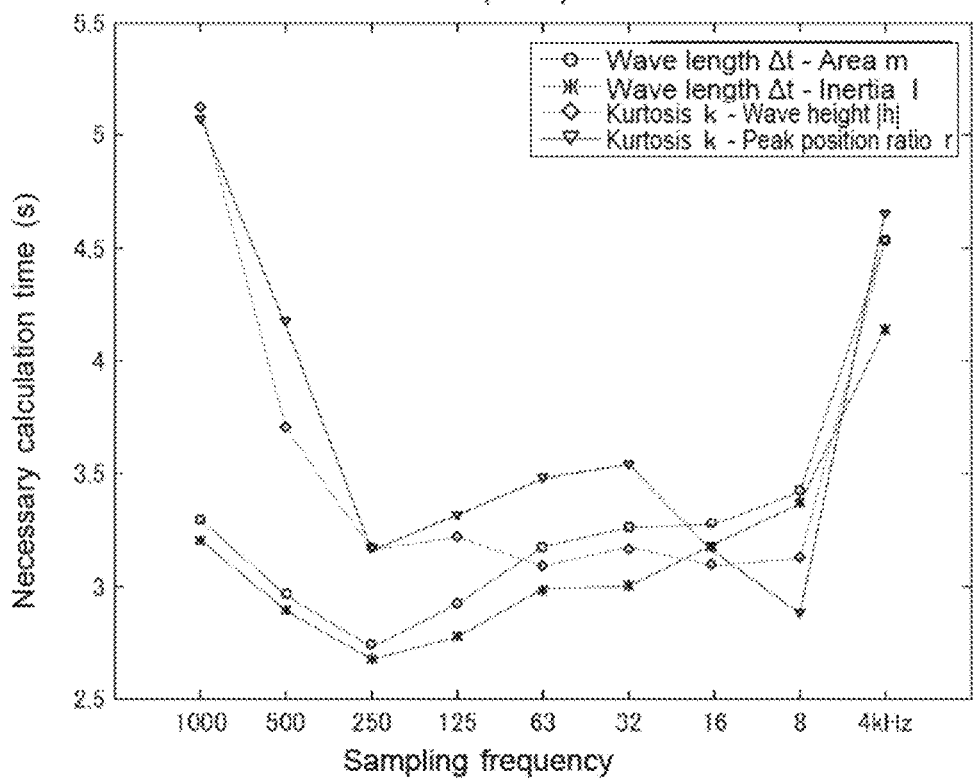
(52B)
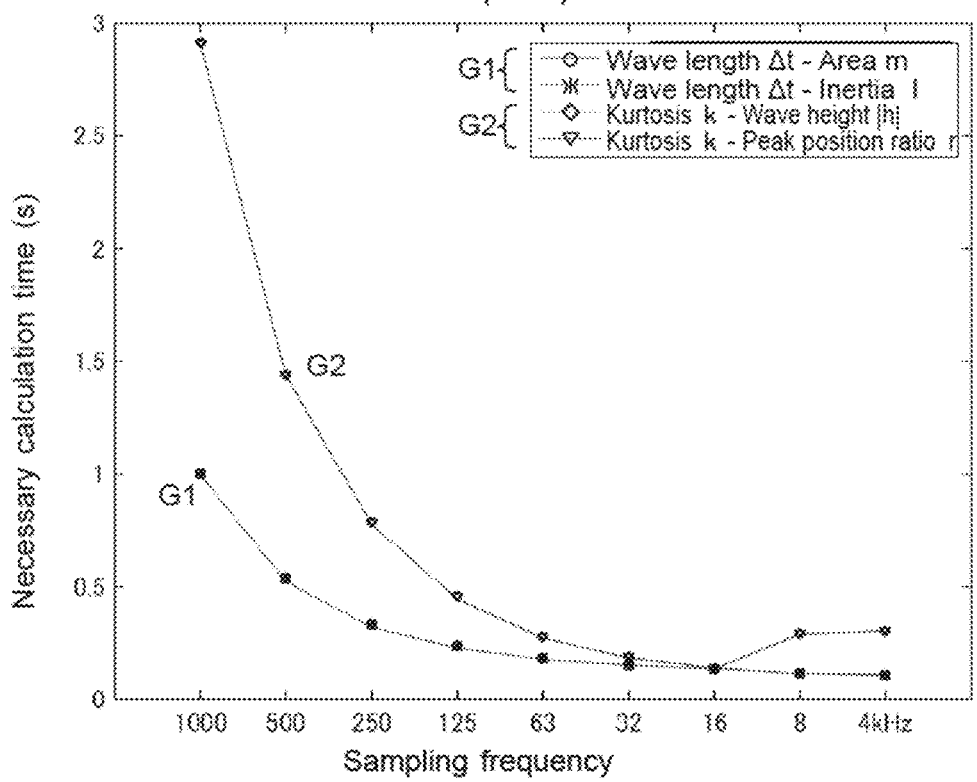

NUMBER ANALYZING METHOD, NUMBER ANALYZING DEVICE, AND STORAGE MEDIUM FOR NUMBER ANALYSIS

CROSS REFERENCE TO RELATED APPLICATIONS

The present application is a divisional of U.S. patent application Ser. No. 16/065,633, filed Jun. 22, 2018, which is a National Stage Entry of PCT/JP2016/087821, filed Dec. 19, 2016, which claims priority to JP Pat. App. No. 2015-254398, filed Dec. 25, 2015, the contents of each of which are incorporated herein by reference in their entirety.

FIELD OF THE INVENTION

The present invention relates to a number analyzing method, a number analyzing device and a storage medium for number analysis which analyze the number and number distribution of particulate or molecular analytes, for example minute object such as virus and bacteria or fine dust.

BACKGROUND ART

Conventionally, microbial examination for bacteria and the like is performed by a biochemical method. In biochemical examination, organs and staining are performed due to the synonymy of the number and kind of bacteria.

PRIOR ART DOCUMENT

Patent Document

[Patent Document 1] International Publication WO2013/137209 bulletin

DISCLOSURE OF THE INVENTION

Problems to be Solved by the Invention

In the examination by the above-described conventional biochemical method, the examination time is about several days (for example, the culture time of E. coli is 1 to 2 days), and the examiner was also required expert skills. For this reason, in modern society where the number of people and goods increases, in order to prevent health damage due to food safety, pandemic prevention, air pollution caused by fine particulate matter such as PM 2.5, there is a need for an inspection method that anyone can perform, quickly and easily, and at low cost.

Patent document 1 discloses an electrical detection technology of minute objects (bacteria, viruses, etc.) using a micro•nanopore device having fine through-holes (micropores, hereinafter referred to as nanopores) on a micro•nanometer scale.

The operating principle of the micro•nanopore device is as follows. When a voltage is applied to an electrode pair arranged so as to sandwich a nanopore at the up and down sides of the nanopore filled with an electrolytic solution, the current measured is proportional to the pore diameter, the ion concentration and the applied voltage, and is inversely proportional to the pore depth. When a subject (analyte) such as bacteria passes through a pore (through-hole), a part of the ion current is inhibited by the subject, so that a current change like a pulse appears. By observing this current change, the subject existing in the electrolytic solution can be detected.

When the type of subject in solution is known, the detected number of current changes is the total number of subjects. However, in an actual examination, since an analyte of unknown type may be an object to be examined, in practical use of a nanopore device, there was a problem that it cannot be applied to a detailed examination of an analyte type merely by extracting a current change simply.

An object of the present invention is to provide a number analyzing method, a number analyzing apparatus, and a storage medium for number analysis which can analyze the number and number distribution corresponding to the type of particulate or molecular analyte with high accuracy.

Means to Solve the Problems

In view of the above problems, the present invention focuses on the fact that the shape of a passing analyte is reflected in the waveform of the inhibition current detected when the nanopore has a low aspect ratio with a sufficiently small pore thickness relative to the pore diameter, and this invention is completed based on new knowledge that it is possible to derive the number or number distribution corresponding to the type of analyte by adding statistical computer analysis to data obtained through mathematically extracting the feature of the inhibiting current waveform,.

The first form of the present invention is the number analyzing method comprising the steps of arranging a partition wall with a through-hole and electrodes disposed on a front side and a back side of said partition wall through said through-hole, supplying a flowable material containing particulate or molecular analytes to one side of said partition wall, obtaining detection signals of an electrical conduction change between said electrodes caused by passage of said analytes through said through-hole, and analyzing the number of each analyte type by executing a computer control program based on a data of said detection signals, wherein said computer control program performs a probability density estimation from a data group based on feature values indicating feature of waveforms of pulse signals obtained as said detection signals which correspond to said passage of analytes and at least has a number deriving means which derives the number of each analyte type.

The second form of the present invention is the number analyzing method, wherein said feature value is either of first type showing local feature of waveforms of said pulse signals and second type showing global feature of waveforms of said pulse signals.

The third form of the present invention is the number analyzing method, wherein the feature value of said first type is one selected from a group of a wave height value of the waveform in a predetermined time width, a pulse wavelength $t_a$, a peak position ratio represented by ratio $t_b/t_a$ of time $t_a$ and $t_b$ leading from the pulse start to the pulse peak, a kurtosis which represents the sharpness of the waveform, a depression representing the slope leading from the pulse start to the pulse peak, an area representing total sum of the time division area dividing the waveform with the predetermined times, and an area ratio of sum of the time division area leading from the pulse start to the pulse peak to the total waveform area.

The fourth form of the present invention is the number analyzing method, wherein the feature value of said second type is one selected from a group of a time inertia moment determined by mass and rotational radius when the mass is constructive to said time division area centered at the pulse start time and the rotational radius is constructive to time leading from said center to said time division area, a normalized time inertia moment determined when said time inertia moment is normalized so as that the wave height becomes a reference value, a wave width mean value inertia moment determined by mass distribution and rotational center when the mass distribution is constructive to mean value difference vector whose vector component is mean value difference of the same wave height position in which the wave form is equally divided in the wave height direction and the mean value of time values is calculated for each division unit in before and after each pulse peak and the rotational center is constructive to time axis of waveform foot, a normalized wave width mean value inertia moment determined when said wave width mean value inertia moment is normalized so as that the wavelength becomes a standard value, a wave width dispersion inertia moment determined by mass distribution and rotational center when the mass distribution is constructive to dispersion vector whose vector component is dispersion in which the wave form is equally divided in the wave height direction and the dispersion is calculated from time value for each division unit and the rotational center is constructive to time axis of waveform foot, and a normalized wave width dispersion inertia moment determined when said wave width dispersion inertia moment is normalized so as that the wavelength becomes a standard value.

The fifth form of the present invention is the number analyzing method, wherein said computer control program includes a base line extraction means extracting a base line at no passage of analytes from a data of said detection signals or fluctuation components contained therein, a pulse extraction means extracting a signal data over a predetermined range based on said base line as a data of said pulse signals, and a feature value extraction means extracting said feature value from said data of extracted pulse signals.

The sixth form of the present invention is the number analyzing device comprising a partition wall with a through-hole, electrodes disposed on a front side and a back side of said partition wall through said through-hole, a flowable material containing particulate or molecular analytes supplied to one side of said partition wall, a computer control program analyzing the number of each analyte type based on a data of detection signals when said detection signals are obtained through an electrical conduction change caused between said electrodes by passage of said analytes through said through-hole, a storage means storing said data of detection signals, and a control means controlling the execution of said computer control program based on said data of detection signals, wherein said computer control program performs a probability density estimation from a data group based on feature values indicating feature of waveforms of pulse signals obtained as said detection signals which correspond to said passage of analytes and at least has a number deriving means which derives the number of each analyte type.

The seventh form of the present invention is the number analyzing device, wherein said feature value is either of first type showing local feature of waveforms of said pulse signals and second type showing global feature of waveforms of said pulse signals.

The eighth form of the present invention is the number analyzing device, wherein the feature value of said first type is one selected from a group of a wave height value of the waveform in a predetermined time width, a pulse wavelength $t_a$, a peak position ratio represented by ratio $t_b/t_a$ of time $t_a$ and $t_b$ leading from the pulse start to the pulse peak, a kurtosis which represents the sharpness of the waveform, a depression representing the slope leading from the pulse start to the pulse peak, an area representing total sum of the time division area dividing the waveform with the predetermined times, and an area ratio of sum of the time division area leading from the pulse start to the pulse peak to the total waveform area.

The ninth form of the present invention is the number analyzing device, wherein the feature value of said second type is one selected from a group of a time inertia moment determined by mass and rotational radius when the mass is constructive to said time division area centered at the pulse start time and the rotational radius is constructive to time leading from said center to said time division area, a normalized time inertia moment determined when said time inertia moment is normalized so as that the wave height becomes a reference value, a wave width mean value inertia moment determined by mass distribution and rotational center when the mass distribution is constructive to mean value difference vector whose vector component is mean value difference of the same wave height position in which the wave form is equally divided in the wave height direction and the mean value of time values is calculated for each division unit in before and after each pulse peak and the rotational center is constructive to time axis of waveform foot, a normalized wave width mean value inertia moment determined when said wave width mean value inertia moment is normalized so as that the wavelength becomes a standard value, a wave width dispersion inertia moment determined by mass distribution and rotational center when the mass distribution is constructive to dispersion vector whose vector component is dispersion in which the wave form is equally divided in the wave height direction and the dispersion is calculated from time value for each division unit and the rotational center is constructive to time axis of waveform foot, and a normalized wave width dispersion inertia moment determined when said wave width dispersion inertia moment is normalized so as that the wavelength becomes a reference value.

The tenth form of the present invention is the number analyzing device, wherein said computer control program includes a base line extraction means extracting a base line at no passage of analytes from a data of said detection signals or fluctuation components contained therein, a pulse extraction means extracting a signal data over a predetermined range based on said base line as a data of said pulse signals, and a feature value extraction means extracting said feature value from said data of extracted pulse signals.

The eleventh form of the present invention is the number analyzing device, wherein said number analyzing device includes an output means which outputs the number data derived by said number deriving means with a predetermined output form for each analyte type.

The twelfth form of the present invention is the storage medium for number analysis comprises a storage medium in which said computer control program described in first form is stored.

According to the number analyzing method of the first form, by executing the computer control program on the basis of the data group of the detection signal detected through the nanopore device, the probability density estimation is performed from the data group based on the feature value showing the feature of the waveform of the pulse signal corresponding to the analyte passage, which is the detection signal obtained by the number deriving means, and then the number of analytes such as bacteria, microparticulate substance and molecular substance can be derived, so that it is possible to analyze the number or the number distribution corresponding to the type of the analyte with high accuracy and it becomes possible to realize simplification and cost reduction in the analytical examination (inspection).

According to the second form, as the parameters derived from the pulse signal, since said feature value is either of first type showing local feature of waveforms of said pulse signals and second type showing global feature of waveforms of said pulse signals, by carrying out the number analysis using one or two or more of these feature values, it is possible to analyze the number or number distribution corresponding to the type of analyte with high accuracy, so that it can contribute to simplification and cost reduction in analytical inspection.

In the number analyzing method according to the present invention, it is not limited to the case where the number analysis is performed by using at least one or more feature values from the feature values of the first type or the second type, and it is possible to perform the number analysis in combination by using at least one or more feature values from each of the first type and the second type.

According to the third form, the feature value of said first type is one selected from a group of a wave height value of the waveform in a predetermined time width, a pulse wavelength $t_a$, a peak position ratio represented by ratio $t_b/t_a$ of time $t_a$ and $t_b$ leading from the pulse start to the pulse peak, a kurtosis which represents the sharpness of the waveform, a depression representing the slope leading from the pulse start to the pulse peak, an area representing total sum of the time division area dividing the waveform with the predetermined times, and an area ratio of sum of the time division area leading from the pulse start to the pulse peak to the total waveform area, so that by carrying out the number analysis using one or two or more of these feature values, it is possible to analyze the number or number distribution corresponding to the type of analyte with high accuracy, and it can contribute to simplification and cost reduction in analytical inspection.

According to the fourth form, the feature value of said second type is one selected from a group of a time inertia moment determined by mass and rotational radius when the mass is constructive to said time division area centered at the pulse start time and the rotational radius is constructive to time leading from said center to said time division area, a normalized time inertia moment determined when said time inertia moment is normalized so as that the wave height becomes a reference value, a wave width mean value inertia moment determined by mass distribution and rotational center when the mass distribution is constructive to mean value difference vector whose vector component is mean value difference of the same wave height position in which the wave form is equally divided in the wave height direction and the mean value of time values is calculated for each division unit in before and after each pulse peak and the rotational center is constructive to time axis of waveform foot, a normalized wave width mean value inertia moment determined when said wave width mean value inertia moment is normalized so as that the wavelength becomes a standard value, a wave width dispersion inertia moment determined by mass distribution and rotational center when the mass distribution is constructive to dispersion vector whose vector component is dispersion in which the wave form is equally divided in the wave height direction and the dispersion is calculated from time value for each division unit and the rotational center is constructive to time axis of waveform foot, and a normalized wave width dispersion inertia moment determined when said wave width dispersion inertia moment is normalized so as that the wavelength becomes a standard value, so that by carrying out the number analysis using one or two or more of these feature values, it is possible to analyze the number or number distribution corresponding to the type of analyte with high accuracy, and it can contribute to simplification and cost reduction in analytical inspection.

According to the fifth form, the base line at no passage of analytes is extracted from the data of said detection signals or fluctuation components contained therein by the base line extraction means, the signal data over a predetermined range is extracted based on said base line as the data of said pulse signals by the pulse extraction means, and the feature value is extracted from the data of extracted pulse signals by the feature value extraction means, so that it is possible to analyze the number or the number distribution according to the type of analyte with high accuracy by executing the number analysis based on the feature value derived from the pulse signal, and it can contribute to simplification and cost reduction in analytical inspection.

According to the sixth form, since the number analysis based on the number analyzing method according to the first form can be executed by the computer analysis, it has all the effects of the computer control program explained in the first form, so that the number or number distribution can be analyzed with high accuracy, and it is possible to provide the number analyzing apparatus which can perform the number analysis simply and inexpensively.

According to the seventh form, as the parameters derived from the pulse signal, since said feature value is either of first type showing local feature of waveforms of said pulse signals and second type showing global feature of waveforms of said pulse signals, by carrying out the number analysis using one or two or more of these feature values, it is possible to analyze the number or number distribution corresponding to the type of analyte with high accuracy, so that it can contribute to simplification and cost reduction in analytical inspection and it is possible to provide the number analyzing apparatus which can perform the number analysis simply and inexpensively.

In the number analyzing device according to the present invention, it is not limited to the case where the number analysis is performed by using at least one or more feature values from the feature values of the first type or the second type, and it is possible to perform the number analysis in combination by using at least one or more feature values from each of the first type and the second type.

According to the eighth form, the feature value of said first type is one selected from a group of a wave height value of the waveform in a predetermined time width, a pulse wavelength $t_a$, a peak position ratio represented by ratio $t_b/t_a$ of time $t_a$ and $t_b$ leading from the pulse start to the pulse peak, a kurtosis which represents the sharpness of the waveform, a depression representing the slope leading from the pulse start to the pulse peak, an area representing total sum of the time division area dividing the waveform with the predetermined times, and an area ratio of sum of the time division area leading from the pulse start to the pulse peak to the total waveform area, so that by carrying out the number analysis using one or two or more of these feature values, it is possible to analyze the number or number distribution corresponding to the type of analyte with high accuracy, and it is possible to provide the number analyzing apparatus which can perform the number analysis simply and inexpensively.

According to the ninth form, the feature value of said second type is one selected from a group of a time inertia moment determined by mass and rotational radius when the mass is constructive to said time division area centered at the pulse start time and the rotational radius is constructive to time leading from said center to said time division area, a normalized time inertia moment determined when said time inertia moment is normalized so as that the wave height becomes a reference value, a wave width mean value inertia moment determined by mass distribution and rotational center when the mass distribution is constructive to mean value difference vector whose vector component is mean value difference of the same wave height position in which the wave form is equally divided in the wave height direction and the mean value of time values is calculated for each division unit in before and after each pulse peak and the rotational center is constructive to time axis of waveform foot, a normalized wave width mean value inertia moment determined when said wave width mean value inertia moment is normalized so as that the wavelength becomes a standard value, a wave width dispersion inertia moment determined by mass distribution and rotational center when the mass distribution is constructive to dispersion vector whose vector component is dispersion in which the wave form is equally divided in the wave height direction and the dispersion is calculated from time value for each division unit and the rotational center is constructive to time axis of waveform foot, and a normalized wave width dispersion inertia moment determined when said wave width dispersion inertia moment is normalized so as that the wavelength becomes a reference value, so that by carrying out the number analysis using one or two or more of these feature values, it is possible to analyze the number or number distribution corresponding to the type of analyte with high accuracy, and it is possible to provide the number analyzing apparatus which can perform the number analysis simply and inexpensively.

According to the tenth form, the base line at no passage of analytes is extracted from the data of said detection signals or fluctuation components contained therein by the base line extraction means, the signal data over a predetermined range is extracted based on said base line as the data of said pulse signals by the pulse extraction means, and the feature value is extracted from the data of extracted pulse signals by the feature value extraction means, so that it is possible with computer to analyze the number or the number distribution according to the type of analyte with high accuracy by executing the number analysis based on the feature value derived from the pulse signal, and it is possible to provide the number analyzing device which can perform the number analysis simply and inexpensively.

According to the eleventh form, since the number data derived by the number deriving means can be outputted in a predetermined output form for each analyte type, for example, by displaying and outputting the examination result immediately at the examination site, it is possible to notify the examination result promptly, and it is possible to provide the number analyzing device which can perform the number analysis rapidly, simply and inexpensively.

According to the twelfth form, it is possible to provide the storage medium for number analysis that stores the computer control program according to the first form. Therefore, since the storage medium according to the present form form has the effect of the computer control program described in the first form, it is possible to install the computer control program stored in the storage medium for number analysis in the computer and execute the number analyzing operation, so that it is possible to perform the number analysis simply and inexpensively.

As the storage medium in the present invention, any one of storage media readable by a computer such as a flexible disk, a magnetic disk, an optical disk, a CD, an MO, a DVD, a hard disk, a mobile terminal and the like can be selected.

Effects of the Invention

According to the present invention, it is possible to analyze the number or number distribution of analytes such as, for example, bacteria, microparticulate substance, molecular substance and the like, at low cost, simply and with high accuracy using a computer terminal.

BRIEF DESCRIPTION OF THE DRAWINGS

FIG. 6 is a diagram for explaining the Karman filter.

FIG. 12 is a table showing the number of pulses picked up from the waveform of the bead model according to the combination of m, k, and a of the adjustment factors.

FIG. 15 is a diagram showing each feature value (15 A) relating to one waveform data and an image diagram (15 B) of a probability density function in the particle types of *Escherichia coli* and *Bacillus subtilis*.

FIG. 18 is a diagram for explaining the derivation process of the constrained logarithmic likelihood maximization formula that performs optimization by the Lagrange undetermined multiplier method.

FIG. 23 is a flowchart showing the processing procedure by the EM algorithm.

FIG. 24 is a diagram showing an example of result analyzed by the number analyzing device according to the present embodiment.

FIG. 25 is a table showing each estimation result data of a verification example using a pulse wavelength and a wave height as the feature value and a verification example using a pulse wavelength and a peak position ratio as the feature value.

FIG. 26 is a table showing each estimation result data of the verification example using the spread of the peak vicinity waveform and the pulse wavelength as the feature value and the verification example using the spread of the peak vicinity waveform and the wave height as the feature value.

FIG. 27 is a diagram showing the number estimation result of the kurtosis and the pulse wave height as the feature value.

FIG. 28 is a table obtained by the BL estimation process based on the BL estimation process program.

FIG. 29 is a histogram showing each number estimation result when the mixing ratios of *E. coli* and *B. subtilis* are 1:10, 2:10, 3:10, and 35: 100, respectively.

FIG. 30 is a histogram showing the number estimation results when the mixing ratios of *E. coli* and *B. subtilis* are set to 4:10, 45:100, 1:2, respectively.

FIG. 31 is a diagram combining dispersed states of respective particles when the pulse width and the pulse wave height are used as the feature values.

FIG. 34 is a pulse waveform diagram for explaining the feature values of the depression and the area.

FIG. 37 is a pulse waveform diagram for explaining the feature value of the inertia moment with respect to the time (wavelength) and the wave width.

FIG. 38 is a diagram for explaining the relation between the wave width vector of $d_w$ dimension and the data sampling.

FIG. 39 is a diagram for explaining the acquiring process of acquiring the inertia moment with respect to the wave width from the wave width vector.

FIG. 42 is an estimation evaluation table relating to the combinations of the feature value when the sampling is performed at 1 MHz and 500 kHz.

FIG. 43 is an estimation evaluation table relating to the combinations of the feature value when the sampling is performed at 250 kHz and 125 kHz.

FIG. 44 is an estimation evaluation table relating to the combinations of the feature value when the sampling is performed at 63 kHz and 32 kHz.

FIG. 45 is an estimation evaluation table relating to the combinations of the feature value when the sampling is performed at 16 kHz and 8 kHz.

FIG. 46 is an estimation evaluation table relating to the combinations of the feature value when the sampling is performed at 4 kHz.

FIG. 47 is an estimation evaluation table relating to the combinations of the feature value with respect to all sampled data.

FIG. 48 is an estimation evaluation table relating to the combinations of the feature value when the sampling with high density is performed at 1 MHz to 125 kHz.

FIG. 49 is an estimation evaluation table relating to the combinations of the feature value when the sampling with low density is performed at 63 kHz to 4 kHz.

FIG. 50 shows a graph between the sampling frequency and the weighted mean relative error (weighted average) with respect to the combination of the top five types of feature values that can obtain the high number estimation accuracy when all the sampling data are used (50A) and when the sampling is performed with high density (50B).

FIG. 51 shows a graph (51A) between the sampling frequency and the weighted mean relative error (weighted average) with respect to the combination of the top five types of feature values that can obtain the high number estimation accuracy when the sampling is performed with low density, and a graph (51B) between the sampling frequency and the weighted average relative error (weighted average) with respect to the combination of the four types of feature values when all the sampling data are used.

FIG. 52 shows a graph (52A) between the sampling frequency (kHz) and the necessary calculation time (seconds) showing the total calculation time of the calculation time required for the feature value creation and the calculation time required for iterative calculation by Hasselblad method for each combination of four types of feature values, and a graph (52B) between the sampling frequency (kHz) and the necessary calculation time (seconds) showing the calculation time required for the feature value creation for each combination of the feature value.

BEST MODE FOR CARRYING OUT THE INVENTION

The number analyzing apparatus according to one embodiment of the present invention will be described below with reference to the drawings. In the present embodiment, there will be explained the particle number analyzing form for analyzing microbial particles such as bacteria as an example of the analyte.

Figure 1:
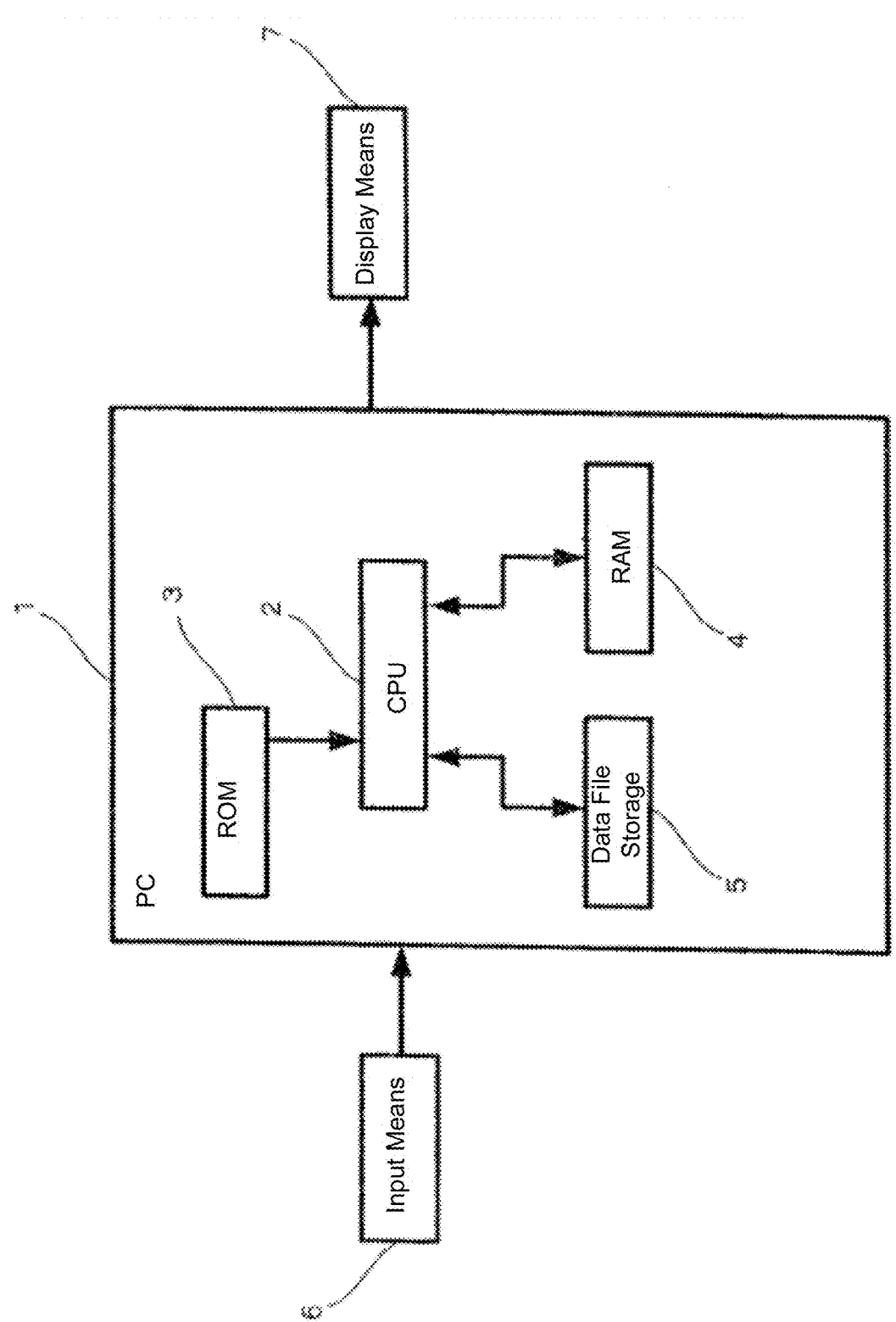
FIG. 1 is an outlined block diagram of the number analyzing device as an embodiment of the present invention.

FIG. 1 is an outlined block diagram of the number analyzing device as an embodiment of the present invention. This number analyzing device is constituted by a personal computer (hereinafter referred to as PC) 1, and the PC 1 has CPU 2, ROM 3, RAM 4 and a data file storage portion 5. A number analysis program according to the present invention is stored in the ROM 3. The number analysis program is installed and stored from a storage medium (CD, DVD, etc.) storing the program. Input means 6 such as a keyboard and display means 7 such as a liquid crystal display are connected to the PC 1 so as to be capable of inputting and outputting. The data file storage portion 5 is capable of storing number analysis data.

Figure 2:
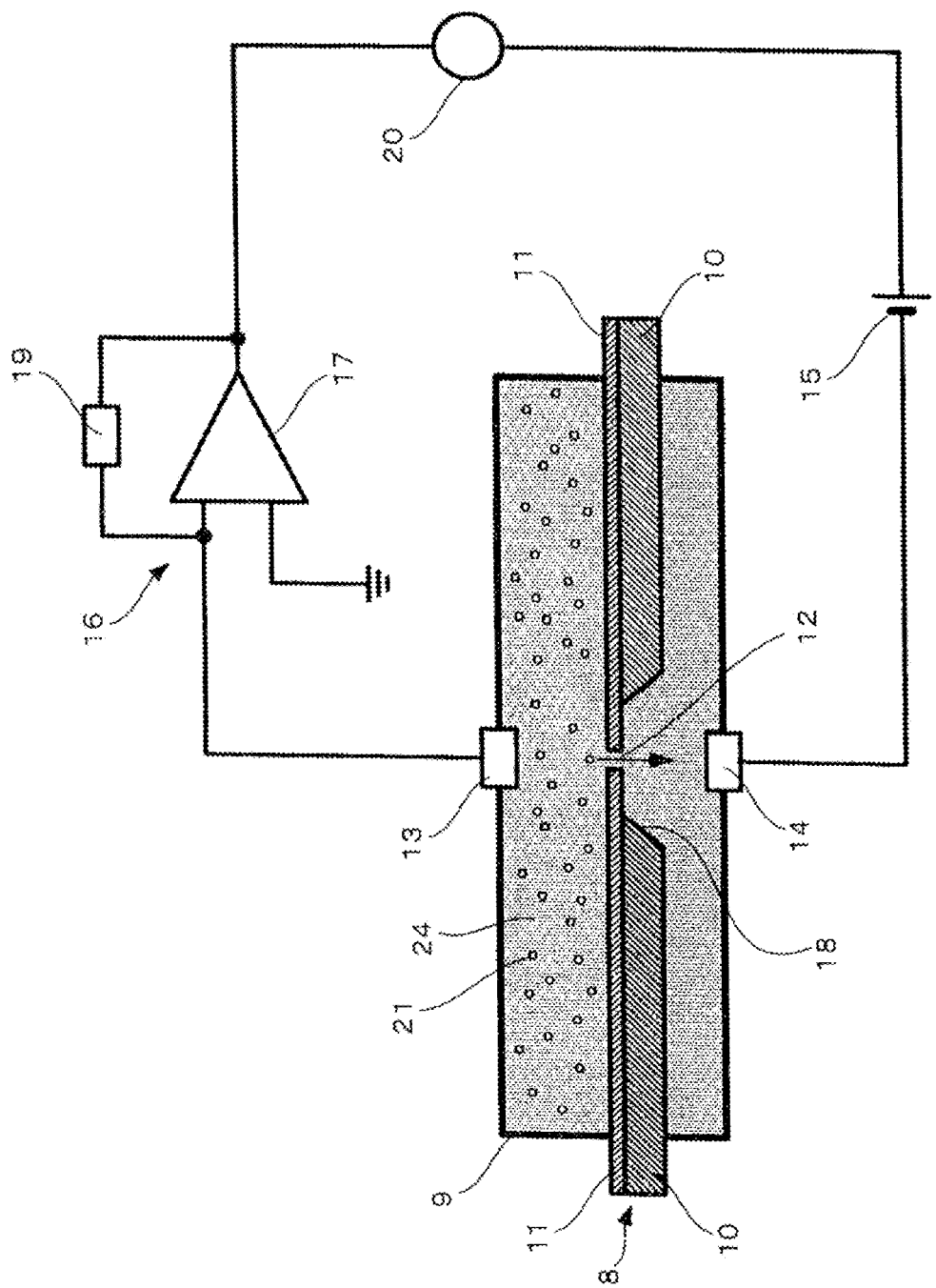
FIG. 2 is an outlined side sectional diagram showing the schematic configuration of the micro•nanopore device.

FIG. 2 shows the schematic configuration of the particle detection device using a micro•nanopore device 8.

The particle detection device is constituted by the micro•nanopore device 8 and an ionic current detection portion. The micro•nanopore device 8 has a chamber 9, a partition wall 11 partitioning the chamber 9 into upper and lower accommodation spaces, and a pair of electrodes 13, 14 arranged on the front and back sides of the partition wall 11. The partition wall 11 is formed on a substrate 10. A small through-hole 12 is formed in the vicinity of the center of the partition wall 11. Below the through-hole 12, a recess portion 18 is formed by removing a part of the substrate 10 downward in a concave shape.

The micro•nanopore device 8 is fabricated using a manufacturing technique (for example, an electron beam drawing method or photolithography) of a semiconductor device or the like. That is, the substrate 10 is made of Si material, and a partition wall 11 made of $Si_3N_4$ film is formed as a thin film on the surface. The recess portion 18 is formed by removing a part of the substrate 10 by etching.

The partition wall 11 is formed by laminating SiN film with 50 nm thickness on Si substrate having a size of 10 mm square and a thickness of 0.6 mm. A resist is applied to the $Si_3N_4$ film, and a circular opening pattern having a diameter of 3 μm is formed on it by an electron beam writing method, and the through-hole 12 is bored. On the back side of the through-hole 12, wet etching with KOH is performed to form a 50 μm square opening to provide the recess portion 18. The formation of the recess portion 18 is not limited to wet etching, but it can be performed by isotropic etching etc. using the dry etching with $CF_4$ gas or the like, for example.

In addition to the SiN film, the insulating film such as $SiO_2$ film, $Al_2O_3$ film, glass, sapphire, ceramic, resin, rubber, elastomer, or the like can be used for the film of the partition wall 11. The substrate material of the substrate 10 is not limited to Si, and glass, sapphire, ceramic, resin, rubber, elastomer, $SiO_2$, SiN, $Al_2O_3$, or the like can be used.

The through-hole 12 is not limited to the case of forming the thin film on the above substrate, and for example, by attaching a thin film sheet having the through-hole 12 onto the substrate, the partition wall having the through-hole may be formed.

The ionic current detection portion is constituted by an electrode pair of the electrodes 13 and 14, a power supply 15, an amplifier 16, and a voltmeter 20. The electrodes 13, 14 are arranged to face each other through the through-hole 12. The amplifier 16 is constituted by an operational amplifier 17 and a feedback resistor 19. The (−) input terminal of the operational amplifier 17 and the electrode 13 are connected. The (+) input terminal of the operational amplifier 17 is grounded. The voltmeter 20 is connected between the output side of the operational amplifier 17 and the power supply 15. The applied voltage of 0.05 to 1 V can be used between the electrodes 13 and 14 by the power supply 15, but in this embodiment, 0.05 V is applied. The amplifier 16 amplifies the current flowing between the electrodes and outputs it to the voltmeter 20 side. The electrode material of the electrodes 13 and 14 are, for example, Ag/AgCl electrode, Pt electrode, Au electrode or the like, preferably Ag/AgCl electrode can be used.

The chamber 9 is a flowable substance accommodation container which hermetically surrounds the micro•nanopore device 8, and can be made of electrically and chemically inert materials such as glass, sapphire, ceramic, resin, rubber, elastomer, $SiO_2$, SiN, $Al_2O_3$, or the like.

An electrolytic solution 24 containing the subject 21 is filled in the chamber 9 from an injection port (not shown). The subject 21 is, for example, an analyte such as a bacterium, a microparticulate substance, a molecular substance or the like. The subject 21 is mixed in the electrolytic solution 24 which is a flowable substance, and the measurement is performed by the micro•nanopore device 8. At the end of the measurement by the ion current detection portion, the filling solution can be discharged from the discharge port (not shown). As the electrolytic solution, for example, in addition to phosphate buffered saline (PBS), Tris-EDTA (TE) buffer and dilution solutions thereof, all electrolytic solution agents similar thereto can be used. The measurement is not limited to the case in which it is always performed when the subject-containing electrolytic solution is introduced into the chamber 9 and filled. The subject-containing electrolytic solution (flowable substance) is pumped out from the solution reservoir by a simple pumping device and injected from the injection port into the chamber 9 and discharged from the discharge port after the measurement. Furthermore, new solution is stored in the solution reservoir or another solution reservoir, and newly pumped out to perform next measurement, so that the continuous measurement system can be constituted.

When a voltage from the power source 15 is applied between the upper and lower electrodes 13, 14 of the through-hole 12 in a state where the electrolytic solution 24 is filled in the chamber 9, a constant ion current proportional to the through-hole 12 flows between the electrodes. When a subject such as bacteria etc. existing in the electrolytic solution 24 passes through the through-hole 12, a part of the ion current is inhibited by the subject, so that the pulsed ion current reduction can be measured by the voltmeter 20. Therefore, according to the particle detecting device using the micro•nanopore device 8, by detecting the change in the waveform of the measured current, it is possible to detect each individual presence of the particles contained in the flowable substance by passing through the through-hole 12 for each subject (for example, particle) with high accuracy. The measurement mode is not limited to the case where the measurement is performed while forcibly flowing the flowable substance but can include a case of measurement while flowing the flowable substance non-forcibly.

The measurement output of the ion current by the voltmeter 20 can be externally outputted. The external output is converted into digital signal data (measured current data) by a conversion circuit device (not shown), temporarily stored in a storage device (not shown), and then stored in the data file storage portion 5.

In the number analyzing device according to the present embodiment, a flowable substance (electrolytic solution 24) containing one or more kinds of particles (an example of analyte) as an analysis target is supplied to one side of the partition wall 11, and it is the number analyzing method which can analyze the number of each particle type and the number distribution by executing a computer control program (number analysis program) on the basis of data (measured current data) of detection signals that has detected the change in electric conduction between the electrodes 13, 14 caused by passing through the through-hole 12, so that the automatic analysis of the number of each particle type can be performed. By executing the number analysis program stored in ROM 3 under the control of CPU 2, the PC 1 can perform the number analysis process on the measured current data stored and remembered in the data file storage portion 5.

Figure 3:
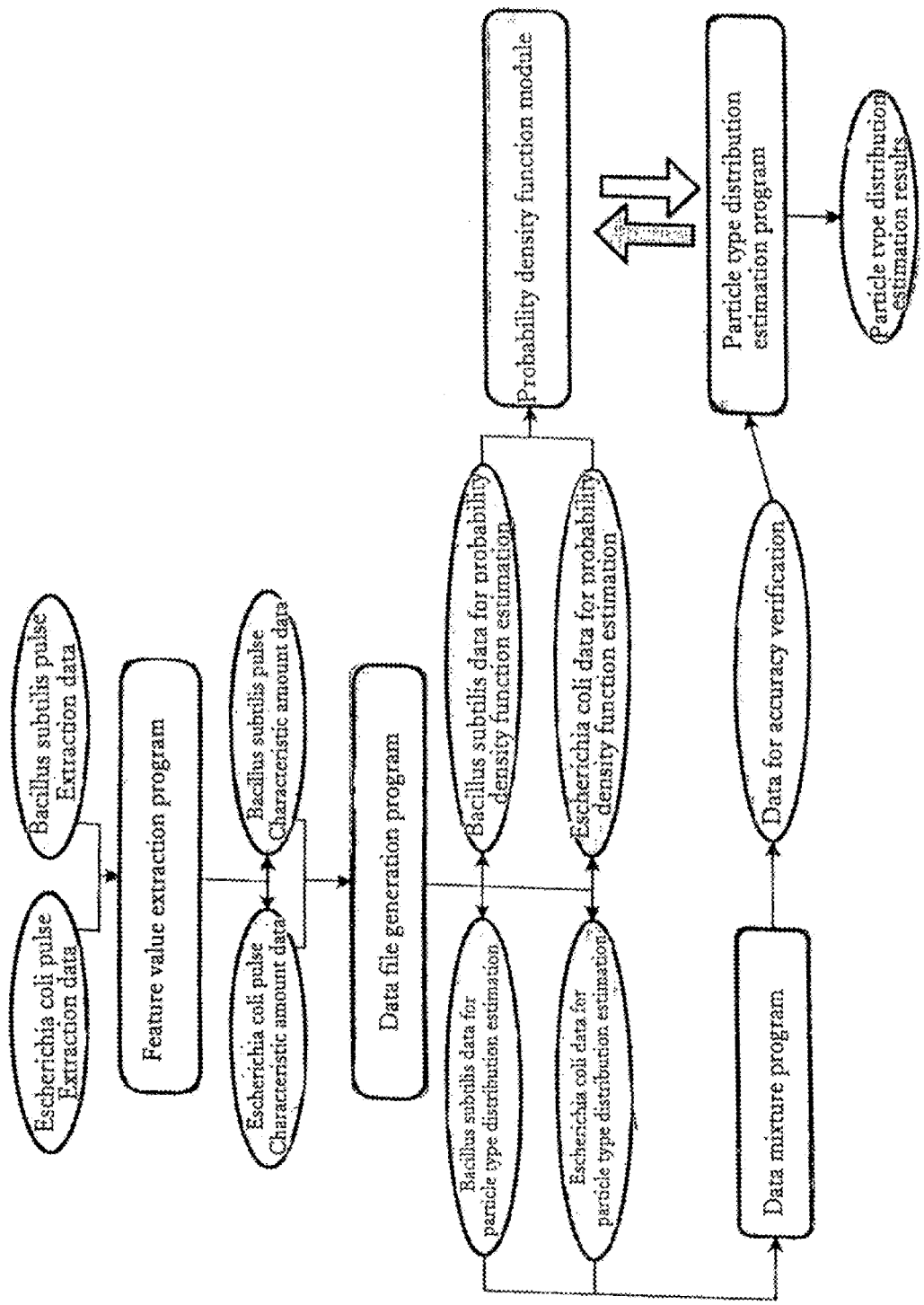
FIG. 3 is a diagram showing a processing program configuration necessary for explaining the number analyzing process that can be executed by PC 1 of the number analyzing device.

FIG. 3 shows the processing program configuration necessary for explaining the number analyzing process that can be executed by PC 1. As an example of data of the analysis target, the measured current data (pulse extraction data of each particle) extracted using the electrolytic solution 24 including two types of particles (*Escherichia coli* and *Bacillus subtilis*) as analytes is used as original data.

The number analysis program includes the probability density function module program for obtaining the probability density function from the data group based on the feature value indicating the feature of the waveform form of the pulse signal corresponding to the particle passing through the through-hole 12 obtained as the detection signal, and the particle type distribution estimation program for deriving the number of each particle type from the result of the probability density estimation. Furthermore, the number analysis program includes the feature value extraction program for extracting the feature value indicating the feature of the waveform of the pulse signal with reference to the baseline extracted from the data group, and the data file creation program for creating the data file due to the pulse feature value data for each particle obtained based on the extracted feature value. The probability density estimation process and the particle number derivation process for each particle type can be executed on the scalar data of the feature value fetched from the data file created by the data file creation program. The feature value extraction program includes the baseline estimation process program for extracting the baseline from the original measured current data.

Since the form of the true probability density function is unknown as the premise of particle type distribution estimation, the execution of the probability density function module program performs the nonparametric (not specifying the functional form) probability density estimation called Kernel method. The original data of the estimation target is the pulse appearance distribution data including, for example, a pulse height h, a time width Δt, an appearance number, etc. obtained from the pulse signals. Each data of the original measurement data distribution is expressed by a Gaussian distribution introducing measurement error uncertainty, and a probability density function is obtained by superimposing each Gaussian distribution. The probability density estimation process is performed by executing the probability density function module program and the original data can be represented by an unknown complex probability density function based on the original data (for example, pulse height, pulse width, appearance probability of the feature value).

Figure 33:
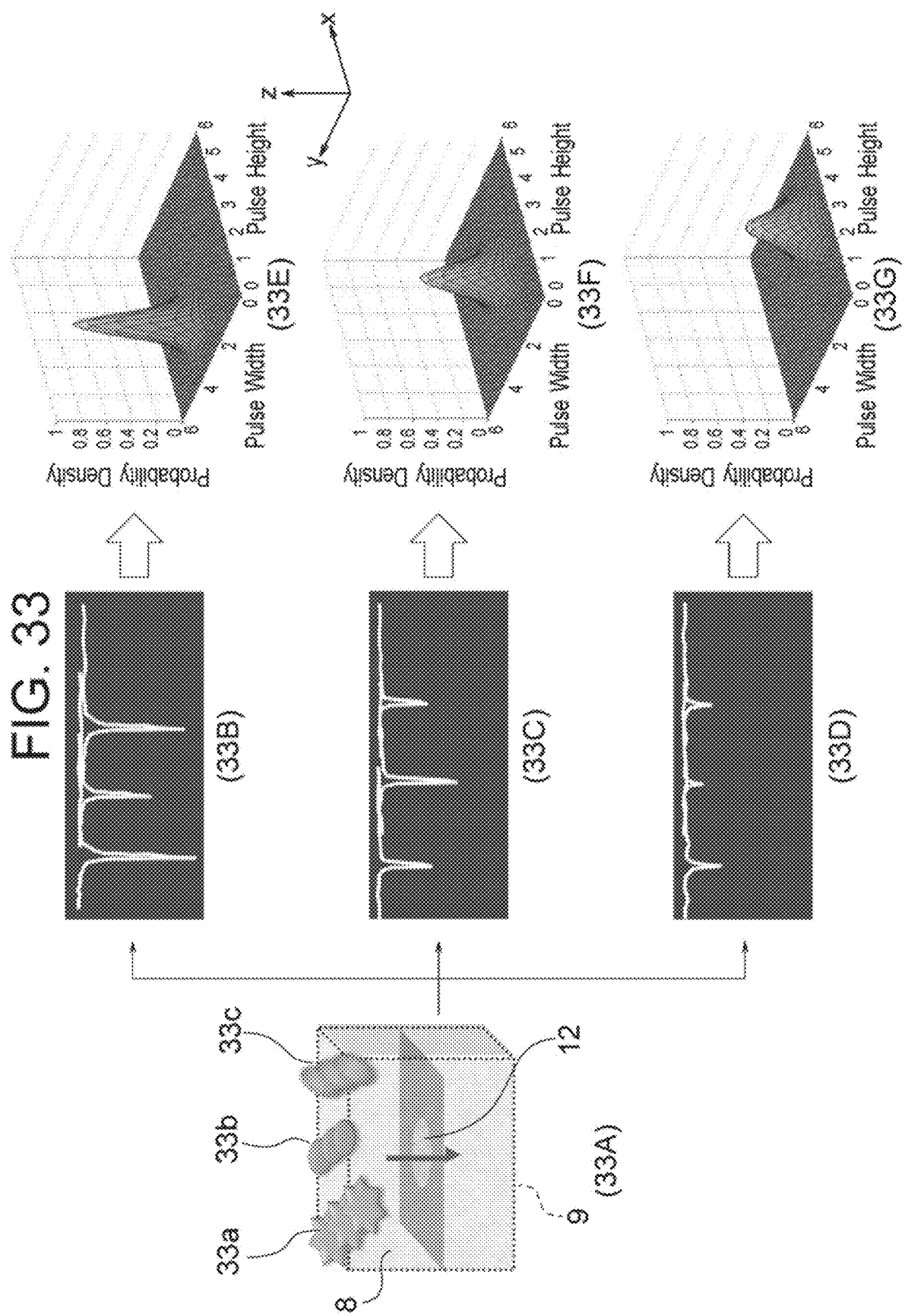
FIG. 33 is a diagram which shows an example of waveform of detection signals obtained by using the micro•nanopore device 8 when three types of particles 33a, 33b, and 33c pass through the through-hole 12 and shows a deriving example of the probability density function obtained based on the feature values.

FIG. 33 shows the examples of waveform of detection signals obtained by using the micro•nanopore device 8 when three types of particles 33a, 33b, and 33c pass through the through-hole 12 and shows the deriving examples of the probability density function obtained based on the feature values. FIG. 33A) schematically shows the particle detection device using the micro•nanopore device 8. FIGS. (33B)-(33 D) show the waveform data of each detection signal. FIGS. (33E) to (33G) show the three-dimensional distribution diagram of the probability density function obtained from each waveform data. The x-axis, y-axis, and z-axis in (33E)-(33G) indicate the pulse height and the pulse width of the feature value, and the probability density obtained by the probability density estimation, respectively.

In the present embodiment, as described above, the probability density estimation process is performed based on the Kernel method which is one of estimation methods of the nonparametric density function. The Kernel method is an estimation method in which a function (Kernel function) at one data point is applied, this is applied to all data points, and the arranged functions are superimposed, which is suitable for obtaining a smooth estimation value.

By executing the probability density function module program and by considering the multivariable multidimensional probability density from data such as pulse wave height, pulse width, etc. of the measured current waveform, the weighted optimum estimation is performed extending to two or more dimensions and the estimation process of the particle type number distribution is performed. EM algorithm software executed based on Hasselblad iteration method is used for the weighted optimum estimation. The EM algorithm is preinstalled in the PC 1. The particle type number distribution result obtained by the estimation process of the particle type number distribution can be output and displayed as the histogram of appearance frequency (number of particles) for each particle type on the display means 7.

The feature value according to the present invention is, as the parameters derived from the pulse signal, either of first type showing local feature of waveforms of said pulse signals and second type showing global feature of waveforms of said pulse signals. By carrying out the number analysis using one or two or more of these feature values, it is possible to analyze the number or number distribution corresponding to the type of analyte such as particle type etc. with high accuracy.

Figure 11:
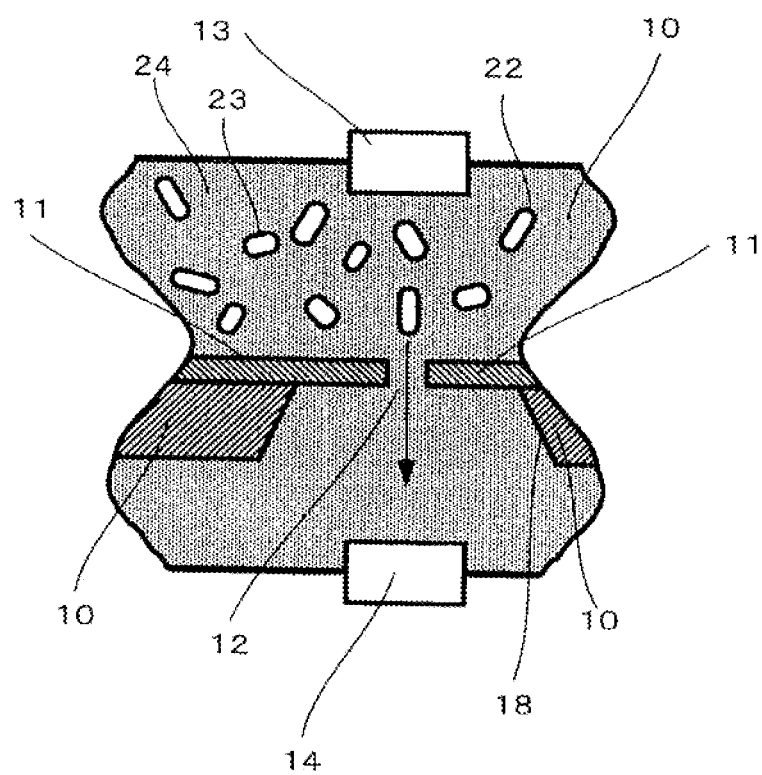
FIG. 11 is an enlarged diagram of a periphery of through-hole 12 schematically showing a state in which *Escherichia coli* 22 and *Bacillus subtilis* 23 are mixed in the electrolytic solution 24.

FIG. 11 is an enlarged diagram of a periphery of through-hole 12 schematically showing a state in which two kinds of particles such as *Escherichia coli* 22 and *Bacillus subtilis* 23 are mixed in the electrolytic solution 24.

<About Feature Values>

Figure 4:
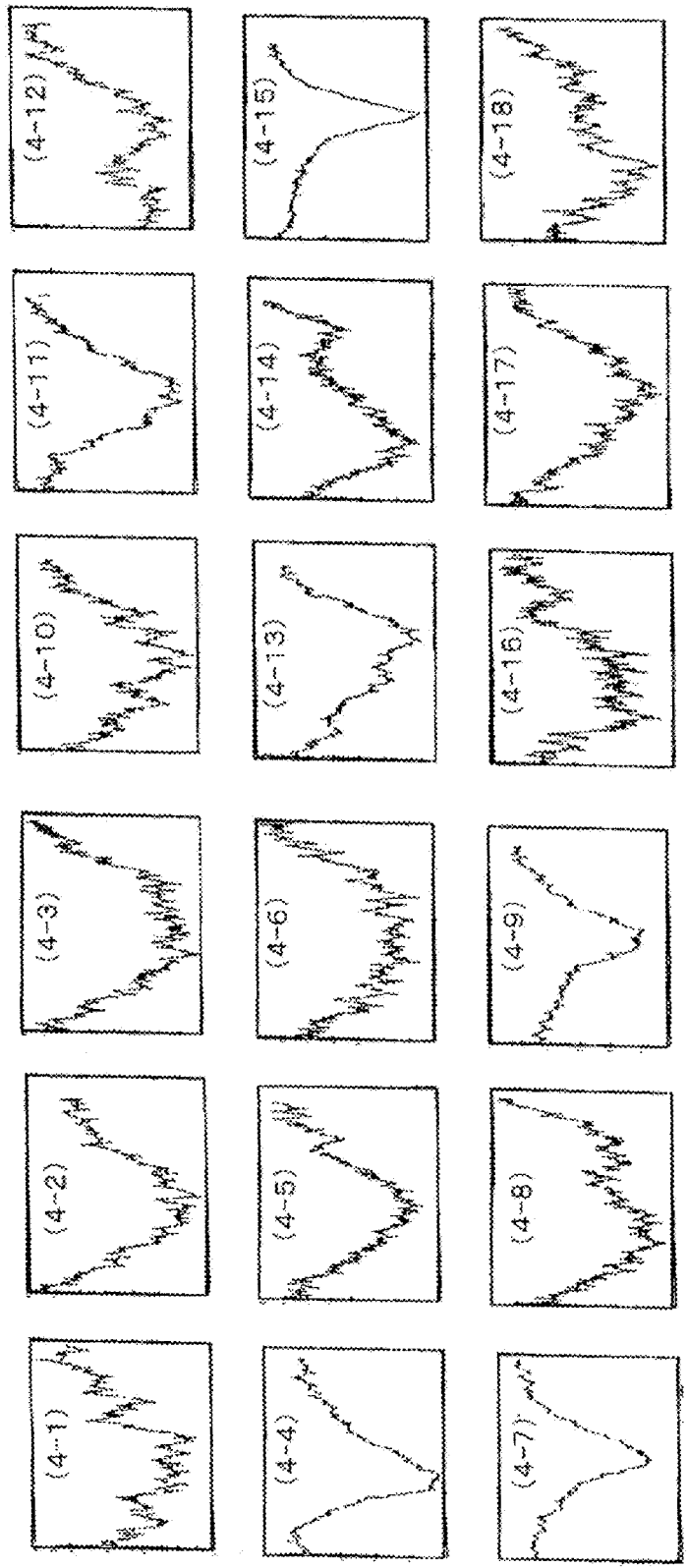
FIG. 4 is a diagram showing examples of pulse waveforms obtained by particle passage actually measured for *Escherichia coli* (*E. coli*) and *Bacillus subtilis* (*B. subtilis*) as examples.

FIG. 4 shows an example of the pulse waveform due to particle passage measured for *Escherichia coli* (*E. coli*) and *Bacillus subtilis* (*B. subtilis*) in examples. The (4-1) to (4-9) of FIG. 4 show the examples (9 kinds) of measured pulse waveforms of *E. coli*, and (4-10) to (4-18) show the examples of measured pulse waveforms of *B. subtilis* (9 kinds). When comparing both types in appearance, there is not much difference in the wave height and the wavelength between both types, but there are remarkable differences in attributes of pulse waveform of particle passage such as the peak position and the waveform kurtosis. For example, in the case of *Escherichia coli*, the peak tends to go ahead with the lapse of time and the waveform is sharp in a whole (waveform kurtosis is large). In the case of *Bacillus subtilis*, the peak tends to fall down backwards with the lapse of time and the waveform kurtosis is small.

The present inventors focused on extracting the feature values used as a base for creating the probability distribution for each particle type (*E. coli* and *B. subtilis*) from the pulse waveform data on the basis of the difference of the attribute of the pulse waveform of particle passage.

Figure 5:
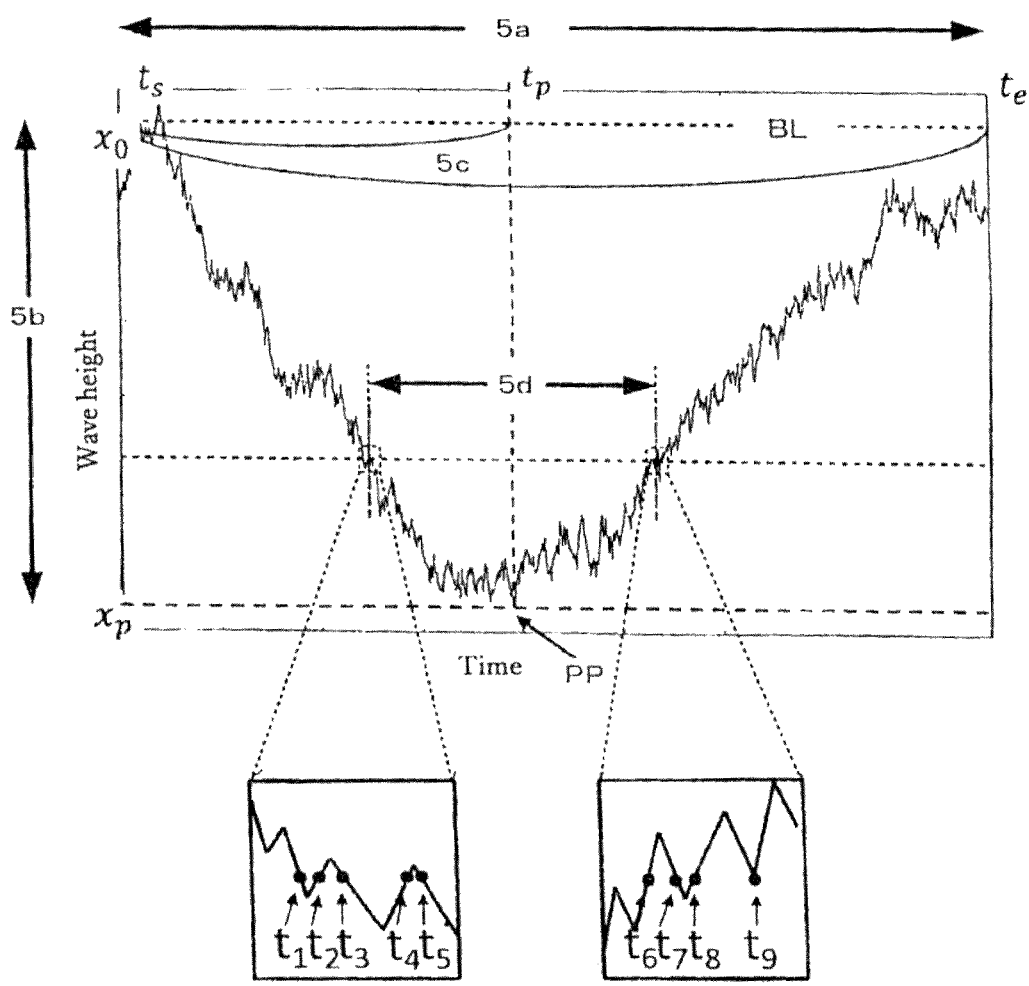
FIG. 5 is a pulse waveform diagram for explaining various types of feature value according to the present invention.

FIG. 5 is a pulse waveform diagram for explaining various types of feature values according to the present invention. In FIG. 5, the horizontal axis shows the time and the vertical axis shows the pulse wave height.

The feature value of the first type is one selected from a group of the wave height value of the waveform in a predetermined time width, the pulse wavelength $t_a$, the peak position ratio represented by ratio $t_b/t_a$ of time $t_a$ and $t_b$ leading from the pulse start to the pulse peak, the kurtosis which represents the sharpness of the waveform, the depression representing the slope leading from the pulse start to the pulse peak, the area representing total sum of the time division area dividing the waveform with the predetermined times, and the area ratio of sum of the time division area leading from the pulse start to the pulse peak to the total waveform area.

The 5*a* to 5*d* in FIG. 5 indicate the pulse wavelength, the wave height value, the peak position ratio, and the kurtosis, respectively. The BL in FIG. 5 indicates the base line (hereinafter referred to as the base line) extracted from the pulse waveform data (refer to BL extraction process to be described later). These four kinds of pulse feature values are defined by the following (1) to (4) on the basis of FIG. 5.

(1) Wavelength (pulse width) $\Delta t: \Delta t = t_e - t_s$ ($t_s$ is the start time of the pulse waveform, $t_e$ is the end time of the pulse waveform, $\Delta t = t_a$).

(2) Wave height $|h|: h = x_p - x_o$ (the height of pulse waveform up to $x_p$ of the pulse peak PP with reference to $x_o$ of BL).

(3) Peak position ratio $r: r = (t_p - t_s)/(t_e - t_s)$ (the ratio of the time $t_b = (t_p - t_s)$ from the pulse start to the pulse peak pp to the pulse wavelength ($=\Delta t$)).

(4) Peak kurtosis $\kappa$: It is normalized so as that the wave height $|h| = 1$, $t_s = 0$ and $t_e = 1$ hold, and there are collected the time set $[T] = [[ti]|i=1, \ldots, m]$ which is the time crossing the horizontal line of 30% in wave height from the pulse peak PP, and then the $\kappa$ is obtained so that the dispersion of the data of the time set $[T]$ is calculated as the pulse waveform spread as shown in the following equation 1.

$$\kappa = \frac{1}{m}\sum_{i=1}^{m}(t_i - ave[t])^2 \qquad \text{[Equation 1]}$$

FIG. 34 is the pulse waveform diagram for explaining the feature values of the depression, the area and the area ratio. In FIG. 34, the horizontal axis represents the time and the vertical axis represents the pulse wave height. These three kinds of pulse feature values are defined by the following (5), (6) and (7) on the basis of FIG. 34.

(5) As shown in (34 A), the depression θ is the slope leading from the pulse start to the pulse peak and is defined by the following equation 2.

$$\theta = \arctan\left(\frac{t_p - t_s}{h}\right) \qquad \text{[Equation 2]}$$

(6) The area m is defined as the area [m] by the inner product of the unit vector [u] and the wave height vector [p] as shown in the following equation 3. In the following description, the vector notation of variable A is indicated by [A]. For example, as shown in the 10-division example of (34 B), the area m is the area representing the total sum of the time division area hi ($h_i = h_x \times h_y$, i=1 to 10 when width $h_x$ and height $h_y$).

$$m = (u, p) = \Sigma_i 1 \cdot h_i \qquad \text{[Equation 3]}$$

Here, it is necessary to calculate and obtain the d-dimensional wave height vector $[p](=(h1, h2, \ldots h_d))$ in advance as preparation for the feature value calculation.

Figure 35:
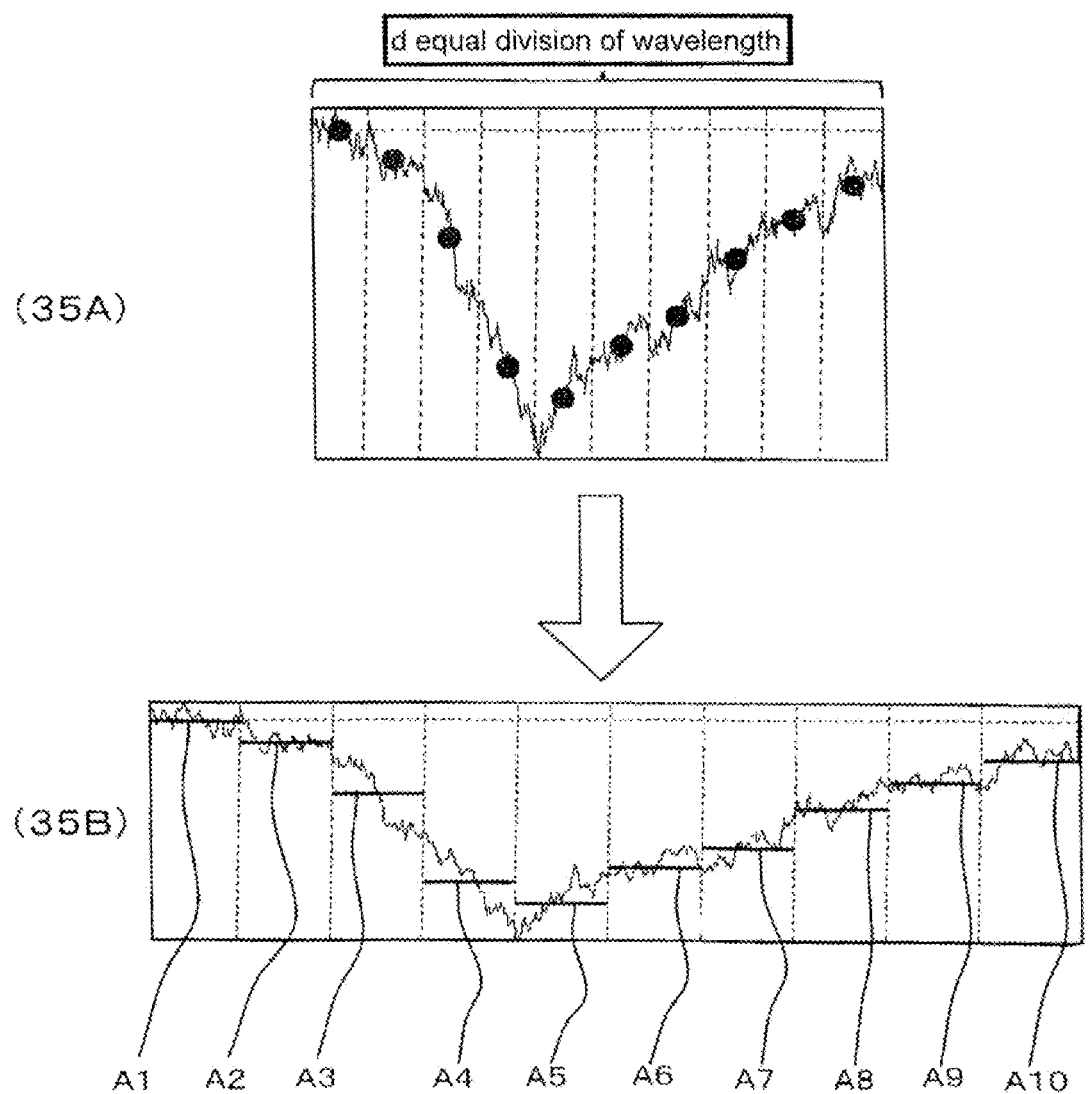
FIG. 35 is a diagram for explaining the manner obtaining the wave height vector.

FIG. 35 is the diagram for explaining the manner obtaining the wave height vector.

As shown in (35 A), by equally dividing the wavelength into d number for one waveform data, the d number of data groups are differentiated. Next, as shown in (35B), the values of wave height are averaged for each group (each divided interval), for example, when dividing equally into 10, the average values A1 to A10 are obtained. This averaging can include a case where the wave height value is not normalized and a case where the wave height value is normalized. The area [m] described by equation 3 indicates a case where the normalization is not performed. The d-dimensional vector having the average values thus determined as components is defined as a "wave height vector".

Figure 36:
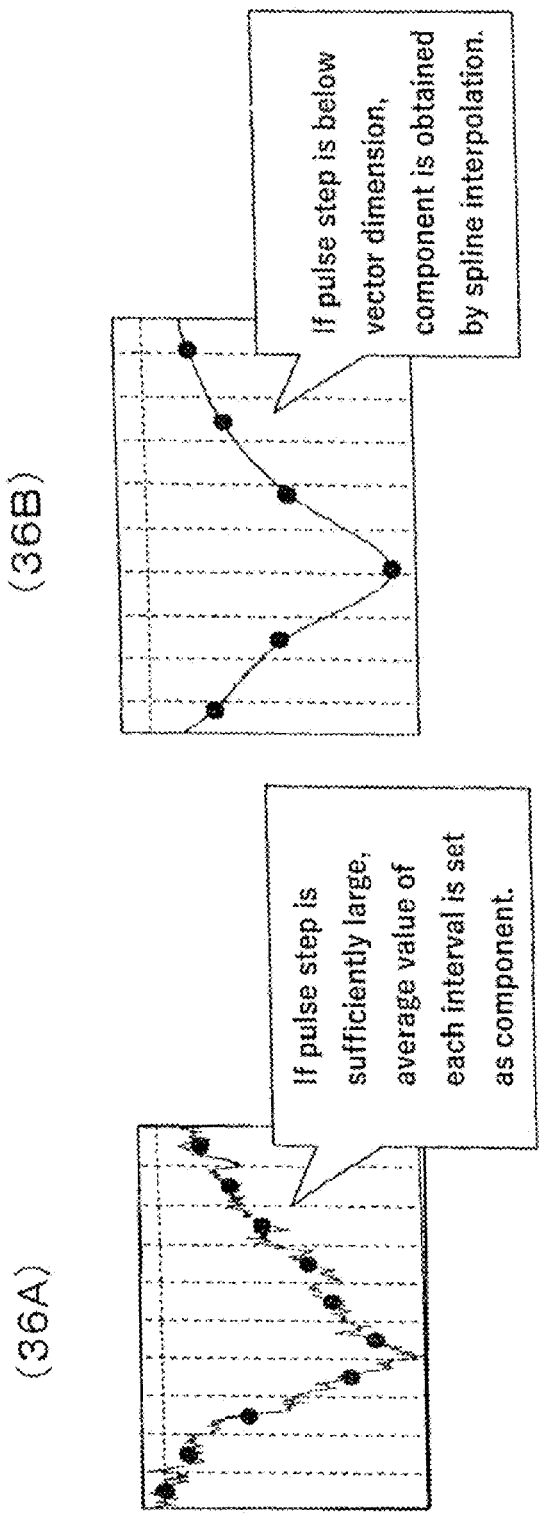
FIG. 36 is a diagram for explaining the relationship between the d-dimensional wave height vector and the data sampling.

FIG. 36 is a diagram for explaining the relationship between the d-dimensional wave height vector and the data sampling.

As shown in (36 A), when the sampling rate related to acquisition of pulse data is large, since the number of steps (number of data) T in the pulse part exceeds the dimension number d of the vector, by the above acquisition steps, it is possible to obtain the wave height vector of which component is the average of each section. On the other hand, as the sampling rate is lowered, the number of steps T in the pulse part falls below the dimension number d (>T) of the vector. In the case of T<d, since the average value of each section cannot be acquired by the acquisition procedure described above, it is possible to acquire the d-dimensional wave height vector by cubic spline interpolation.

The feature value extraction program includes the wave height vector acquisition program for acquiring wave height vector data. In the case where the pulse step number T exceeds the dimension number d of the vector (T>d) (T=d) by executing the wave height vector acquisition program, the average value of each division equally divided in the time direction is obtained, In the case where the pulse step number T is smaller than the dimension number d of the vector (T<d), a cubic spline interpolation is executed to obtain the d-dimensional wave height vector. That is, by performing the interpolation process using the cubic spline interpolation method, even when the number of pulse steps is small, the number of dimensions of the vector can be made constant.

(7) The area ratio $r_m$ is defined as the area ratio of the sum of the time interval area $h_t$ shown in (34B) in the section leading from the pulse start to the pulse peak to the total waveform area. The following Equation 4 shows the area ratio $r_m$.

$$r_m = \Sigma_{t<t_p} h_t / \Sigma h_t \quad \text{[Equation 4]}$$

The feature value of the first type is uniquely derived from the waveform of the pulsed signal such as the pulse wave height, the pulse wavelength, the pulse area and the like, so that it is the feature value showing the local feature. The second type of the feature value is the feature value indicating the global feature with respect to the first type of the local feature.

The second type of the feature value is one selected from a group of the time inertia moment determined by mass and rotational radius when the mass is constructive to said time division area centered at the pulse start time and the rotational radius is constructive to time leading from said center to said time division area, the normalized time inertia moment when said time inertia moment is normalized so as that the wave height becomes a standard value, the wave width mean value inertia moment determined by mass distribution and rotational center when the mass distribution is constructive to mean value difference vector whose vector component is mean value difference of the same wave height position in which the wave form is equally divided in the wave height direction and the mean value of time values is calculated for each division unit in before and after each pulse peak and the rotational center is constructive to time axis of waveform foot, the normalized wave width mean value inertia moment when said wave width mean value inertia moment is normalized so as that the wavelength becomes a standard value, the wave width dispersion inertia moment determined by mass distribution and rotational center when the mass distribution is constructive to dispersion vector whose vector component is dispersion in which the wave form is equally divided in the wave height direction and the dispersion is calculated from time value for each division unit and the rotational center is constructive to time axis of waveform foot, and, the normalized wave width dispersion inertia moment when said wave width dispersion inertia moment is normalized so as that the wavelength becomes a standard value.

FIG. 37 is the pulse waveform diagram for explaining the feature value of the inertia moment with respect to the time (wavelength) and the wave width.

In FIG. 37, the horizontal axis represents the time and the vertical axis represents the pulse wave height. These pulse feature values are defined by the following (8), (9), (10), (11), (12), and (13) as shown in FIG. 37.

(8) The time inertia moment, as in (34 B), is the feature value determined by mass and rotational radius when the mass is constructive to the time division area $h_i$ formed by equally dividing one waveform in i-dimension with a predetermined time interval and the rotational radius is constructive to the time leading from the center to the time division area $h_i$. That is, the feature value of the time inertia moment is defined by [I] which is the inner product of the vector [v] and the wave height vector [p] as shown in the following equation 5. Here, when the dimension of the vector is n, $[v]=(1^2, 2^2, 3^2, \ldots, n^2)$ and $[p]=(h_1, h_2, \ldots, h_d)$. For example, the time inertia moment, as shown in the example of 10 divisions of (37 A), is the feature value determined when the time division area $h_i$ ($h_i=h_x \times h_y$, i=1 to 10 with width $h_x$ and height $h_y$) is regarded as the mass and the time leading from the center to the time division area $h_i$ is regarded as the turning radius, where one waveform is divided into 10 with a predetermined time-interval as in (34 B), so that in the same manner of the area m of (6), it can be obtained from the wave height vector.

$$I = (v, p) = \Sigma_i i^2 \cdot h_i \quad \text{[Equation 5]}$$

(9) The normalized time inertia moment is calculated by using the waveform normalized in the wave height direction in which the wave height becomes the reference value "1" for the waveform for which the time division area is created as shown in (8), and is the feature value defined by equation 5 using the wave height vector $h_i$ in the same manner shown in (8).

(10) The wave width mean value inertia moment is, as shown in 10 division example of (37B), obtained by equally dividing one waveform into i-dimensions in the wave height direction in the same way as in (8) and by calculating the mean value of time values for each division unit (divided region $w_i$) in before and after the pulse peak, so that the difference vector of the mean value having the difference of the mean value of the same wave height positions in the divided region $w_i$ as the components of the vector is regarded as the mass distribution $h_i$ (the dimension number of the vector is n, i=1 to n) and it is the feature value defined as the moment of inertia when the time axis At of the waveform foot is to be the rotation center. The definition formula is the same as equation 5, and the feature value of (10) can be obtained by the inner product of the vector [v] and the mass distribution $h_i$.

(11) The normalized wave width mean value inertia moment is the feature value which uses the waveform normalized in the wavelength direction in which the wavelength becomes the reference value "1" for the waveform creating the divided region $w_i$ shown in (10) and is the feature value defined by equation 5 using the mass distribution $h_i$ created through the same way as in (10).

(12) The wave width dispersion inertia moment, similar to the wave width mean value inertia moment, is obtained by equally dividing one waveform into i-dimensions in the wave height direction and by calculating the dispersion from the time values for each division unit (divided region Iv) in before and after the pulse peak, so that the dispersion vector having the dispersion as the components of the vector is regarded as the mass distribution $h_i$ (the dimension number of the vector is n, i=1 to n) and it is the feature value defined as the moment of inertia when the time axis At of the waveform foot is to be the rotation center, and this feature value is defined by equation 5, in the same manner as the wave width mean value inertia moment.

(13) The normalized wave width dispersion inertia moment is the feature value which uses the waveform normalized in the wavelength direction in which the wavelength becomes the reference value "1" for the waveform creating the divided region $w_i$ shown in (12) and is the feature value defined by equation 5 using the mass distribution $h_i$ created through the same way as in (12).

The wave width mean value inertia moment and the wave width dispersion inertia moment are the feature values defined by equation 5 as described above, and the vector [p] in the definition is the difference vector of mean values of the time values in the case of the wave width mean value inertia moment, and the dispersion vector of the time values in the case of the wave width dispersion inertia moment. In the following description, the vector [p] in the moment of inertia with respect to the wave widths of (10) to (13) is expressed as $[p_w]$.

For the creation of moment of inertia with respect to the wave widths of (10) to (13), there is performed using the wave width vector [pw] (=$[p_1, p_2, \ldots, p_{dw}]$) in which the vertical and horizontal axes of the wave height vector shown in FIG. 36 are exchanged.

The wave width vector is the difference vector or the dispersion vector of the mean value shown in the definition of the feature value of (10) to (13). By grasping the wave width vector as the density distribution, the wave width mean value inertia moment of (10) and (11) and the wave width dispersion inertia moment of (12) and (13) can be obtained. The wave width vector is the $d_w$ dimensional vector, for which the pulse waveform data is equally divided with $d_w$ dimensions in the wave height direction and whose components are the difference or dispersion of the mean values of the peak values obtained for each division. In the case of (37B), the dimension of the wave width vector is 10 dimensions. The time axis At shown in (37B) is different from the base line BL, and is the rotation axis line around the pulse foot obtained from the wave width vector.

FIG. 38 is the diagram for explaining the relation between the wave width vector of $d_w$ dimension and the data sampling.

The feature value extraction program includes the wave width vector acquisition program for acquiring the wave width vector by the creation calculation processing of the wave width vector of the following $d_w$ dimension.

Since the pulse waveform data distribute at various intervals in the wave height direction, there may be cases that it is contained one or more non-existent regions Bd in which data points do not exist in the section divided in the wave height direction. In (38A), an example of the non-existent region Bd is indicated by an arrow. In the non-existent region Bd, the data points do not exist because the data interval becomes coarse, so that it is impossible to obtain the component of the inertia moment with respect to the wave width defined by the above equation 6. Therefore, as in the case of the above-described pulse waveform spread, when the wave height to the pulse peak is equally divided by $d_w$, the time set [Tk]=$[[t_i]|i=1, \ldots, m]$ of each wave height is collected and the components of the wave width vector are created. At this time, in the non-existent region Bd in which no data point exists, the component data is acquired by the linear interpolation. The linear interpolation is performed on two consecutive data that extends over the values of (10k+5)% (k=0, 1, 2, 3, . . . ) of the pulse peak. The (38B) shows an example of the linear interpolation point $t_k$ with respect to the height k of the non-existent region Bd occurring between the data points $t_i$ and $t_{i+1}$. In the creation of the wave width vector, as shown in (38 C), when a discrepancy of the wave height data occurs in the foot region UR of the pulse waveform data, the wave height data Du on the side far from the pulse peak is truncated to align to the side close to the pulse peak. The execution process of the wave width vector acquisition program includes the linear interpolation process for the non-existent area Bd and the truncation process of the pulse height data Du for the discrepancy of the pulse height data.

FIG. 39 is the diagram for explaining the acquisition process of acquiring the inertia moment with respect to the wave width from the wave width vector.

The (39A) is the example in which the waveform is equally divided into ten intervals in the wave height direction, and there are shown the division region 39 *b* of the wave width vector and the rotation axis line 39*c* which are obtained by performing the above linear interpolation process and the truncation process for one waveform 39.

As shown in (39 B), for each division unit, the mean value of the time values is calculated before and after the pulse peak, and there can be obtained the wave width vector which is the difference vector of the mean value having the difference of the mean value at the same wave height position in the divided region as the component of the vector. By regarding this difference vector of the mean value as the mass distribution, the wave width mean value inertia moment of (10) with the rotation axis line 39*c* (time axis) as the rotation center can be created. Further, by calculating the dispersion from the time value of each division unit, it is possible to obtain the dispersion vector having the dispersion as the component of the vector. By regarding this dispersion vector as the mass distribution, it is possible to create the wave width dispersion inertia moment of (12) using the rotation axis line 39 *c* (time axis) as the rotation center.

The second type of feature value is not limited to the six kinds described above but may include, for example, the mean value vector determined by calculating the mean value of time values and the feature value normalizing it. As shown in the 10 divisions example of (37B), the mean value vector is obtained by equally dividing one waveform to the i dimensions in the wave height direction and calculating the mean value of the time values for each division unit (divided region $w_i$) before and after the pulse peak, so that the mean value of the same wave height position in the divided region $w_i$ is the components of the vector. The feature value obtained by normalizing the mean value vector is the feature value when the wavelength is normalized so as to be the reference value with respect to the mean value vector. Further, the vector dimension number of the wave height vector and the wave width vector used for creating the feature value need not be limited to the division number but can be arbitrarily set. The wave height vector and the wave width vector are obtained by dividing in one direction of the wavelength or the wave height, but the vectors which are divided into a plurality of directions can be used for creating the feature value.

Figure 40:
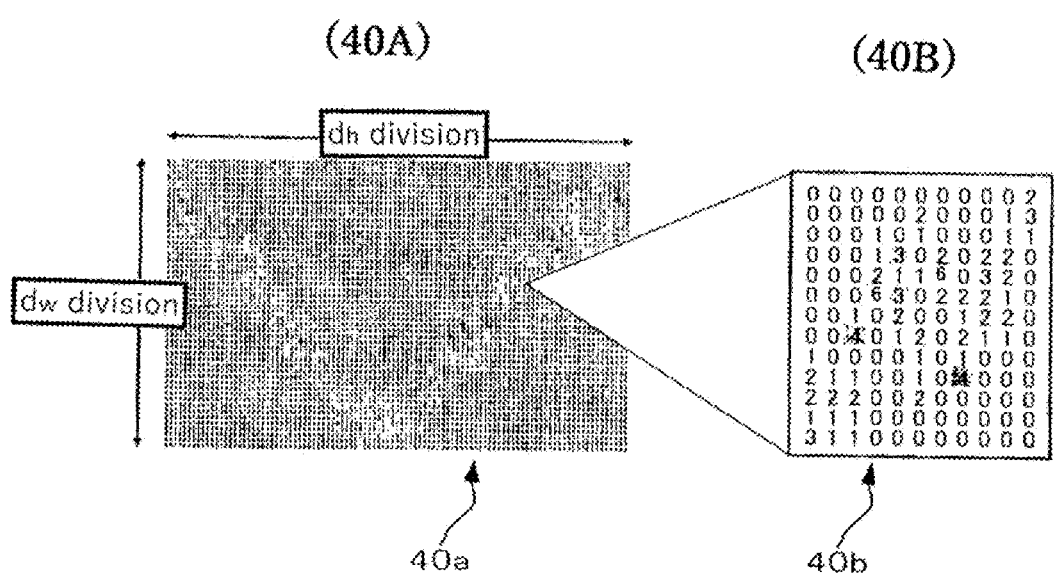
FIG. 40 is a diagram for explaining an example of the waveform vector for creating the feature value in the case divided into a plurality of directions.

FIG. 40 is the diagram for explaining an example of the waveform vector for creating the feature value in the case divided into a plurality of directions.

The (40A) shows the data map 40a obtained by dividing one waveform data into the mesh shape. The data map 40a shows the distribution state of the number of data points in the matrix form by dividing the waveform data with the $d_n$ division in the time axis direction of the horizontal axis and the $d_w$ division in the wave height direction of the vertical axis. The (40B) shows the distribution state in which a part of the matrix-like section (lattice) is enlarged. In the distribution state of (40 B), 0 to 6 data points are distributed in 11×13 grids. By this matrix division, the waveform vector in which the number of data points in each lattice/the total number of data points is a component of the $d_n \times d_w$ dimensional vector is converted into a vector in which data groups of the matrix array are rearranged in a scanning manner, so that it is possible to create the feature value instead of the wave height vector and the wave width vector.

<About Estimation of Base Line>

Generally, bacteria or the like are minute objects having finely the different forms. For example, in the case of average *Escherichia coli,* the body length is 2 to 4 μm and the outer diameter is 0.4 to 0.7 μm. In the case of the average *Bacillus subtilis,* the body length is 2 to 3 μm and the outer diameter is 0.7 to 0.8 μm. In addition, flagella of 20 to 30 nm are attached to *Escherichia coli* and the like.

When using bacteria or the like as subject particles, if slight differences are missed from the pulse waveform data, the number judgment accuracy will be lowered. For this reason, in order to accurately calculate the feature value and use it as the estimation basis of the probability distribution, it is necessary to accurately grasp the particle passage pulse wave height. For this purpose, it is necessary to estimate the base line of the measurement signal However, because the base line of the original data of the measurement signal contains fluctuations due to noise data and weak measured current, the pulse wave height and the like need to be detected after the base line excluding the fluctuation component etc. is determined. It is preferable that the base line estimation (hereinafter referred to as BL estimation) is practiced online (instantly) by the computer in practice.

As a method for estimating BL on a computer, by using the Kalman filter suitable for estimating the amounts that change from moment to moment from observations with discrete errors, the disturbances (system noise and observation noise) are removed, the base line BL can be estimated.

The Kalman filter is a method for estimating the value at the time [t] of updatable state vector [x], in which the discrete control process is defined by the linear difference equation shown in (6A) of FIG. 6. In the Kalman filter, the values of the state vector [x] and the system control input $[u_t]$ cannot be directly observed.

It is assumed that the state vector [x] is indirectly estimated by the observation model shown in (6B) of FIG. 6. For the system control input $[u_t]$, only the statistical fluctuation range $[\sigma_{u,t}]$ is assumed as a parameter.

The measured current data [X] in the present embodiment is not a vector but a scalar, further various matrices are also scalars, and it can be regarded as [F]=[G]=[H]=[1]. Therefore, when letting $[x_t]$, $[y_t]$ and $[v_t]$ be the base line level of the actual current value at the time t, the current measured at the time t, and the observation noise at the time t, respectively, $[x_t]$ and $[y_t]$ are expressed as shown in (6 C) of FIG. 6. The $[x_t]$, $[u_t]$, $[v_t]$ are unobservable factors and $[y_t]$ is observable factor. Let f (Hz) be the measurement frequency of the ion current detector, the time data is 1/f (second) increments. Baseline estimation can be performed assuming that the influence of the system control input $[u_t]$ is practically very small.

Figure 7:
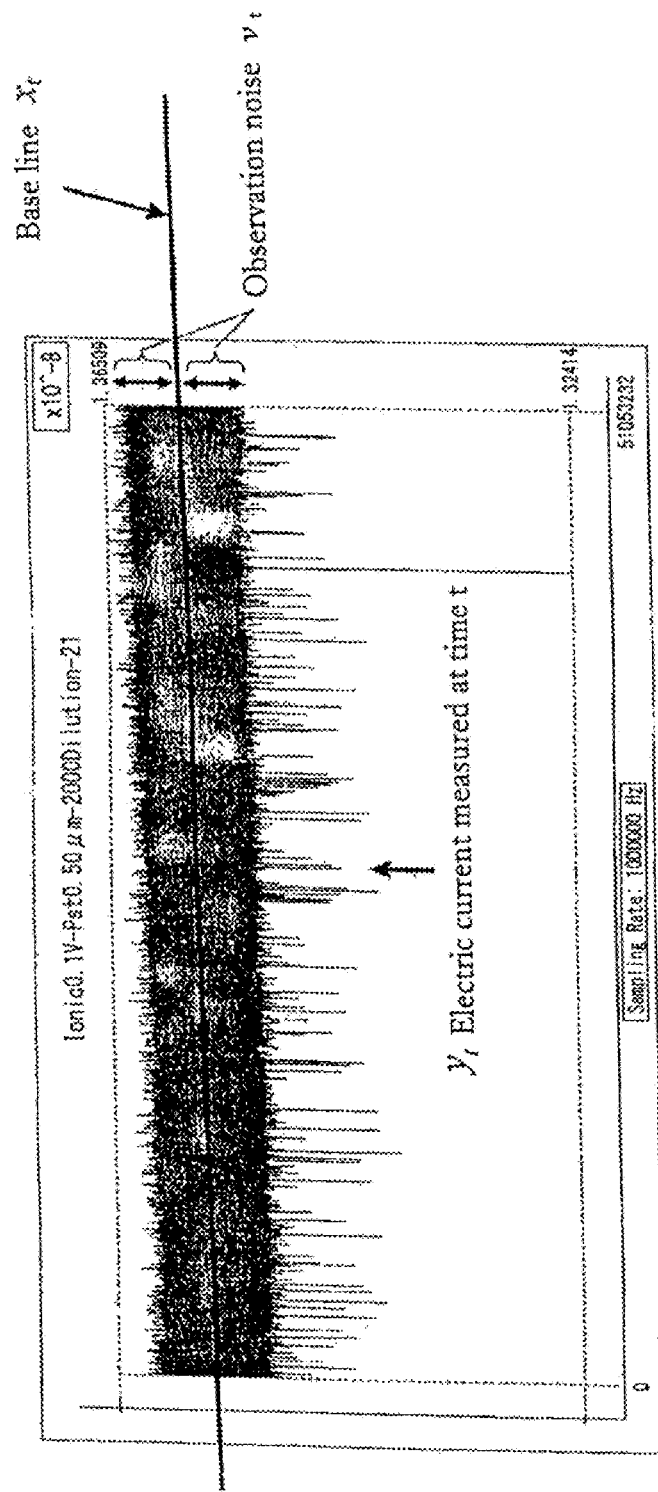
FIG. 7 is a diagram for explaining each factor of the Kalman filter with actual measured current data.

FIG. 7 is the diagram showing each of the above factors by the actual measurement current data. At the time of actual measurement by the ionic current detecting part, the particles are clogged in the through-hole 12, causing distortion of the base line. However, at the time of measurement, it interrupts at the point of occurrence of distortion and the measurement is performed after the cause of distortion is eliminated, so that only data including the base line without distortion is collected in the original data set.

The estimation due to the Kalman filter is performed by repetition of prediction and updating. The estimation of the base line is also executed by repetition of prediction and updating due to the Kalman filter.

Figure 8:
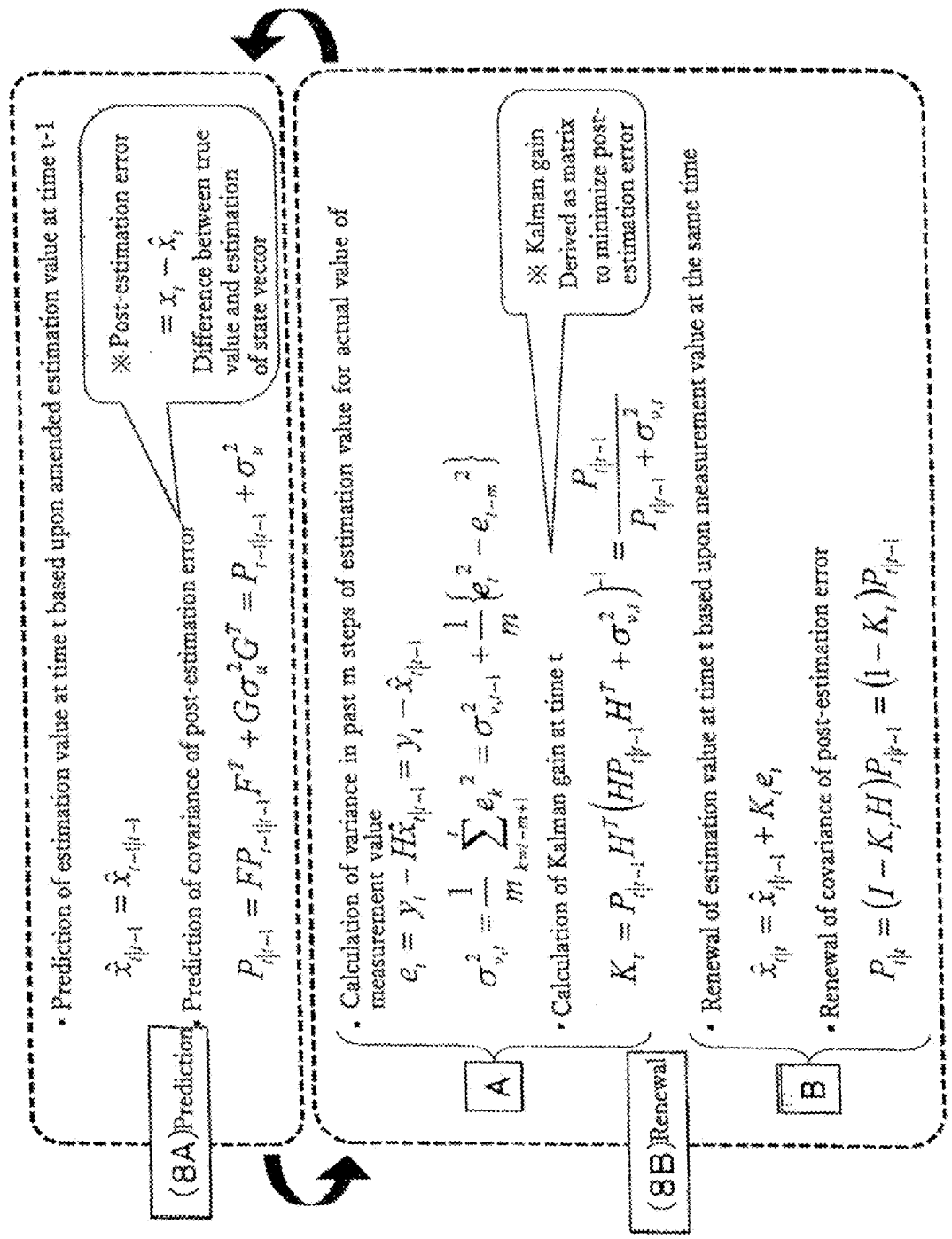
FIG. 8 is a diagram showing the details of the repetition of the prediction (8 A) and update (8 B) of the Kalman filter.

FIG. 8 is the diagram showing the details of the repetition of the prediction (8 A) and update (8 B) of the Kalman filter. In FIG. 8, the "hat" symbol added to the vector notation indicates the estimated value. The subscript "t|t−1" indicates that it is an estimate of the value at the time t based on the value at the time (t−1).

Figure 9:
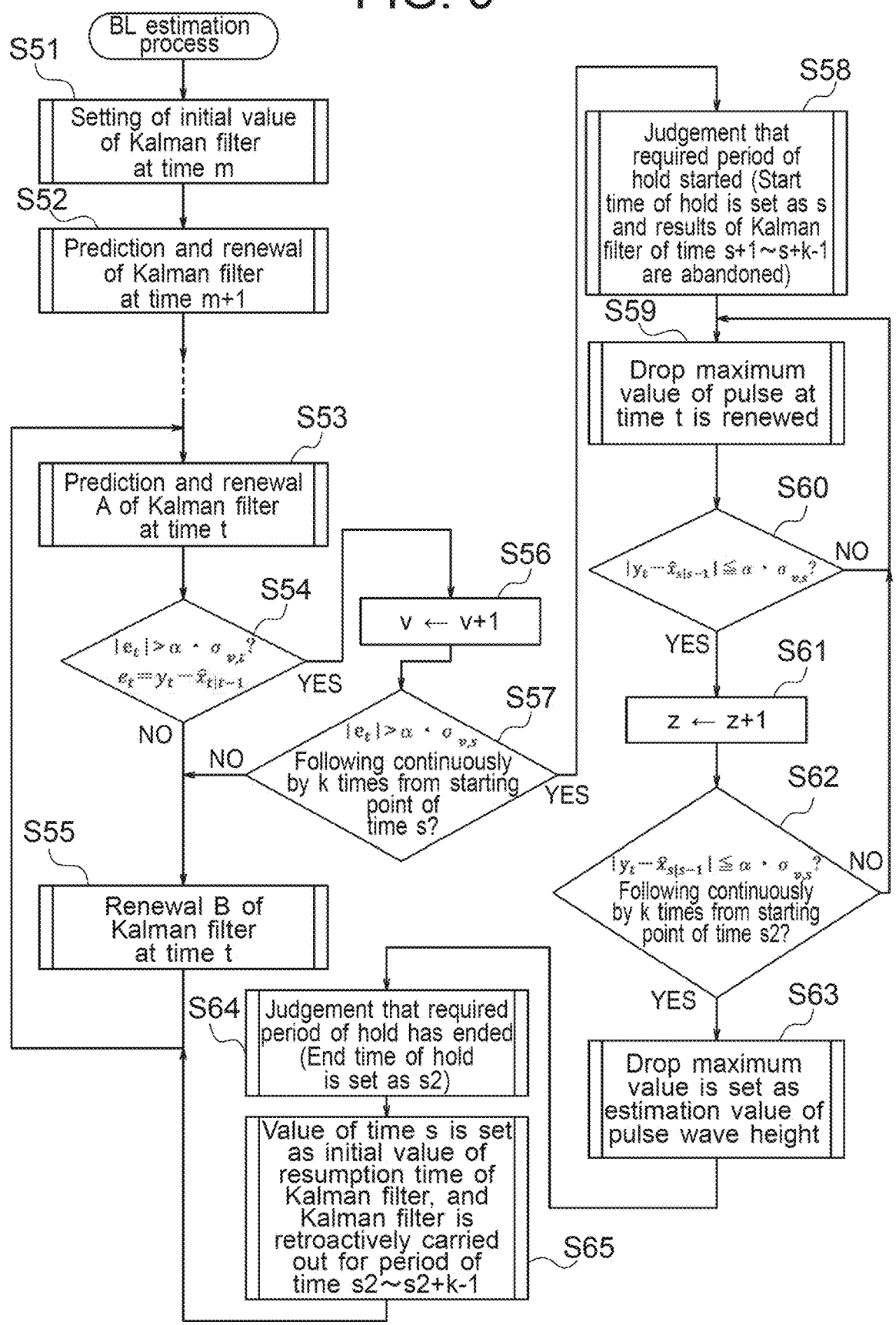
FIG. 9 shows a flowchart showing the BL estimation process based on the BL estimation process program.

FIG. 9 shows the BL estimation process based on the BL estimation process program. For the BL estimation process, the estimation of BL and the extraction of the pulse peak value based on the BL estimation are performed.

When executing the BL estimation process, the values of the start time m, the constants k, a of the adjustment factors necessary for the prediction and update process in the Kalman filter are adjusted (tuned) and decided to appropriate values according to the data attribute of the estimation target in advance. The value of a is the value for adjusting the dispersion of the estimated value of the base line. The value of k is the value related to the number of executions of update Ain the Kalman filter shown in FIG. 8 (see the steps S57 and S62 in FIG. 9). The start time m is the time data for the number of steps calculated with one measurement sampling as one step.

Figure 10:
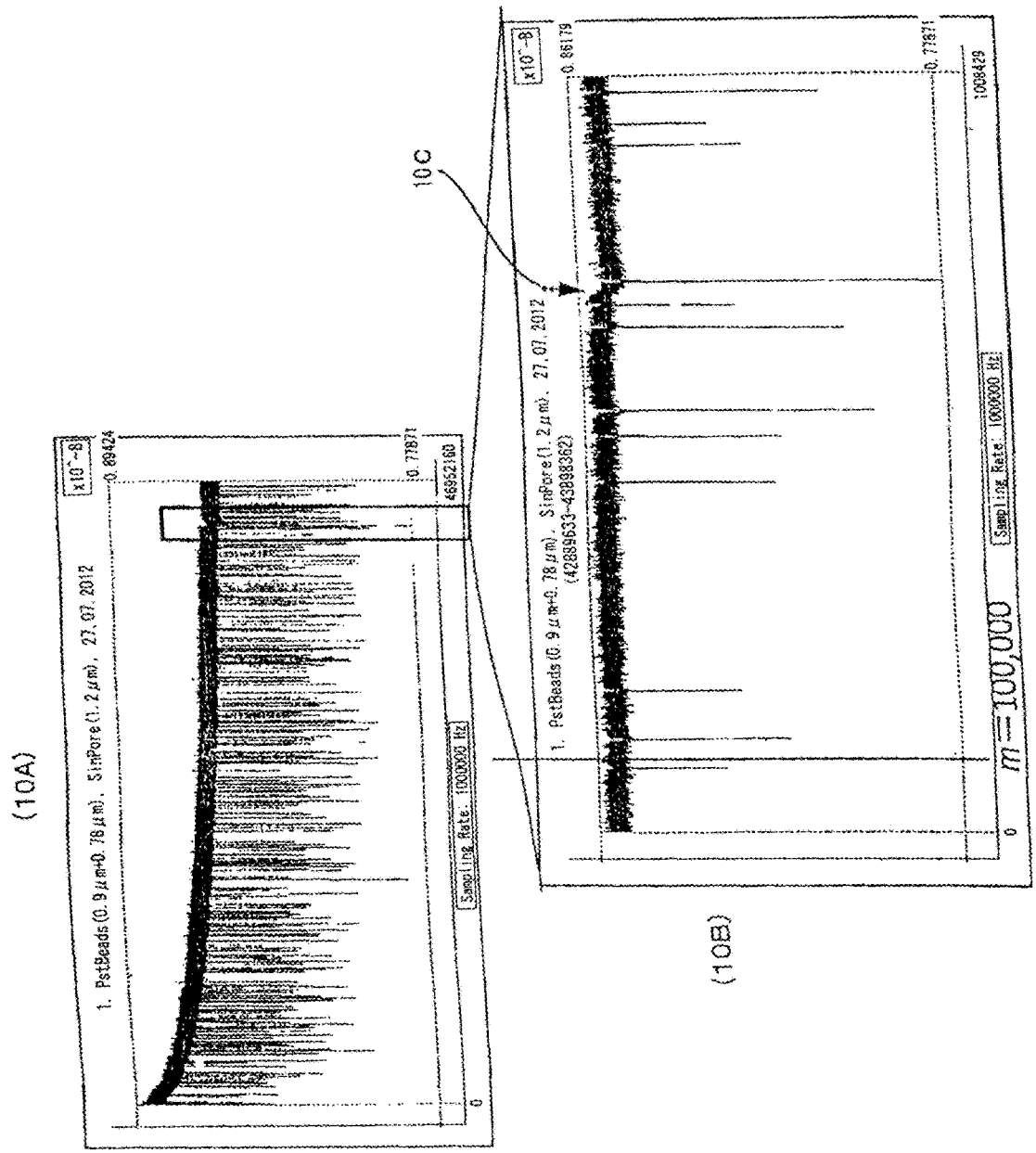
FIG. 10 is a waveform diagram of the bead model used for factor adjustment of the Kalman filter.

FIG. 10 shows the waveform diagram of the bead model used for the adjustment. FIG. 2 shows the solution state in the case (bead model) where the fine bead balls having the same size as bacteria or the like are mixed as particles. FIG. 10 (10A) is the waveform data acquired at the sampling frequency 900000 Hz by the ion current detection portion. The waveform of the bead model shown in (10A) shows the waveform that attenuates gradually. The violent depression has occurred in the right end portion of (10A), which is enlarged and shown in (10 B).

When the step portion (10 C) of the base line shown in (10B) is detected from the waveform of the bead model, the immediately preceding period becomes the initial value calculation period. For example, when m=100000, the 11 to 12 pulses having significance can be visually confirmed in the period excluding the initial value calculation period.

FIG. 12 is the table showing the number of pulses picked up from the waveform of the bead model according to the combination of m, k, and a of the adjustment factors.

The (12 A) of FIG. 12 shows the number of pulses according to the combination of k values (10, 30, 50, 70, 90) and a values (2, 3, 4, 6) when m=10000. FIG. 12B) shows the number of pulses according to the combination of k values (10, 30, 50, 70, 90) and a values (2, 3, 4, 6) when m=50000. (12C) shows the number of pulses due to the combination of k values (10, 30, 50, 70, 90) and a values (2, 3, 4, 6) when m=100000.

Comparing the three kinds of simulation results in FIG. 12, in the case of (12A) and (12B), the number of pulses to be measured is 12, and in the case of (12C) it is 11. Therefore, in the embodiment, the smallest (12 C) of the maximum value of the pulse number is adopted, and the tuning setting of m=100000, k=50, and a=6 is performed. These tuning setting data are stored and set in advance in the setting area of the RAM 23.

The BL estimation process of FIG. 9 is performed by the BL estimation due to the Kalman filter shown in FIG. 8 under the above tuning setting. First, in step S51, the initial value of the Kalman filter at time m is set in the work area of the RAM 23. At this time, the pulse waveform data stored in the data file storage portion 5 is read into the work area of the RAM 23. Next, the prediction and update (A and B of FIG. 8) of the Kalman filter at time (m+1) are executed (step S52). In the prediction and update, each operation of the Kalman filter shown in FIG. 8 is executed and stored in the RAM 23. After that, the prediction and update (A and B) are repeatedly performed at the predetermined unit time, and when the prediction and update A of the Kalman filter at time t are performed, it is judged whether or not the condition of the following equation 6 is satisfied (Steps S53 and S54). The unit time is the value determined by the sampling frequency of the original data, and is set in advance in the RAM 23.

$$|e_t| \alpha \cdot \sigma_{v,t} \; e_t = y_t - \hat{x}_{t|t-1}$$ [Equation 6]

When the condition of the equation 6 is not satisfied, the update B of the Kalman filter at the time t is executed, and the processes of the steps S53 to S55 are repeated for each data whose unit time has elapsed. When the above condition of Equation 6 is satisfied, the number value is cumulatively stored in the count area of the RAM 23 every time (steps S54 and S56). Next, on the basis of the count value, it is judged whether or not the condition of the equation 6 has been satisfied by k times consecutively starting from the time s (step S57). If it is not consecutive by k times, the process proceeds to step S55 and the update B is performed.

When the k times consecutive, the process proceeds to step S58, and it is judged that the hold necessary period for determining the BL has started. At this time, the hold start time of the hold necessary period is stored as s in the RAM 23, and the operation result of the Kalman filter between the time (s+1) and the time (s+k−1) is not stored but discarded.

By the start of the hold necessary period, the drop maximum value of the pulse at the time t is stored in the RAM 23 in a updatable manner (step S59). Next, similarly to step S54, it is judged whether or not the condition of the following equation (7) is satisfied during the hold necessary period (step S60).

$$|y_t - \hat{x}_{s|s-1}| \le \alpha \cdot \sigma_{v,s}$$ [Equation 7]

When the condition of the above formula 7 is not satisfied, the pulse drop maximum value is updated (steps S59, S60). When the condition of Equation 7 is satisfied, the number value is cumulatively stored in the count area of the RAM 23 at each time (steps S60, S61). Next, on the basis of the count value, it is judged whether or not the condition of the equation (7) has been satisfied by k times consecutively starting from the time s2 (step S62). If it is not k times consecutive, the process returns to step S59.

If k times consecutive, the process proceeds to step S63, and the maximum drop value of the pulse which is updated and stored at this time is stored in the RAM 23 as the estimation value of the pulse wave height value. The estimation value of the pulse wave height value is stored together with the data of the pulse start time and the pulse end time. When the estimation of the pulse wave height value is completed, it is determined that the hold necessary period is ended. By this termination, the hold end time of the hold necessary period is stored in the RAM 23 as s2 (step S64). Next, in step S65, the value of the time s is retroactively calculated for the period from the time s2 to the time (s+k−1) as the initial value at the restart of the operation process of the Kalman filter and the operation of the Kalman filter is executed. After step S65, it is judged whether or not the BL estimation process of all pulse waveform data has been performed (step S66), and the process is terminated at the completion of estimation of all pulse waveform data, and when there is remaining data, the process goes to step S53.

<About Feature Value Extraction>

Figure 13:
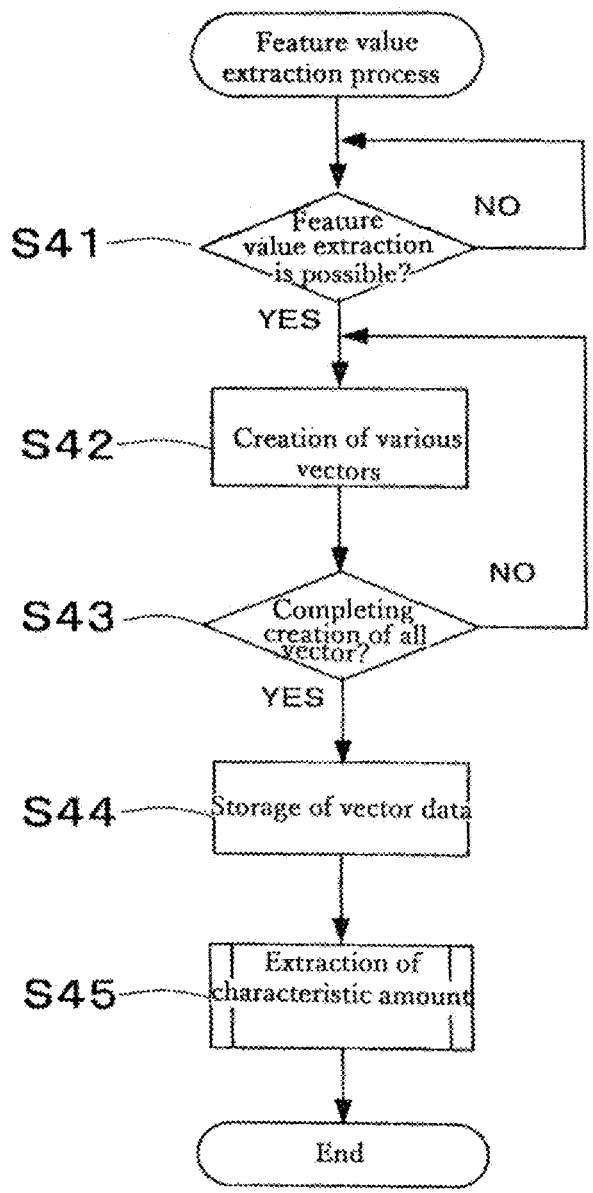
FIG. 13 is a flowchart showing the outline of contents of the execution process of the feature value extraction program.

FIG. 13 shows the outline of the executing process content of the feature value extraction program.

The feature value extraction process becomes executable on condition that the extraction data of the pulse wave height value (wave height |h|) is present by execution of the BL estimation process of FIG. 9 (step S41). When there is the extraction data of the pulse wave height value, the wave height vector acquisition program and the wave width vector acquisition program described above are executed and the data generation calculation of various vectors is executed (step S42). When all the data acquisition of the wave height vector and the wave width vector is completed, the vector data is stored (steps S43 and S44). Next, the extraction process of various feature values is executed (step S45). In acquiring the data of the wave height vector and the wave width vector, the interpolation process using the cubic spline interpolation method, the linear interpolation process and the truncation process are performed at any time.

Figure 41:
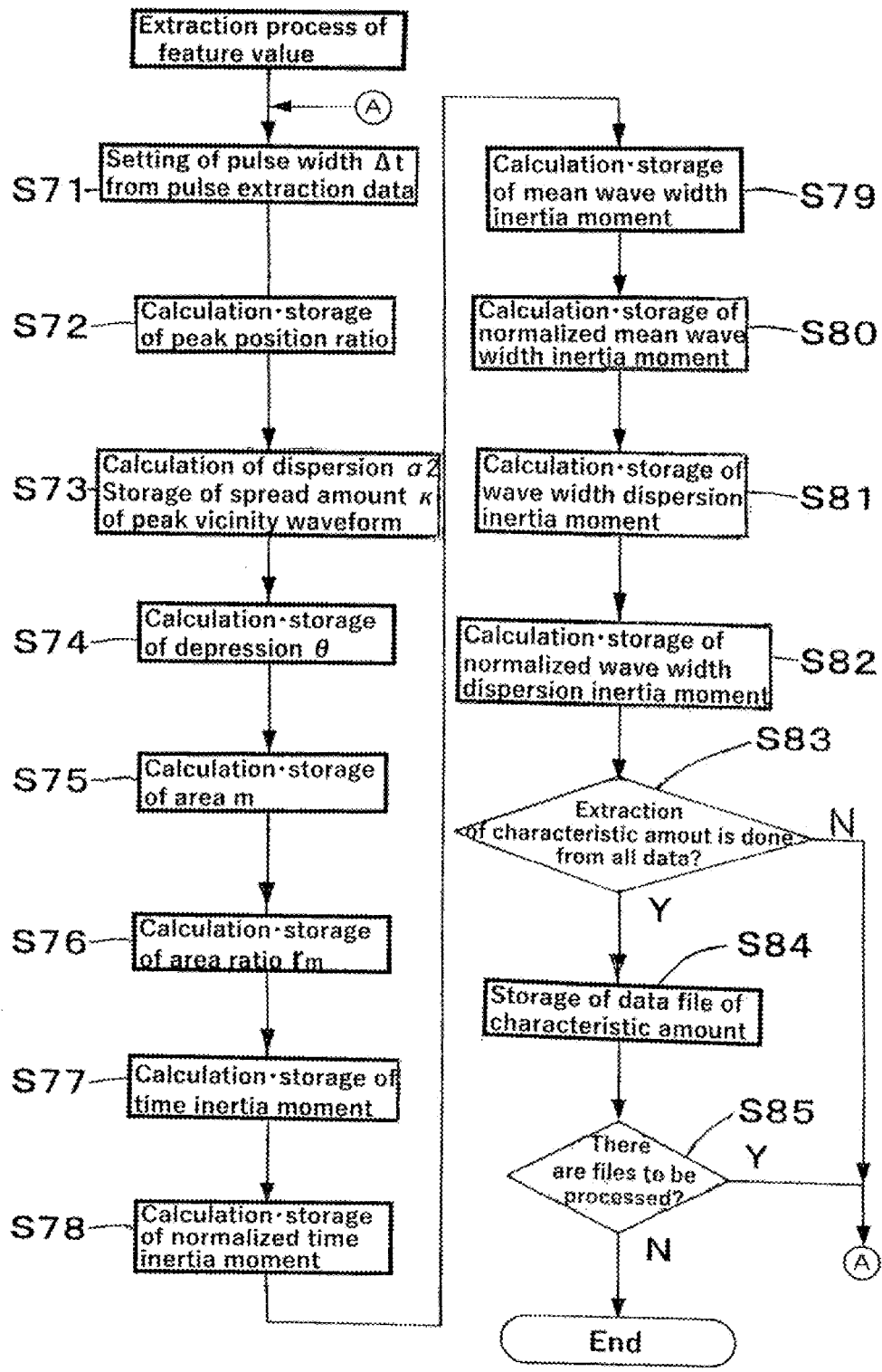
FIG. 41 is a flowchart showing the processing contents of feature value extraction.

FIG. 41 shows the contents of execution process of the feature value extraction process (step S45). The Steps S71 to S83 show the calculation of the first type and the second type of feature values defined in above (1) to (13), and the process of remembering and storing the calculated feature values, respectively.

The first type of feature values are calculated in steps S71 to S76. The wavelength (pulse width) Δt is sequentially calculated and stored with respect to the extracted data group of the pulse wave height value (step S71). The calculated feature value is stored in the memory area for storing the feature value of the RAM 4. The pulse width is obtained by calculating Δt (=$t_e$−$t_s$; $t_s$ is the start time of the pulse waveform and $t_e$ is the end time of the pulse waveform). The peak position ratio r is sequentially calculated and stored with respect to the extraction data group of the pulse wave height value (step S72). The peak position ratio r is calculated by r=($t_p$−$t_s$)/($t_e$−$t_s$) (the ratio of the pulse width Δt and the time ($t_p$−$t_s$) leading from the pulse start to the pulse peak pp.

The peak kurtosis K is sequentially calculated and stored with respect to the extraction data group of pulse wave height values (step S73). It is normalized so as that the wave height |h|=1, $t_s$=0 and $t_e$=1 hold, and there are collected the time set [T]=[[ti]|i=1, . . . , m] which is the time crossing the horizontal line of 30% in wave height from the pulse peak PP, and then the κ is obtained so that the dispersion of the data of the time set [T] is calculated as the pulse waveform spread.

The depression θ is obtained based on the time from pulse start to pulse peak and wave height data and the calculation of Equation 2 above (step S74). The area m is obtained from the wave height vector data, and is calculated and stored by obtaining the time division area hi according to the number of division (number of divisions set in advance: 10) and calculating the total sum thereof. The area ratio $r_m$ is calculated and stored by calculating the total waveform area and the partial sum of time division area hi in each division leading from the pulse start to the pulse peak and by calculating the area ratio of the partial sum to the total waveform area (Step S76).

The second type feature values are calculated in steps S77 to S82. The time inertia moment is obtained from the data of the wave height vector, and are calculated and stored based on the time division area hi obtained according to the number of divisions and the calculation of Equation 5 above (step S77). The normalized time inertia moment of (9) is stored as the normalization data (step S78) by the process normalized in the wave height direction (the inner product of the wave height vector and the normalized vector) so that the wave height becomes "1" of the reference value with respect to the time inertia moment obtained in step S77. The wave width mean value inertia moment is calculated from the data of the wave width vector (the difference vector of the mean value) obtained in steps S42 to S44 by using the time value calculated for each division unit (the number of divisions set in advance: 10) before and after the pulse peak and the calculation of Equation (6) and is stored (step S79). The wave width mean value inertia moment (11) is stored as the normalization data (step S80) normalized in the wavelength direction (the inner product of the difference vector of the mean value and the normalized vector) so that the wavelength becomes the reference value "1" for the wave width mean value inertia moment obtained in step S79. The wave width dispersion inertia moment is calculated from the data of the wave width vector (dispersion vector) based on the dispersion of the time value calculated for each division unit and the calculation of the above equation 6 and stored (step S 81). The normalized wave width dispersion inertia moment of (13) is stored as the normalization data (step S82) normalized in the wavelength direction (the inner product of the dispersion vector and the normalized vector) so that the wavelength becomes the reference value "1" with respect to the wave width dispersion inertia moment obtained in step S 81.

Upon completing the extraction of the feature value from all the data, the file of each data is stored and it is judged whether or not there is another data group (steps S83, S84). If there is the data group of another file, the above process (steps S71 to S82) can be repeatedly executed. When there is no more data to be processed, the extraction process of the feature value ends (step S 85). In the above extraction process, all of the first type and the second type of feature values are obtained, but it is also possible to designate a desired feature value by designation input of the input means 6 and it is possible to extract only the feature value due to this designation.

Figure 14:
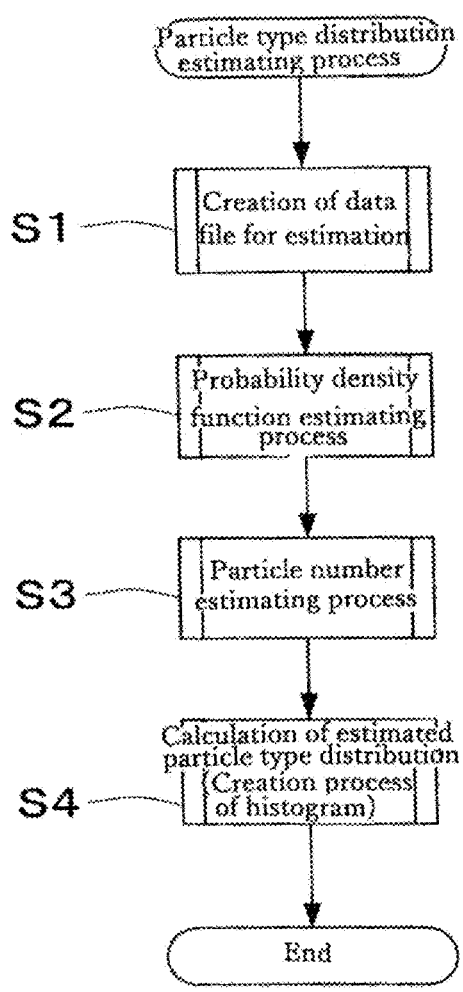
FIG. 14 is a flowchart showing the particle type distribution estimating process.

FIG. 14 shows the particle type estimation process executed based on the particle type distribution estimation program.

<About Estimation of Probability Density Function>

Since the pulse waveform to be measured is not necessarily constant even for the same type of particles, the probability density function of the pulse waveform of particle type is preliminarily estimated from the test data as preparation for the particle type distribution estimation. The appearance probability of each pulse can be expressed by the probability density function derived through the estimation of the probability density function.

The (15 B) of FIG. 15 is the image diagram of the probability density function for the pulse waveform obtained by using the pulse width and the pulse wave height as the feature value of the pulse waveform in the particle types of *Escherichia coli* and *Bacillus subtilis*, and the appearance probability of the pulse is expressed by shading in the figure. The (15 A) of FIG. 15 shows a part of the first type of feature value relating to one waveform data.

Since the true density function of the pulse width Δt and the pulse wave height h is unknown, it is necessary to estimate the nonparametric probability density function. In the present embodiment, the Kernel density estimation using a Gaussian function as the Kernel function is used.

Kernel density estimation is a method of assuming the probability density distribution given by Kernel function to the measurement data and regarding the distribution obtained by superimposing these distributions as the probability density function. When using a Gaussian function as the Kernel function, it is possible to assume a normal distribution for each data and to regard the distribution obtained by superimposing them as the probability density function.

Figure 16:
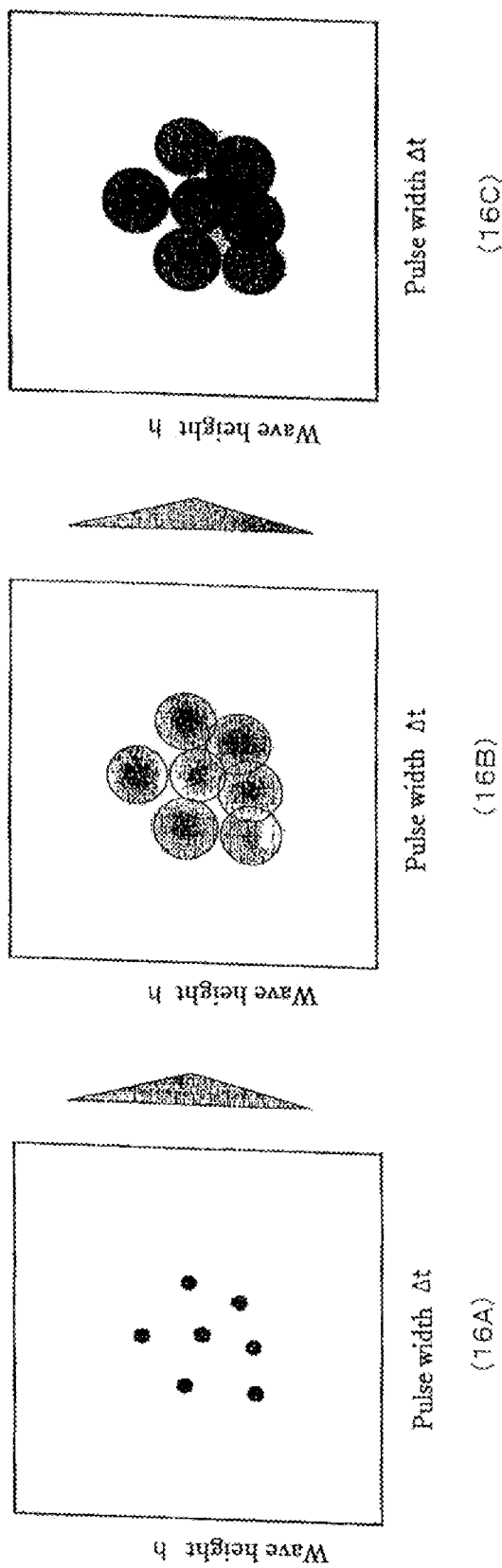
FIG. 16 is an image diagram of a superposition of probability density distributions obtained from each particle type of *Escherichia coli* and *Bacillus subtilis*.

FIG. 16 is the image diagram of a superposition of probability density distributions obtained from each particle type of *Escherichia coli* and *Bacillus subtilis*. FIG. 16C shows the state in which the probability density distribution (16 B) obtained for each particle is superimposed from the feature value data (16 A) of the pulse width Δt and the pulse wave height h.

The probability density function [p(x)] for the input data [x] is expressed by the following equation 8 using the number of teacher data [NT], the teacher data [μi], and the variance covariance matrix [Σ].

Probability distribution function for input data $x = \begin{bmatrix} \Delta t \\ h \end{bmatrix}$ [Equation 8]

$$p(x) = \frac{1}{N}\sum_{i=1}^{N} \frac{1}{2\pi\sqrt{|\Sigma|}} \exp\left(-\frac{(x-\mu_i)^T \Sigma^{-1}(x-\mu_i)}{2}\right)$$

Furthermore, the probability density function [p(x)] can be expressed by the product of the Gaussian functions of each dimension as shown in the following Equation 9.

For simplicity of calculation, the covariance term [Equation 9]
of the variance–covariance matrix Σ is set to 0

$$\Sigma = \begin{bmatrix} \sigma_{\Delta t}^2 & 0 \\ 0 & \sigma_h^2 \end{bmatrix} \quad |\Sigma| = \sigma_{\Delta t}^2 \sigma_h^2, \quad \Sigma^{-1} = \begin{bmatrix} 1/\sigma_{\Delta t}^2 & 0 \\ 0 & 1/\sigma_h^2 \end{bmatrix}$$

$$p(x) = \frac{1}{N}\sum_{i=1}^{N} \left\{ \frac{1}{\sqrt{2\pi}\sigma_{\Delta t}} \exp\left(-\frac{(\Delta t - \mu_{\Delta t}^i)^2}{2\sigma_{\Delta t}^2}\right) \right\} \left\{ \frac{1}{\sqrt{2\pi}\sigma_h} \exp\left(-\frac{(h - \mu_h^i)^2}{2\sigma_h^2}\right) \right\}$$

As can be seen from Equation 9, it is equivalent to assuming that each pulse attribute is an independent random probability variable that follows the normal distribution, which can be expanded to three or more dimensions as well. Therefore, in the present embodiment, it is possible to analyze the number of two or more types of particle types.

The probability density function module program has a function of computing and obtaining the probability density function for two types of feature values. That is, in the case of using the estimation target data due to two feature values [(β, γ)], the probability density function [p(β, γ)] in the Kernel density estimation using the Gaussian function as the Kernel function is expressed by the following equation 10.

The covariance term of the variance–covariance matrix $\Sigma$ is set to 0 and when $\Sigma = \begin{bmatrix} \sigma_\beta^2 & 0 \\ 0 & \sigma_\gamma^2 \end{bmatrix}$ and teacher data $\mu_\beta^i, \mu_\gamma^i$ $$p(\beta, \gamma) = \frac{1}{N} \sum_{i=1}^{N} \left\{ \frac{1}{\sqrt{2\pi\sigma_\beta^2}} \exp\left(-\frac{(\beta - \mu_\beta^i)^2}{2\sigma_\beta^2}\right) \right\} \left\{ \frac{1}{\sqrt{2\pi\sigma_\gamma^2}} \exp\left(-\frac{(\gamma - \mu_\gamma^i)^2}{2\sigma_\gamma^2}\right) \right\}$$

[Equation 10]

The probability density function estimation process executed by the probability density function module program based on the equation 10 performs the estimation process of the probability density function in two feature values, as described in detail later with reference to FIG. 20.

Figure 17:
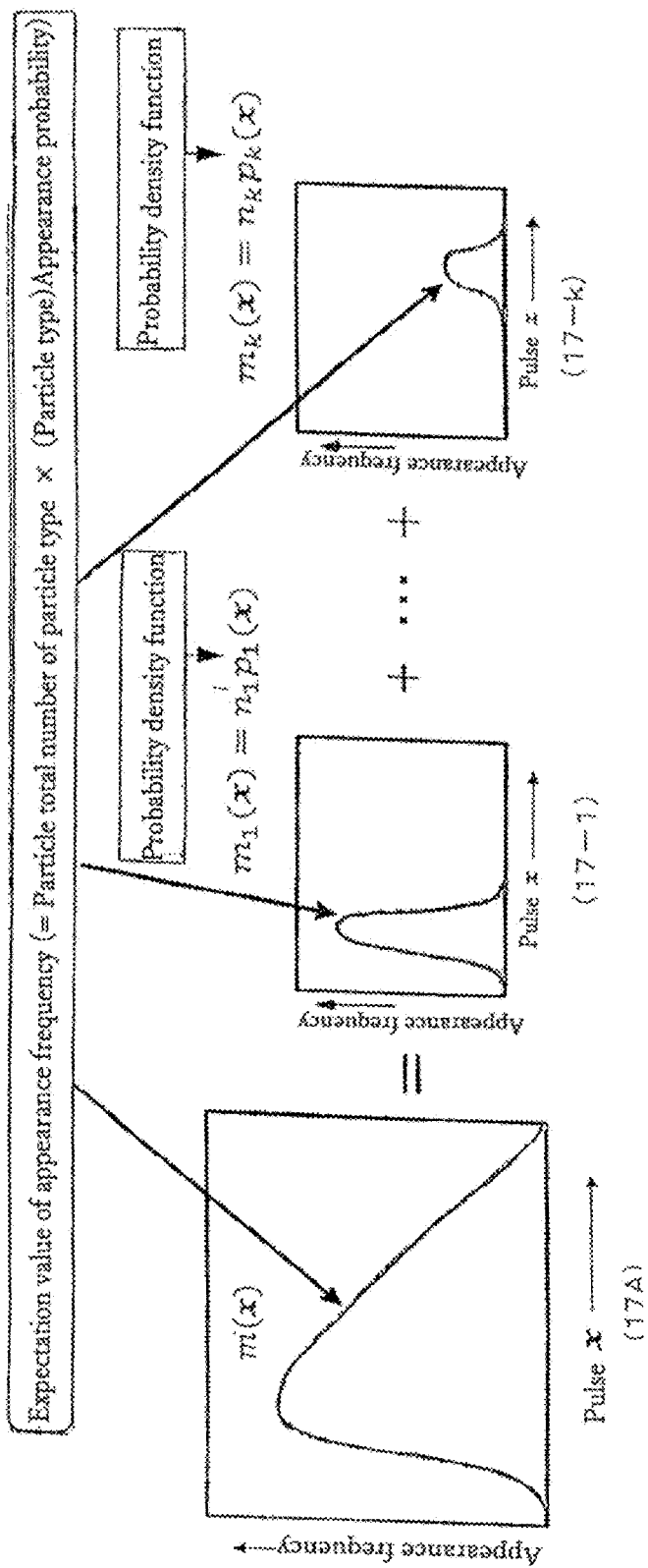
FIG. 17 is an image diagram showing the relationship between the total number of particles of k particle types, the appearance probability of particle type, and the expected value of appearance frequency of the entire data.

FIG. 17 is the image diagram showing the relationship between the total number of particles of k particle types, the appearance probability of particle type, and the expected value of appearance frequency of the entire data. FIG. 17 (A) shows the appearance frequency of the entire data. FIGS. 17-1) to (17-$k$) show the appearance frequency of particle types. The expected value of the appearance frequency at which the pulse [x] is measured becomes the sum of the expected value of the appearance frequency at which the pulse [x] is measured according to the particle type probability density function. As shown in FIG. 17, it can be expressed by the following equation 11 as the sum of expectation values of particle types from the total number of particles [$n_i$] of particle type and the particle type appearance probability [$p_i(x)$].

$$m(x) = \sum_{i=1}^{k} m_i(x) = \sum_{i=1}^{k} n_i p_i(x)$$

[Equation 11]

In the present embodiment, the probability density function data (see Expression 9) obtained by estimating the probability density function of the particle type obtained in advance is stored in the RAM 23 as the analysis reference data. The particle type number analysis is performed by determining the appearance frequency of the entire data to be analyzed based on the equation 11 through identifying the number of particle types to be matched from each analysis data. The number analysis is performed by estimating histograms of different particle types (appearance frequency (number of particles) for particle type).

In the particle type estimation process shown in FIG. 14, the data file creation process (step S1) for creating the data file due to the feature value by editing data, the particle number estimation process (step S2), and the calculation process of estimated particle type distribution (histogram creation process) (step S3) are performed. In the particle number estimation process, the estimation methods based on the maximum likelihood method, the Lagrangian multiplier method and the Hasselblad iteration method can be used.

<About Maximum Likelihood Estimation (The Method of Point Estimation of Population of Probability Distribution that it Follows from Data Given in Statistics)>

It is assumed that a data set $[D]=[x_1, x_2, x_3, \ldots X_N]$ has been obtained as an actual pulse estimation result. The likelihood at which the estimated j-th pulse height data appears is expressed by the following equation 12.

$$p(x_j) = \frac{m(x_j)}{N} = \frac{1}{N} \sum_{i=1}^{k} m_i(x_j) = \frac{1}{N} \sum_{i=1}^{k} n_i p_i(x_j)$$

[Equation 12]

Then, the likelihood of appearance of the data set D is expressed by the following equation 13.

$$\prod_{x_j \in D} p(x_j) = \frac{1}{N^N} \prod_{x_j \in D} \sum_{i=1}^{k} n_i p_i(x_j)$$

[Equation 13]

The particle type distribution that maximizes the likelihood in Equation 13 is the particle type distribution with the most likelihood value set $[n]=[n_1, \ldots, n_k]^T$.

<About Lagrangian Undetermined Multiplier Method (It is an Analytical Method to Optimize Under Constraint Conditions, Prepare the Undetermined Multipliers for Each Constraint Condition and Make New Functions of Linear Combinations Using These Multipliers as Coefficients (Unknown Multipliers are New Variables), and it is a Method to Solve the Constraint Problem as the Normal Extreme Problem>

Maximizing the likelihood of occurrence of data set D is equivalent to maximizing the logarithmic likelihood that data set [D] appears. The following equation 14 shows the process of deriving the logarithmic likelihood to check the suitability of the Lagrange undetermined multiplier method.

$$\prod_{x_j \in D} p(x_j) = \frac{1}{N^N} \prod_{x_j \in D} \sum_{i=1}^{k} n_i p_i(x_j) \rightarrow \max$$

$$\log \prod_{x_j \in D} p(x_j) = \log\left(\frac{1}{N^N} \prod_{x_j \in D} \sum_{i=1}^{k} n_i p_i(x_j)\right) \rightarrow \max$$

$$\sum_{x_j \in D} \log p(x_j) \propto \log L(n; D) \rightarrow \sum_{x_j \in D} \log \sum_{i=1}^{k} n_i p_i(x_j) \xrightarrow[n]{} \max$$

[Equation 14]

In Equation 14, the coefficient 1/NN in the middle is omitted in the final expression.

Here, the value set n=[n1, . . . , Nk]T of the particle diameter number distribution has the constraint "the total is N" (see the following equation 15).

$$N = \sum_{i=1}^{k} n_i$$

[Equation 15]

Therefore, since the proposition of obtaining the most likelihood particle type distribution becomes a problem of constrained logarithmic likelihood maximization, it is possible to perform optimization by the Lagrangian undetermined multiplier method. The constrained logarithmic likelihood maximization equation that optimizes by the Lagrange undetermined multiplier method can be expressed by the following equation 16.

$$\sum_{x_j \in D} \log \sum_{i=1}^{k} n_i p_i(x_j) - \lambda \left( \sum_{i=1}^{k} n_i - N \right) \underset{n,\lambda}{\to}$$ [Equation 16]

max(Lagrange undetermined multiplier method)

From the constrained logarithmic likelihood maximization equation shown in Equation 16, [k] simultaneous equations shown in the following Equation 17 can be derived through the mathematical derivation process shown in FIG. 18.

$$\sum_{x_j \in D} \frac{p_i(x_j)}{\sum_{i=1}^{k} n_i p_i(x_j)} = 1$$ [Equation 17]

To solve numerically the simultaneous equations shown in Equation 17, it can be performed using the iterative method proposed by Hasselblad. According to the Hasselblad iteration method, the iterative calculation of the following Equation 18 may be performed. The details of this iterative method are described in the proposal paper (Hasselblad V., 1966, Estimation of parameters for a mixture of normal distributions. Technomerics, 8, pp. 431-444).

$$n_i^{(t+1)} = n_i^{(t)} \sum_{x_j \in D} \frac{p_i(x_j)}{\sum_{i=1}^{k} n_i^{(t)} p_i(x_j)}$$ [Equation 18]

For the iterative calculation of Equation 18, it is performed using the software of EM algorithm available on the market. As clear from the origin of naming, the EM algorithm is the method of calculating the probability distribution parameter by maximizing the likelihood function, that is, the algorithm which can maximize the expectation of the probability distribution being the likelihood function. According to the EM algorithm, the initial value of the desired parameter is set, the likelihood (expected value) is calculated from the initial value, and in many cases, using the condition that the partial differential of the likelihood function becomes zero, the maximum likelihood parameters can be calculated by iterative calculation. In the Hasselblad iterative arithmetic operation performed by using the EM algorithm, the initial value of the parameter to be obtained is set, the likelihood (expected value) is calculated from the initial value, and furthermore, under the condition that the partial differential of the likelihood function becomes zero, the maximum likelihood parameter is calculated by carrying out the iterative calculation.

<Particle Type Estimation Process>

In order to execute the particle type estimation process shown in FIG. 14, there will be described below the processes such as the data file creation process (step S1), the probability density function estimation process (step S2), the particle number estimation process (step S3) and the calculation process of the estimated particle type distribution.

Figure 19:
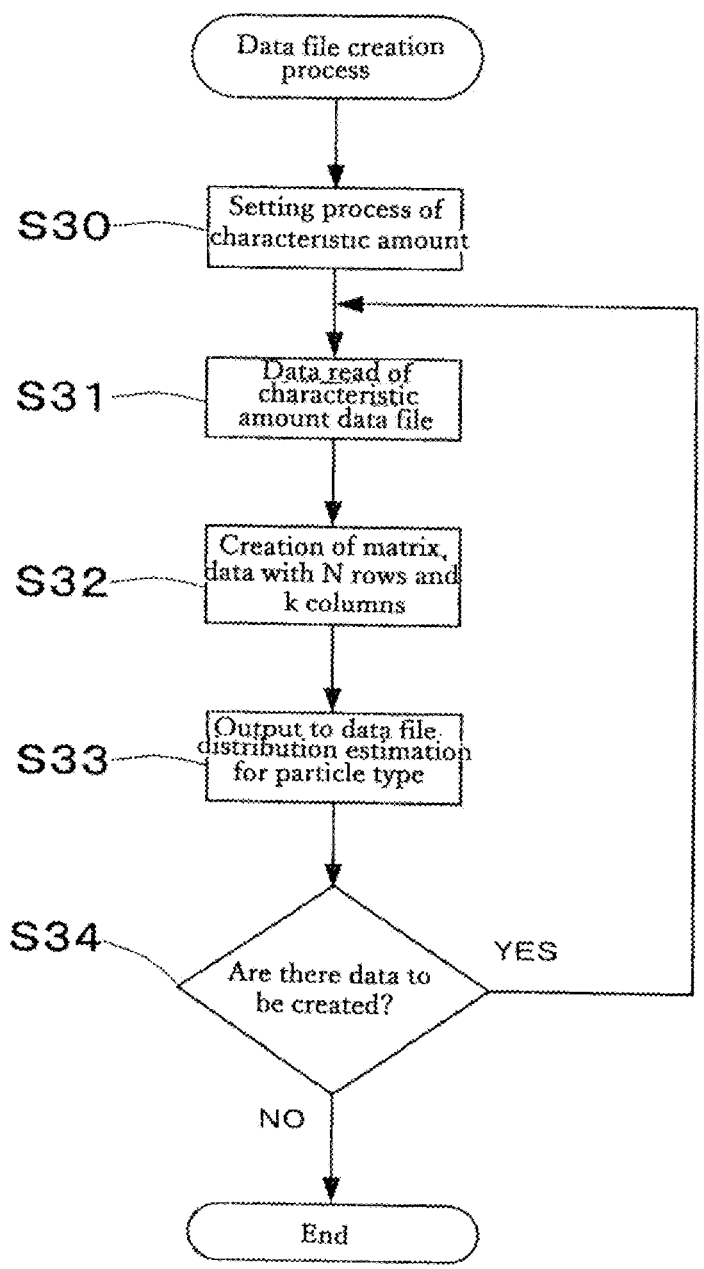
FIG. 19 is a flowchart showing the data file creation process.

FIG. 19 shows the data file creation process (step S1) executed by the data file creation program.

By using the input means 6 of the PC 1, it is possible to perform the designation operations of k (2 in the embodiment) feature values for creating the data file. The combination input of the designated feature values is set in the RAM 23 (step S30). The data of the feature value data file for each feature value setting is read into the work area of the RAM 23 (step S31). The feature value data file is estimated and extracted by the BL estimation process in FIG. 9 and the feature value estimation process in FIG. 13 and stored in the file.

The matrix data of N rows and k columns is created by designating k feature values used for the number estimation (step S32). The created matrix data is outputted to the particle type distribution estimation data file and stored for each designated feature value (step S33). Upon completion of creation of all the data files for the designated feature value, the process ends (step S34).

Figure 20:
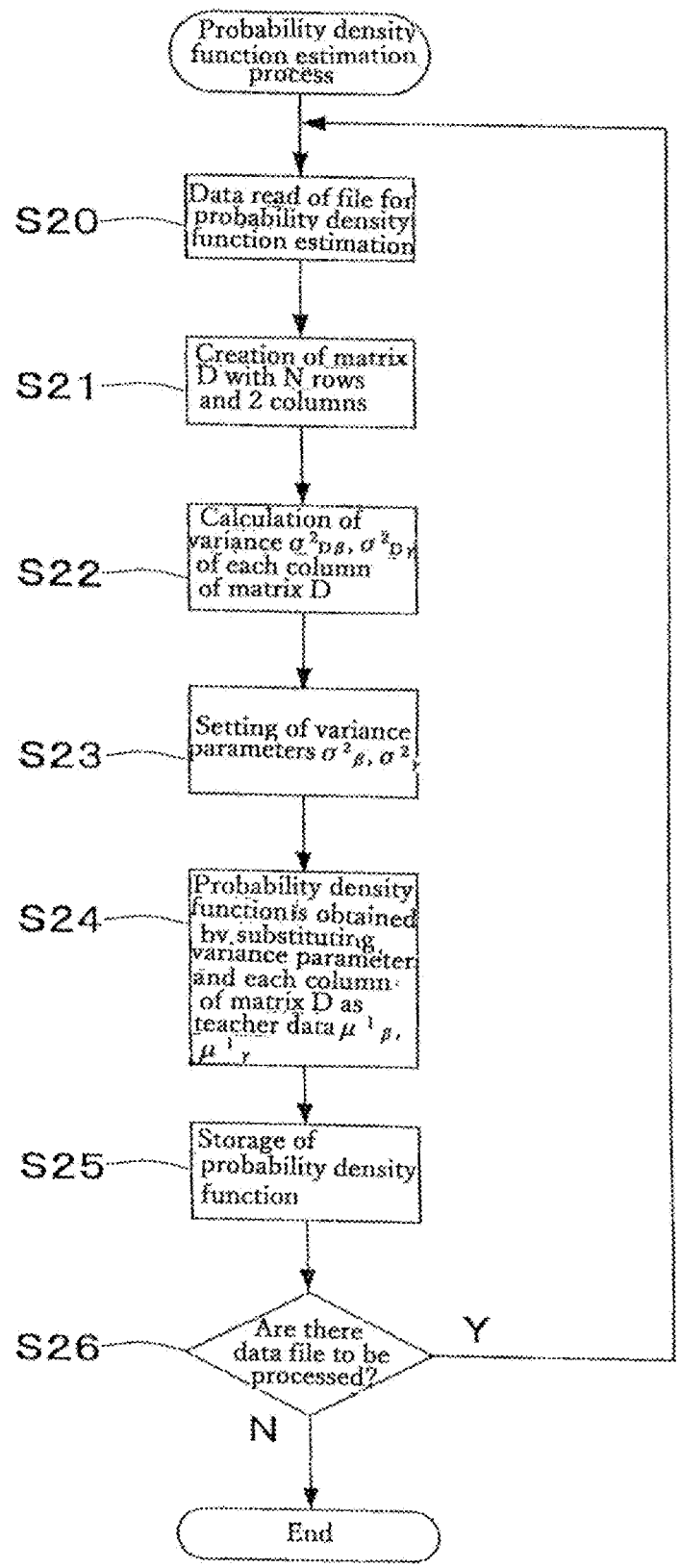
FIG. 20 is a flowchart showing the estimation process of the probability density function.

FIG. 20 shows the estimation process of the probability density function (step S2) executed by the probability density function module program. In the probability density function estimation process, the estimation process of the probability density function in two feature values is performed based on the Equation 5.

Data of the data file of the probability density function estimation target created in the data file creation process (step S1) is read to form the matrix [D] of N rows and 2 columns (steps S20 and S21).

$$\sigma_{D_\beta}^2, \sigma_{D_\gamma}^2$$ [Equation 19]

The dispersion shown in the following equation 19 for each column of the matrix [D] is calculated (step S22). Next, the dispersion parameter shown in the following Equation 20 is set using the standard deviation coefficient c as shown in the following Equation 21 (Step S23).

$$\sigma_\beta^2, \sigma_\gamma^2$$ [Equation 20]

$$\sigma_\beta^2 = c^2 \sigma_{D_\beta}^2 \text{ and } \sigma_\gamma^2 = c^2 \sigma_{D_\gamma}^2$$ [Equation 21]

The probability density function is obtained by substituting each line of the dispersion parameter and matrix [D] as teacher data shown in the following Equation 22 and stored in the predetermined area of the RAM 23 (Steps S24 and S25). The process in steps S20 to S25 is performed until the probability density function is derived from all the process target data (step S26).

$$\mu_\beta^i, \mu_\gamma^i$$ [Equation 22]

Figure 21:
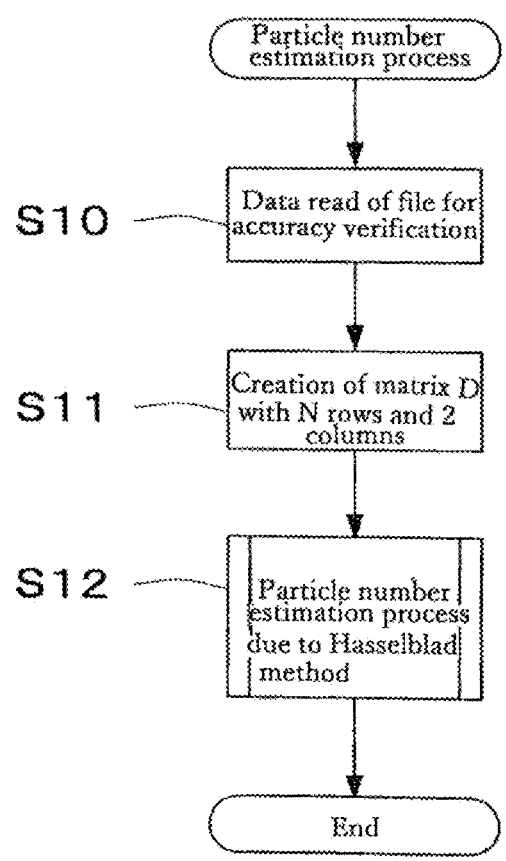
FIG. 21 is a flowchart showing the particle number estimation process.

FIG. 21 shows the particle number estimation process (step S3).

First, similarly to the above-described steps S20 and S21, the data of the data file of the particle number estimation target created in the data file creation process is read, and the matrix [D] of N rows and 2 columns is created (step S10, S11). For the matrix [D] data, the estimation process by the Hasselblad iteration method is executed (step S12).

Figure 22:
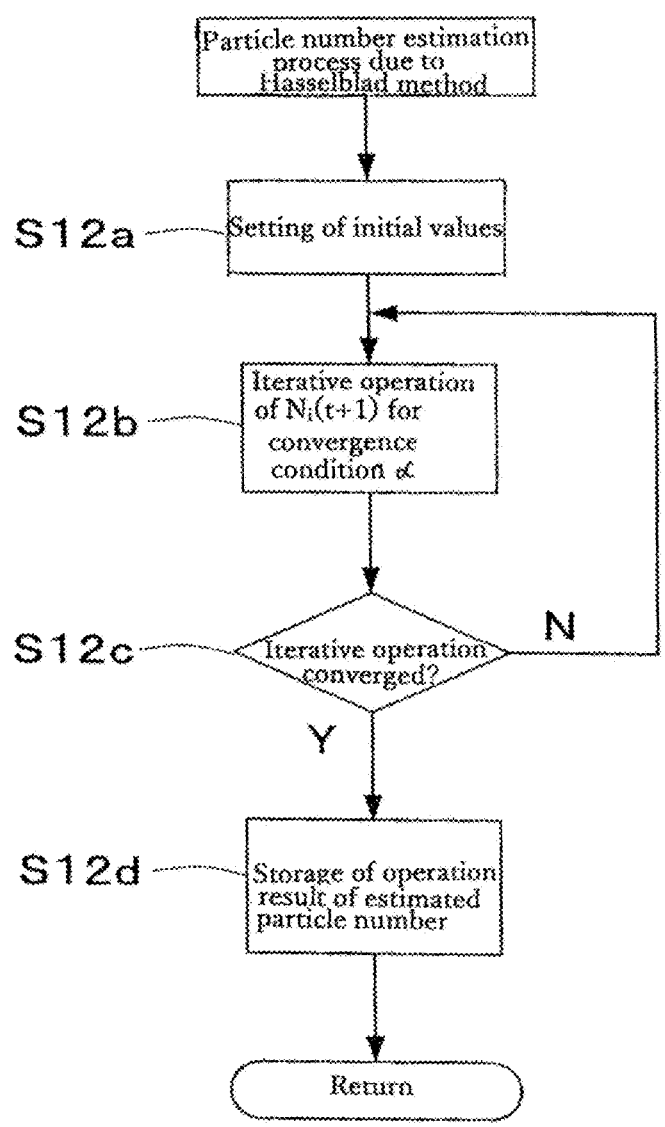
FIG. 22 is a flowchart showing the particle number estimation process by Hasselblad iteration method.

FIG. 22 shows the particle number estimation process due to the Hasselblad iteration method executed by the EM algorithm. FIG. 23 shows the process procedure by the EM algorithm.

First, after setting the initial value (process 19A), the number calculation based on the probability density function is sequentially executed (process 19B) (steps S12a and S12*b*). The iteration of the number calculation is executed until the convergence condition shown in (19C) is satisfied (step S12 *c*). The execution result (the estimated number data for each particle type) of the EM algorithm is stored in the predetermined area of the RAM 23 (step S12*d*).

In step 4, the estimated number data for each particle type obtained by the particle number estimation process is edited into the particle type number distribution data, and according to display designation, the histogram display output to the display means 7 becomes possible. Although not shown in FIG. 14, in the present embodiment, when designation of dispersion diagram output is received, it is possible to display and output the dispersion diagram of particle types due to the feature value data.

FIG. 24 shows an example of the results analyzed by the particle type number analyzing device according to the present embodiment. The (24A) and (25B) are the microscope enlarged photographs of *E. coli* and *B. subtilis* which are particle types to be analyzed. The (24C) and (25D) show the histogram and the dispersion diagram of the estimated number data for each particle type obtained by executing the particle number estimation process focusing on the pulse wave height and the pulse kurtosis as the feature value.

<About Verification 1 of Analytical Accuracy of Particle Type Number due to Feature Value>

The present inventors performed the verification 1 of the analysis performance of the particle type number under the following evaluation conditions using the measured current data of *Escherichia coli* and *Bacillus subtilis* in the above example.

The evaluation conditions of verification 1 are as follows.

(1) It is evaluated with the 1000 kHz experimental measurement data of *Escherichia coli* and *Bacillus subtilis*.

(2) As the feature values, four first type feature values of wavelength $\Delta t$, wave height h, peak position ratio r, and peak kurtosis k are calculated and used.

(3) The number estimation process on combinations of each feature value is performed.

(4) The actual measurement data of *Escherichia coli* and *Bacillus subtilis* are estimated and evaluated at random dividing for learning and testing. This estimation and evaluation is repeated 10 times, and the mean accuracy and standard deviation of them are calculated. In this case, the cross validation is used to evaluate the accuracy close to actual.

(5) A part of measured data of verification particles (*Escherichia coli* and *Bacillus subtilis*) are individually number-analyzed, the rest are randomly mixed with the predetermined mixture ratio $\delta$ for verification, and the number analysis results are compared. The data mixing program for the mixing random data is stored in the ROM 3, the random mixing of the data is executed using the PC1, and the number estimation for the randomly mixed data is performed. That is, in the matrix data of step S32 of FIG. 19, the random permutation matrix data of N rows and k columns created by the data mixing program is used. For the mixing ratio $\delta$, seven types of mixing ratios of *Escherichia coli* of 10, 20, 30, 35, 40, 45 and 50% are used. The values of parameters (adjustment factors) m, k and a for BL estimation are set to 100000, 400 and 6, respectively, and the standard deviation coefficient c for estimation of the probability density function is set to 0.1. The convergence condition a for estimating the number of particle types is set to 0.1. As the value of the adjustment factor used for the evaluation, the values obtained by performing more strict adjustment in the same manner as in the simulation example shown in FIG. 12 are used.

The (25A) and (25B) of FIG. 25 show the estimation result data of the verification example using the pulse wavelength and the wave height as the feature values and the verification example using the pulse wavelength and the peak position ratio as the feature values, respectively.

The number of all pulses obtained by this verification was 146 in *E. coli* and 405 in *B. subtilis*.

The (26A) and (26B) of FIG. 26 show the estimation result data of the verification example using the spread of the peak vicinity waveform and the pulse wavelength as the feature values and the verification example using the spread of the peak vicinity waveform and the wave height as the feature values.

The (26A) and (26B) of FIG. 26 show the estimation result data of the verification example using the spread of the peak vicinity waveform and the pulse wavelength as the feature values and the verification example using the spread of the peak vicinity waveform and the wave height as the feature values.

Evaluation of the particle type number can be performed by "weighted mean relative error" represented by the equation shown in (27B) of FIG. 27. "Weighted mean relative error" is the value obtained by multiplying the relative error of each particle diameter by the true number proportion of its particle diameter and adding it for the whole particle diameter.

The (27A) in FIG. 27 shows the number estimation result when the kurtosis and the pulse wave height are used as the feature value.

The (28A) and (28B) of FIG. 28 show the number estimation result for each mixing ratio 6 of the example using the pulse wavelength and the pulse wave height as the feature values and the number estimation result for each mixing ratio $\delta$ of the example using the pulse wavelength and the peak position ratio as the feature values, respectively.

The (29A) to (29D) of FIG. 29 are the histograms showing each number estimation result when the mixing ratios of *E. coli* and *B. subtilis* are 1:10, 2:10, 3:10, and 35:100, respectively.

The (30A) to (30D) of FIG. 30 are the histograms showing each number estimation result when the mixing ratios of *E. coli* and *B. subtilis* are set to 4:10, 45:100 and 1:2, respectively.

The (31A) and (31B) of FIG. 31 are the diagrams combining dispersed states of respective particles when the pulse wavelength and the pulse wave height are used as the feature values.

Figure 32:
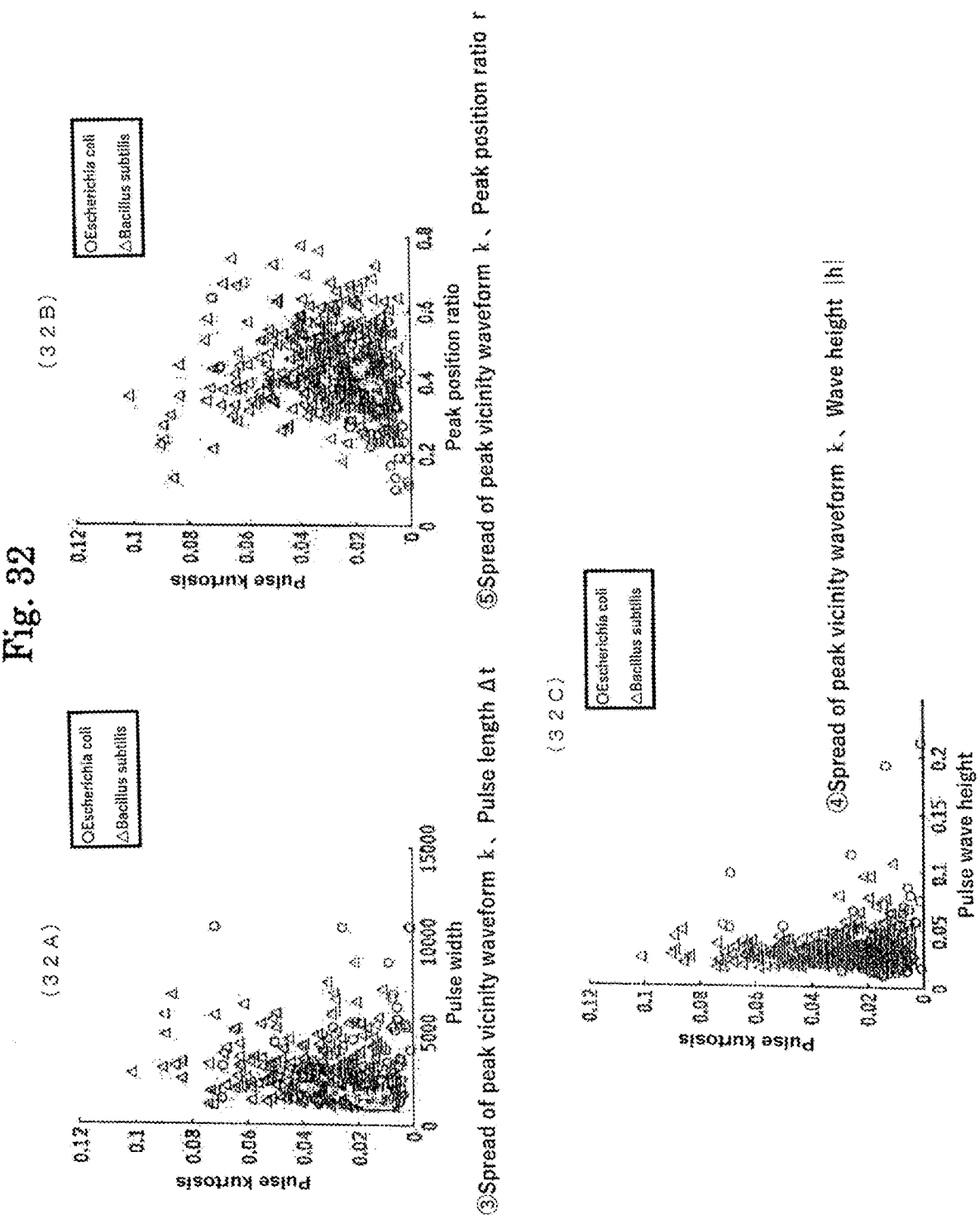
FIG. 32 is a diagram combining dispersed states of respective particles which show the relationship between the spread of the peak vicinity waveform around the peak and the pulse kurtosis as the feature value, the spread of peak vicinity waveform and the peak position ratio as the feature value, and the spread of peak vicinity waveform and the pulse wave height as the feature value.

The (32A), (32B) and (32C) of FIG. 32 are the diagrams combining dispersed states of respective particles when the spread of the peak vicinity waveform and the pulse wavelength are used as the feature values, the spread of peak vicinity waveform and the peak position ratio are used as the feature value, and the spread of peak vicinity waveform and the pulse wave height are used as the feature values, respectively.

From the above performance evaluation experiments, the following evaluation results were obtained.

(1) In the data scatter diagrams of FIG. 31 and FIG. 32, regarding the four feature values, the feature of *E. coli* and *B. subtilis* greatly overlap, but it is recognized that there is a clear difference.

(2) From the estimation result of the type number distribution shown in (27 A) of FIG. 27 etc., the combination of the feature values between the pulse wave height and the peak kurtosis is the most accurate among the feature values of this evaluation verification, and the analysis accuracy of 4 to 12% can be obtained in the evaluation of the weighted mean relative error. In the above-described embodiment, all four types of feature values are extracted, but only a part of feature values (for example, pulse wave height and peak kurtosis) may be extracted for the number analysis based on above verification result.

<About Verification 2 of Analytical Accuracy of Particle Type Number due to Feature Value>

Using the measured current data of E. coli and B. subtilis in the above example, the present inventors performed the verification 2 of the analysis performance of particle type number different from verification 1. In the verification 2, unlike the verification 1, the feature values of the first type and the second type (13 types of (1) to (13)) are calculated and used, and there were verified the relationship between the feature value and the number of sampling data, and the analysis performance according to each combination.

The (42A) and (42B) in FIG. 42 show the estimation evaluation results concerning each feature value combination when sampling is performed at 1 MHz, 500 kHz among all data. The (43A) and (43B) of FIG. 43 show the estimation evaluation results concerning each feature value combination when sampling is performed at 250 kHz and 125 kHz among all data. The (44A) and (44B) in FIG. 44 show the estimation evaluation results concerning each feature value combination when sampling is performed at 63 kHz and 32 kHz among all data. The (45A) and (45B) in FIG. 45 show the estimation evaluation results concerning each feature value combination when sampling is performed at 16 kHz and 8 kHz among all data. FIG. 46 shows the estimation evaluation results concerning each feature value combination when sampling is performed at 4 kHz.

The estimation evaluation results for each combination in these tables are obtained by the cross validation method in the same as (4) of verification 1. The mean accuracy is described in the upper side and the standard deviation indicated in parenthesis is in the lower side. The inertia I, inertia I (normalization), inertia I_w, inertia I_wv, inertia I_w (normalization), and inertia I_wv (normalization) in the table, respectively, show the feature values as the time inertia moment of (8), the normalized time inertia moment of (9), the wave width mean value inertia moment of (10), the wave width dispersion inertia moment of (12), the normalized wave width mean value inertia moment of (11), and the normalized wave width dispersion inertia moment of (13).

FIG. 47 shows the estimation evaluation result concerning each feature value combination among all sampling data. FIG. 48 shows the estimation evaluation result concerning each feature value combination when the high-density sampling is performed at 1 MHz to 125 kHz among all data. FIG. 49 shows the estimation evaluation result concerning each feature value combination when the low-density sampling is performed at 63 kHz to 4 kHz among all data.

FIG. 50 shows the relationship between the sampling frequency and the weighted mean relative error (mean value) for the combination of the top five types of feature values that can obtain the high number estimation accuracy when all sampling data are used (50 A) and when the sampling is performed at high density (50 B). The combinations of the feature values in the top five in FIG. 50 are the wavelength Δt-area m, the wavelength Δt-inertia I, the peak position ratio r-inertia I, the depression θ-inertia I, the inertia I-inertia I_w (normalization).

FIG. 51 shows the graph (51A) between the sampling frequency and the weighted mean relative error (mean value) with respect to the combination of the top five types of feature values that can obtain the high number estimation accuracy when the sampling is performed with low density, and shows the graph (51B) between the sampling frequency and the weighted mean relative error (mean value) with respect to the combination of the four types of feature values when all the sampling data are used.

The values on the vertical axis in FIGS. 50 and 51 are the mean values of weighted mean relative errors obtained by performing 50 cross validations. The combination of the top five feature values in (51A) is wavelength Δt—area m, wavelength Δt—inertia I, peak position ratio r—area m, depression θ—area m, and area m—inertia I_wv (normalization). The combinations of the four types of feature values in (51B) are wavelength Δt—area m, wavelength Δt—inertia I, kurtosis k—wave height |h|, kurtosis k—peak position ratio r.

The results obtained from Verification 2 are as follows.

(R1) As shown in FIG. 47 and FIG. 50, when all the sampling data are used, in the combinations of the top five types of feature values such as the wavelength Δt—inertia I, the wavelength Δt—area m, the peak position ratio r—inertia I, the depression θ—inertia I and inertia I—Inertia I_w (normalization), the high number estimation accuracy can be obtained. The number estimation accuracy (weighted mean relative error) due to the combinations of these feature values is, for example, about 9 to 10% in the sampling region of 250 to 1000 kHz with the wavelength Δt—inertia I, about 9 to 10% in the sampling region of 125 to 250 kHz with the wavelength Δt—area m and about 13 to 15% in the sampling region of 16 to 63 kHz with the wavelength Δt—inertia I.

(R2) As shown in FIG. 48, when it is used the high-density sampling data smaller than full sampling data, the feature value giving the high number estimation accuracy are, if showing the combination of the top five types, the wavelength Δt—inertia I, the wavelength Δt—area m, the peak position ratio r—inertia I, the inertia I—inertia I_w, and the depression angle θ—inertia I. The number estimation accuracy (weighted mean relative error) due to the combination of these feature values is, for example, about 9 to 10% in the sampling region of 250 to 1000 kHz with the wavelength Δt—inertia I, about 9 to 10% in the sampling region 125 to 250 kHz with the wavelength Δt—area m, and about 13 to 15% in the sampling region of 16 to 63 kHz with wavelength Δt—inertia I.

(R3) As shown in FIG. 49, when it is used the low-density sampling data much smaller in comparison with high-density sampling data, the feature value giving the high number estimation accuracy are, if showing the combination of the top five types, the wavelength Δt—area m, wavelength Δt—inertia I, depression θ—area m, area m—inertia I_wv (normalization), peak position ratio r—area m. The number estimation accuracy (weighted mean relative error) due to the combination of these feature values is about 9 to 10% in the sampling region of 250 to 1000 kHz with the wavelength Δt—inertia I, about 9 to 10% in the sampling region of 125 to 250 kHz with the wavelength Δt—area m, and about 13 to 16% in the sampling region of 16 to 63 kHz with wavelength Δt—inertia I.

(R4) As can be seen from (R1) to (R3), the highly accurate number estimation can be carried out even by using the combination of feature value of the first type and the second type. Furthermore, according to the number analyzing method of the present invention, even if the sampling number is not sufficiently large, when the predetermined sampling number can be obtained, the number analysis can be performed with the same accuracy as when it is sufficient.

For example, in the combination of the kurtosis k and the peak position ratio r examined in Verification 1, a maximum error of 12% was generated, but for example, in the case of using the feature value of the wavelength Δt—inertia I, it is possible to perform the number estimation process with high accuracy of about 9% using the high density sampling data at 1 MHz to 125 kHz even if all data is not used, that is, it is partial data. Therefore, the number analyzing device according to the present embodiment can be applied not only to the stationary number analysis, but also to the quarantine inspection and the medical site requiring urgency, so that it can be used as a suitable inspection tool that can be implemented quickly for judgement of the presence or absence of particles or the number of bacteria or the like.

<About Verification 3 of Number Analysis Process Time>

Since in the number estimation, the calculation time is required for the iterative calculation due to the Hasselblad method, the comparison and examination of the feature values are verified in verification 3 with respect to the relation between the required calculation time and the sampling frequency. In the comparative examination example of Verification 3, there are used four kinds of the feature value combinations such as the wavelength Δt—area m, the wavelength Δt—inertia I, the kurtosis k—wave height |h| and the kurtosis k—peak position ratio r shown in (51B) of FIG. 51. These combinations are combinations with good cross validation accuracy compared to other combinations. Since the time required for the calculation of the number analysis includes the time required for the feature value creation and the calculation time required for the iterative calculation due to the Hasselblad method, there are compared and studied the calculation time CT1 required for the feature value creation, the calculation time CT2 required for the iterative calculation due to the Hasselblad method and their total calculation time CT3(=CT1+CT2). In this case, each required calculation time is the mean value of each calculation time obtained by performing 50 cross validations.

Figure 53:
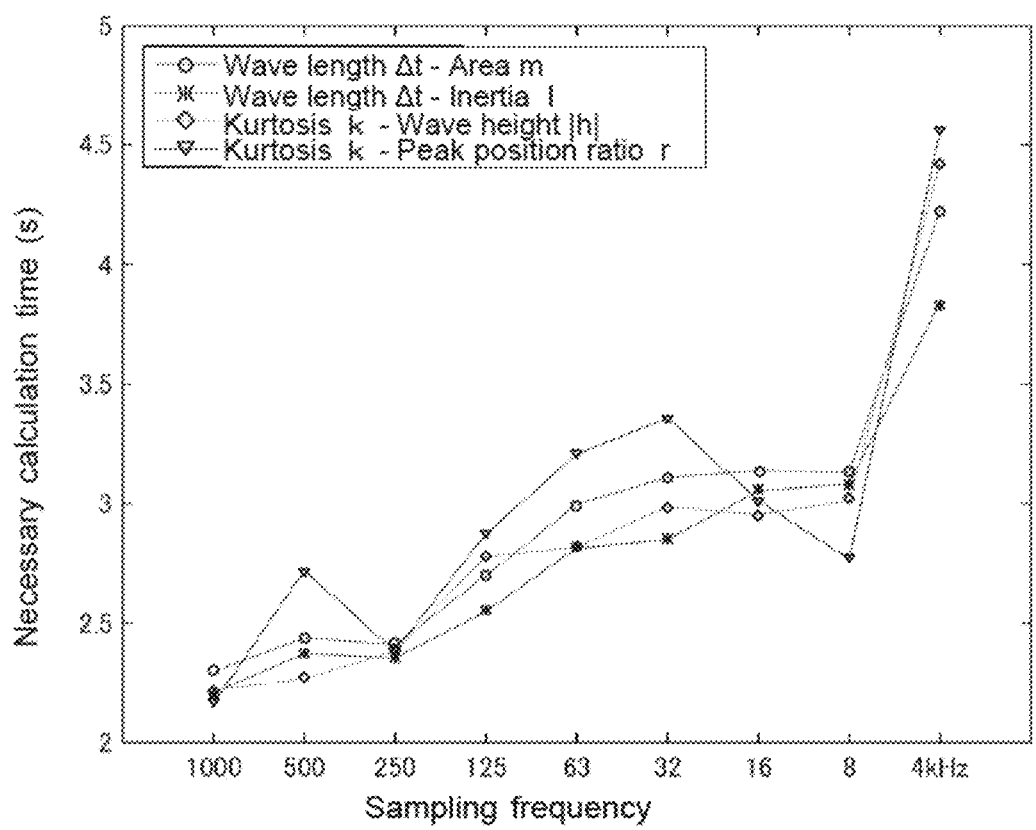
FIG. 53 is a graph between the sampling frequency and the necessary calculation time (second) showing the calculation time required for iterative calculation by Hasselblad method for each combination of four types of feature values.

FIG. 52 is the graph (52A) of the sampling frequency (kHz)—the required calculation time (second) showing the total calculation time CT3 for each of the four types of feature value combinations, and the graph (52B) of the sampling frequency (kHz)—the required calculation time (second) showing the calculation time CT1 required for the feature value creation with respect to each of feature value combinations. FIG. 53 is the graph of the sampling frequency-the required calculation time (second) showing the calculation time CT2 for each feature value combination.

As shown in (52 A), the feature value combination G1 of the wavelength Δt—area m and the wavelength Δt—inertia I is almost the same total calculation time, and the feature value combination G2 of the kurtosis k—wave height |h| and the kurtosis k—the peak position ratio r has approximately the same total calculation time. As shown in (52 B), the calculation time required for generating each feature value of the feature value combination G1 is the same, and the calculation time required for generating each feature value of the feature value combination G2 is the same. As shown in FIG. 53, the time required for the iterative calculation due to the Hasselblad method can be processed in a short time of about 3, 5 seconds or less in the sampling region at 1 MHz to 16 kHz in any of the feature value combinations G1 and G2.

Obviously from the comparison result of the feature value combinations G1 and G2 of verification 3, even if it is the same type combination in the first type and the second type, even if it is the different mixing combination, the required calculation time using the feature value can be shortened.

Therefore, according to the number analyzing device of the present embodiment, in addition to the stationary number analysis, for example, it is possible to quickly perform the process of discriminating the presence or absence of particles and the number of bacteria or the like in the quarantine inspection or the medical field requiring urgency.

As can be understood from the above performance evaluation, according to the present embodiment, based on the data group of the detection signal detected by the nanopore device 8, there is executed the particle type distribution estimation program which is the number deriving means in the computer control program (number analysis program), and it is possible to perform the probability density estimation from the data group based on the feature value showing the feature of the waveform of the pulse signal corresponding to the particle passage obtained as the detection signal and it is possible to derive the number of the particle type. Therefore, by using the number analyzing device according to the present embodiment, it is possible to analyze the number or the number distribution corresponding to the type of analyte such as, for example, bacteria, microparticulate material, etc. with high accuracy, so simplification and cost reduction in the number analyzing inspection can be realized. By incorporating the detection signal from the nanopore device 8 directly into the number analyzing device so that data can be stored, the particle type integration analyzing system integrating inspection and analysis may be constructed.

In the number analyzing device according to the present embodiment, the probability density estimation is performed from the data group based on the feature value, and the result of deriving the particle type number is displayed on the display means 7 as the output means or printed out on the printer. Therefore, according to the present embodiment, highly accurate derivation results (particle number, particle number distribution, estimation accuracy, etc.) can be notified promptly in the output form of, for example, the histogram or the dispersive diagram, so that for example, it is possible to use the number analyzing device according to the present embodiment as the useful inspection tool in the quarantine portion or the medical field requiring urgency.

The present invention can be applied not only to a computer terminal such as a specific PC or the like mounted with a number analysis program but also to a storage medium for number analysis which stores a part or all of the number analysis program. That is, since the number analysis program stored in the number analysis storage medium can be installed in a predetermined computer terminal and the desired computer can be operated to perform the number analysis operation, it is possible to carry out the number analysis simply and inexpensively. As the storage medium applicable to the present invention, there are a flexible disk, a magnetic disk, an optical disk, a CD, an MO, a DVD, a hard disk, a mobile terminal, or the like, and any storage medium readable by a computer can be selected and used.

It is to be understood that the present invention is not limited to the above-described embodiments, but includes various modifications, design changes and the like within the technical scope without departing from the technical idea of the present invention.

INDUSTRIAL APPLICABILITY

According to the present invention, it is possible to highly accurately analyze the number or number distribution corresponding to the particle type of bacteria, microparticulate substances or the like, and to contribute to simplifying, expediting and low cost in the number analyzing inspection of the analytes. The number analyzing technique according to the present invention is useful, for example, for the medical examination contingent on time and can also be applied to the examination of small amount of bacteria virus before infectious symptoms become apparent, so that it also becomes an influential analytical technology, and it can be applied to a wide range such as pre-shipment inspection and quarantine inspection of food requiring a quick inspection result.

DENOTATION OF REFERENCE NUMERALS

1 Personal computer
2 CPU
3 ROM
4 RAM
5 Data file storage portion
6 Input means
7 Display means
8 Micro-nanopore device
9 Chamber
10 Substrate
11 Partition Wall
12 Through-hole
13 Electrode
14 Electrode
15 Power supply
16 Amplifire
17 Operational amplifire
18 Recess portion
19 Feedback resistor
20 Voltmeter
21 Subject
22 *Escherichia coli*
23 *Bacillus subtilis*
24 Electrolytic solution

The invention claimed is:

1. A number analyzing method comprising:
arranging a partition wall with a through-hole and electrodes disposed on a front side and a back side of the partition wall through the through-hole;
supplying a flowable material containing particulate or molecular analytes to one side of the partition wall;
obtaining detection signals of an electrical conduction change between the electrodes caused by passage of the particulate or molecular analytes through the through-hole; and
analyzing a number of each analyte type of the particulate or molecular analytes by executing a computer control program based on data of the detection signals, and
wherein the computer control program is configured to perform a probability density estimation from a data group based on a feature value indicating feature of waveforms of pulse signals obtained as the detection signals which correspond to the passage of the particulate or molecular analytes,
wherein the computer control program includes a number deriving means configured to derive the number of each analyte type,
wherein the feature value shows global feature of waveforms of the pulse signals, and
wherein the feature value is:
a time inertia moment determined by mass and rotational radius when the mass is constructive to a time division area centered at a pulse start time and the rotational radius is constructive to time leading from the center to the time division area,
a normalized time inertia moment determined when the time inertia moment is normalized so as that a wave height becomes a reference value,
a wave width mean value inertia moment determined by mass distribution and rotational center when the mass distribution is constructive to mean value difference vector whose vector component is a mean value difference of the same wave height position in which the waveform is equally divided in the wave height direction and the mean value of time values is calculated for each division unit before and after each pulse peak and the rotational center is constructive to a time axis of waveform foot,
a normalized wave width mean value inertia moment determined when the wave width mean value inertia moment is normalized so as that the wavelength becomes a standard value,
a wave width dispersion inertia moment determined by mass distribution and rotational center when the mass distribution is constructive to dispersion vector whose vector component is dispersion in which a waveform is equally divided in the wave height direction and the dispersion is calculated from a time value for each division unit and the rotational center is constructive to a time axis of waveform foot, or
a normalized wave width dispersion inertia moment determined when the wave width dispersion inertia moment is normalized so as that the wavelength becomes a standard value.

2. The number analyzing method according to claim 1, wherein the computer control program includes:
a base line extraction means configured to extract a base line at no passage of analytes from a data of the detection signals or fluctuation components in the detection signals;
a pulse extraction means configured to extract a signal data over a predetermined range based on the base line as a data of the pulse signals; and
a feature value extraction means configured to extract the feature value from the data of extracted pulse signals.

3. The number analyzing method according to claim 2, wherein the base line extraction means is configured to exclude noise data contained in the base line by using a filter.

4. The number analyzing method according to claim 3, wherein the filter comprises a Kalman filter.

5. The number analyzing method according to claim 2, wherein the base line extraction means is configured to exclude fluctuations due to noise data and weak measured current in the base line by using a filter.

6. The number analyzing method according to claim 2, wherein the base line extraction means is configured to remove disturbances in the base line by using a filter.

7. A storage medium for number analysis comprises a non-transitory storage medium in which said computer control program described in claim 1 is stored.

8. A number analyzing device comprising:
a partition wall with a through-hole,
electrodes disposed on a front side and a back side of the partition wall through the through-hole;
a flowable material containing particulate or molecular analytes supplied to one side of the partition wall;
a computer control program configured to analyze the number of each analyte type based on a data of detection signals when the detection signals are obtained through an electrical conduction change caused between the electrodes by passage of the particulate or molecular analytes through the through-hole;

a non-transitory storage means configured to store the data of detection signals; and a control means configured to control execution of the computer control program based on the data of detection signals, wherein the computer control program is configured to perform a probability density estimation from a data group based on a feature value indicating feature of waveforms of pulse signals obtained as the detection signals which correspond to the passage of the particulate or molecular analytes, wherein the computer control program includes a number deriving means configured to derive the number of each analyte type, wherein the feature value shows global feature of waveforms of the pulse signals, and wherein the feature value is:
- a time inertia moment determined by mass and rotational radius when the mass is constructive to a time division area centered at a pulse start time and the rotational radius is constructive to time leading from the center to the time division area,
- a normalized time inertia moment determined when the time inertia moment is normalized so as that a wave height becomes a reference value,
- a wave width mean value inertia moment determined by mass distribution and rotational center when the mass distribution is constructive to mean value difference vector whose vector component is a mean value difference of the same wave height position in which a waveform is equally divided in a wave height direction and a mean value of time values is calculated for each division unit before and after each pulse peak and the rotational center is constructive to a time axis of waveform foot,
- a normalized wave width mean value inertia moment determined when the wave width mean value inertia moment is normalized so as that the wavelength becomes a reference value,
- a wave width dispersion inertia moment determined by mass distribution and rotational center when the mass distribution is constructive to dispersion vector whose vector component is dispersion in which the waveform is equally divided in the wave height direction and the dispersion is calculated from a time value for each division unit and the rotational center is constructive to a time axis of waveform foot, or
- a normalized wave width dispersion inertia moment determined when the wave width dispersion inertia moment is normalized so as that the wavelength becomes a standard value.

9. The number analyzing device according to claim 8, wherein the computer control program includes:
   a base line extraction means configured to extract a base line at no passage of analytes from a data of the detection signals or fluctuation components contained in the detection signals;
   a pulse extraction means configured to extract signal data over a predetermined range based on the base line as a data of pulse signals; and
   a feature value extraction means configured to extract the feature value from the data of extracted pulse signals.

10. The number analyzing device according to claim 9, further comprising an output means configured to output number data derived by the number deriving means with a predetermined output form for each analyte type.

11. The number analyzing device according to claim 9, wherein the base line extraction means is configured to exclude noise data contained in the base line by using a filter.

12. The number analyzing device according to claim 11, the filter comprises a Kalman filter.

13. The number analyzing device according to claim 8, further comprising an output means configured to output number data derived by the number deriving means with a predetermined output form for each analyte type.

* * * * *